US006900301B2

(12) United States Patent
Cook et al.

(10) Patent No.: US 6,900,301 B2
(45) Date of Patent: May 31, 2005

(54) BACKBONE MODIFIED OLIGONUCLEOTIDE ANALOGUES

(75) Inventors: Phillip Dan Cook, Carlsbad, CA (US); Yogesh Shantilal Sanghvi, San Marcos, CA (US); Jean Jacques Vasseur, Carlsbad, CA (US); Francoise Debart, Carlsbad, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 21 days.

(21) Appl. No.: 10/153,320

(22) Filed: May 22, 2002

(65) Prior Publication Data

US 2003/0045705 A1 Mar. 6, 2003

Related U.S. Application Data

(63) Continuation of application No. 09/058,470, filed on Apr. 10, 1998, now abandoned, which is a division of application No. 08/763,354, filed on Dec. 11, 1996, now Pat. No. 5,965,721, which is a division of application No. 08/150,079, filed as application No. PCT/US92/04294 on May 21, 1992, now Pat. No. 5,610,289, which is a continuation-in-part of application No. 07/703,619, filed on May 21, 1991, now Pat. No. 5,378,825, which is a continuation-in-part of application No. 07/566,836, filed on Aug. 13, 1990, now Pat. No. 5,223,618, which is a continuation-in-part of application No. 07/558,663, filed on Jul. 27, 1990, now Pat. No. 5,138,045.

(51) Int. Cl.$^7$ .................. C07H 21/02; C07H 21/04
(52) U.S. Cl. .................. 536/23.1; 435/90; 435/91.2; 435/91.5; 435/87; 435/91.1; 536/25.34; 536/25.3; 536/25.31; 536/22.1; 536/25.6
(58) Field of Search ................... 435/90, 91.2, 91.5, 435/87, 91.1; 536/25.34, 23.1, 25.3, 25.31, 25.6, 22.1

(56) References Cited

U.S. PATENT DOCUMENTS

| | | | |
|---|---|---|---|
| 3,687,808 A | 8/1972 | Merigan et al. | 435/91.3 |
| 4,469,863 A | 9/1984 | Ts'o et al. | 536/24.5 |
| 4,511,713 A | 4/1985 | Miller et al. | 536/27 |
| 4,591,614 A | 5/1986 | Miller et al. | 525/54.11 |
| 5,264,562 A | 11/1993 | Matteucci | 536/23.1 |
| 5,264,564 A | 11/1993 | Matteucci | 536/23.1 |
| 5,268,464 A | 12/1993 | Brill | 536/25.3 |
| 5,378,825 A | 1/1995 | Cook et al. | 536/25.34 |
| 5,580,722 A | 12/1996 | Foulkes et al. | 435/6 |
| 5,610,289 A * | 3/1997 | Cook et al. | 536/25.34 |
| 5,658,731 A | 8/1997 | Sproat et al. | 435/6 |
| 5,665,543 A | 9/1997 | Foulkes et al. | 435/6 |
| 5,776,502 A | 7/1998 | Foulkes et al. | 424/617 |
| 5,863,773 A | 1/1999 | Gunawardana et al. | 435/118 |

FOREIGN PATENT DOCUMENTS

| | | |
|---|---|---|
| EP | 0 269 574 A2 | 6/1988 |
| EP | 0287313 | 10/1988 |
| EP | 0378518 | 7/1990 |
| EP | 0 381 335 A1 | 8/1990 |
| EP | 0417999 | 3/1991 |
| WO | WO 86/05518 | 9/1986 |
| WO | WO 89/11486 | 11/1989 |
| WO | WO 89/12060 | 12/1989 |
| WO | WO 90/08156 | 7/1990 |
| WO | WO 92/02534 | 2/1992 |
| WO | WO 92/03568 | 3/1992 |
| WO | WO 92/05186 | 4/1992 |
| WO | WO 92/20822 | 11/1992 |
| WO | WO 93/18052 | 9/1993 |

OTHER PUBLICATIONS

Abdel–Magid, A.F. et al., "Reductive Amination of Aldehydes and Ketones by Using Sodium Triacetoxyborohydride", *Tetrahedron Letts.*, 1990, 31, 5595–5598.

Bankston, D.D. et al., "A Short Synthesis of 5'–O–Trityl–Protected threo– and erythro–3'–Cyano–3'–deoxythymidine Epimers Using Free–Radical Chemistry", *J. Heterocyclic Chem.*, 1992, 29, 1405–1407.

Barton, D.H.R. et al., "A 'One–Pot' Synthesis of Sulfenamides", *J. Org. Chem.*, 1991, 56, 6702–6704.

Barton, D.H.R. et al., "Stereoselectivity in Radical Reactions of 2'–Deoxynucleosides. A Synthesis of an Isotere of 3'–Azido–3'–Deoxythymidine–5'–Monophosphate (AZT–5' Monophosphate)", *Tetrahedron Letts.*, 1989, 30, 4969–4972.

Baud, M.V. et al., "Improved Procedure for the Regiospecific Synthesis of 2'–Deoxyribonucleosides", *Tetrahedron Letts.*, 1990, 31, 4437–4440.

Beaucage, S.L. et al., "Advances in the Synthesis of Oligonucleotides by the Phosphoramidite Approach", *Tetrahedron*, 1992, 48, 2223–2311.

Beaucage, S.L. et al., "The Synthesis of Modified Oligonucleotides by the Phosphoramidite Approach and their Applications", *Tetrahedron*, 1993, 49, 6123–6194.

Bergstrom, D.E., "An Improved Synthesis of 3–Keto–5–O–Tritylthymidine", *Nucleosides and Nucleotides*, 1989, 8(8), 1529–1523.

Bodenteich, M. et al., "Synthesis of Enantiomerically Pure Carbocyclic 3'–Azido–2',3'–Dideoxythymidine. A Potential Anti–AIDS Drug", *Tetrahedron Letts.*, 1987, 28, 5311–5312.

(Continued)

Primary Examiner—James O. Wilson
Assistant Examiner—Patrick Lewis
(74) Attorney, Agent, or Firm—Isis Patent Department

(57) ABSTRACT

Therapeutic oligonucleotide analogues which have improved nuclease resistance and improved cellular uptake are provided. Replacement of the normal phosphorodiester inter-sugar linkages found in natural oligomers with four atom linking groups forms unique di- and poly-nucleosides and nucleotides useful in regulating RNA expression and in therapeutics. Methods of synthesis and use are also disclosed.

28 Claims, 2 Drawing Sheets

OTHER PUBLICATIONS

Brown, T. et al., "Modern machine–aided methods of oligodeoxyribonucleotide synthesis", *Oligonucleotides and Analogs A Practical Approach*, 1991, Chapter 1, Ekstein, F., ed., IRL Press, Oxford, 1–24.

Camarasa, M.J. et al., "Aldol Reaction of Nucleoside 5'–Carboxaldehydes with Acetone. Synthesis of 5'–C–Chain Extended Thymidine Derivatives", *Nucleosides & Nucleotides*, 1990, 9, 533–546.

Cormier, J.F. et al., "Synthesis of hexanucleotide analogues containing diisopropylsilyl internucleotide linkages", *Nucl. Acids Res.*, 1988, 16, 4583–4594.

Cosstick, R. et al., "Synthesis and properties of dithymidine phosphate analogues containing 3'–thothymidine", *Nucl. Acids Res.*, 1989, 18, 829–835.

Coull, J.M. et al., "Synthesis and Characterization of a Carbamate–Linked Oligonucleoside", *Tetrahedron Letts.*, 1987, 28, 745–748.

Curran, D.P. et al., "Radical Addition Reactions", *Comprehensive Organic Synthesis*, Trost, B.M. et al, eds., 1991, 4, Pergamon Press, Oxford, 715–831.

Debart, F. et al., "Intermolecular Radical C–C Bond Formation: Synthesis of a Novel Dinucleoside Linker for Non–anionic Antisense Oligonucleosides", *Tetrahedron Letts.*, 1992, 33, 2645–2648.

Egholm, M. et al., "Recognition of Guanine and Adenine inDNA by Cytosine and Thymine Containing Peptide Nucleic Acids (PNA)", *J. Am. Chem Soc.*, 1992, 114, 9677–9678.

Egholm, et al., "Peptide Nucleic Acids (PNA). Oligonucleotide Analogues with an Achiral Peptide Backbone", *J. Am. Chem. Soc.*, 1992, 114, 1895–1897.

Etzold, G. et al., "The Extension of the Sugar Chain of Thymidine: a New Route to 5'–Deoxyhexose Nucleosides", *Chem. Comm.*, 1968, 422.

Fiandor, J. et al., "Synthesis of 3'–Deoxy–3'(2–Propynyl) Thymidine and 3'–Cyanomethyl–3'–Deoxythymidine, Analogs of AZT", *Tetrahedron Letts.*, 1990, 21, 597–600.

Fikes, L.E. et al., "Preassociating α–Nucleophiles", *J. Am. Chem. Soc.*, 1992, 114, 1493–1495.

Fleet, G.W. et al., "Methyl 5–O–Tert–Butyldiphenylsilyl–2–Deoxy–αβ–D–Threo–Pentofuranoside as a Divergent Intermediate for the Synthesis of 3'–Substituted–2',3'–Dideoxynuclesides: Synthesis of 3'–Azido–3'–Deoxythymidine, 3'–Deoxy–3'–Fluorothymidine and 3'–Cyano–3'–Deoxythymidine", *Tetrahedron*, 1988, 44, 625–636.

Gait, M.J., ed., "Synthetic Analogues of polynucleotides. Part XII. Synthesis of Thymidine Derivatives containing an Oxyacetamido– or an Oxyformamid—linkage instead of a Phosphodiester Group", *J. C. S. Perkin I*, 1974, 1684–1686.

Giannis, A. et al., "Fragmentation and Wittig Olefination of Glucosamine Derivatives—A Simple Route to Open Chain Amino Sugars and Chiral Glycerols", *Tetrahedron*, 1988, 44, 7177–7180.

Goodchild, J., "Conjugtes of Oligonucleotides and Modified Oligonucleotides: A Review of their synthesis and Properties", *Bioconjugate Chem.*, 1990, 1, 165–187.

Goodchild, J., "Inhibition of Gene Expression by Oligonucleotides", *Oligodeoxynucleotides*, 1989, CRC Press, Boca Raton, 53–78.

Greene et al., "Protection for the Carbonyl Group", *Protective Groups in Organic Synthesis*, 1991, Chapter 4, John Wiley & Sons, 175–223.

Halford, M.H. et al., "Synthetic Analogues of Polynucleotides", *Nature*, 1968, 217, 638–640.

Hanamoto, T. et al., "SmI$_2$–Promoted Ketyl Radical Addition to O–Benyl Formaldoxime. A New Aminomethylation", *Tetrahedron Letts.*, 1991, 32, 3555–3556.

Hart, D.J. et al., "Bis(trimethylstannyl) benzopinacolate–Mediated Intermolecular Free–Radical Carbon–Carbon Bond–Forming Reactions: A New One–Carbon Homologation", *J. Am. Chem. Soc.*, 1988, 110, 1631–1633.

Hata, T., et al., "One–Step Synthesis of 5'–Azido–nucleosides", *J. Chem. Soc.*, Perkin I, 1980, p. 306.

Hill, J. et al., "3,4–Dihydro–2H–1,4–benzoxazines", 1964, 3709–3713.

Hillgartner, H. et al., "Bis(trimethylzinn) benzpinakolat, sien reversible radikalische Dissoziation und Reaktinonen", *Liebigs Ann. Chem.*, 1975, 586–599.

Horwitz, H.P. et al., "Nucleosides. V. The Monomesylates of 1–(2'–Deoxy–β–D–lyxofuranoyl) thymine", *Notes*, 1964, 29, 2076–2078.

Hronowski, L.J.J. et al., "Synthesis of New Carbocyclic Analogues of 3'–Azido–and 3'–Amino–2',3'–dideoxynucleosides", 1990, 1547–1548.

Huang, Z. et al., "Non–ionic antisense oligonucleotides containing sulfide and sulfone linkages in place of phosphodiester groups in natural oligonucleotides", *J. Cell. Biochem.*, 1991, Supp. 150, 19, Abstract CD 209.

Huang, Z. et al., "Building Blocks for Oligonucleotide Analogues with Dimethylene Sulfide, Sulfoxide, and Sulfone Groups Replacing Phosphodiester Linkages", *J. Org. Chem.*, 1991, 56, 3869–3882.

Hyrup, B. et al., "Modification of the Biniding Affinity of Peptide Nucleic Acids (PNA). PNA with extended Backbones Consisting of 2–Aminoethyl–β–alanine or 3–Aminopropylglycine Units", *J. Chem. Soc. Chem. Commun.*, 1993, 518–519.

Inouye, M. et al., "Selective Coloration of Spiro Pyridopyrans for Guanosine Deriavatives", *J. Am. Chem. Soc.*, 1992, 114, 778–780.

Jenkins, S.R. et al., "9–(2–Methyl–β–D–ribofuranosyl) adenine (2'–Methyladenosine", *Synthetic Procedures in Nucleic Acid Chemistry*, 149–153.

Jones, G.H. et al., "The Synthesis of 6'–Deoxyhomonucleoside–6'–phosphonic Acids", *J. Am. Chem. Soc.*, 1968, 90, 5337–5338.

Jones, M. and Roberts, "Synthesis of Carbocyclic Nucleosides: Preparation of (–)–5'–Homoaristeromycin and Analogues", *J. Chem. Soc. Perkin Tran.*, 1988, 2927–2932.

Kappler, F. et al., "Homoadenosine (9–(5–Deoxy–β–D–ribo–Hexofuranosyl)Adenine) Hydroboration of 5',6'–Anhydro–2',3'–O–Isopropylidenehomoadenosine formed from 2',3'–O–Isopropylideneadenosine–5'–aldehyde by a Wittig Reaction", *Nucleic Acid Chemistry*, 1991, John Wiley & Sons, Inc., 240–244.

Kawai, S.H. et al., "Single–Stranded DNA & RNA Binding: Backbone–Modified polynucleotide Analogues", *Third Chemical Congress of North America*, Jun. 5–10, 1988, Abstract #ORGN 318.

Kirshenbaum, M.R. et al., "Novel Oligonucleotide Analogues with a Sulfur Based Linkage", *The Fifth San Diego Conference on Nucleic Acids*, Nov. 14–16, 1990, *Abstract CD 210*, 28.

Kondo, K. et al., "Synthesis of 5'(3')–O–amino nucleosides", 1985, *Symposium Series 16*, 93–96.

Koole, L.H. et al., "Enhanced stability of a Watson & crick DNA duplex structure by methylation of the phosphate groups in one strand", *Proc. K. New. Acad. Wet.*, 1987, 90, 41–46.

Koster, H. et al., "Dialkyl Aluminum Chloride: A reagent for Removal of Trityl Ethers of Deoxynucle sides, Deoxynucleotides, and Oligodeoxynucleotides,", 1982, 23, 2641–2644.

Lim, M.I. et al., "Facile Synthesis of a New Orange–Red 7–Amino–6–Nitro–3,4–Dihydro–2H–1,4–Benzoxazine", *203 ACS Natl. Meeting*, Apr. 5–10, 1992, San Francisco, CA.

Lin, T.S. et al., "Synthesis and Biological Activity of Several Amino Analogues of Thymidine", *J. Med. Chem.*, 1978, 21, 109–112.

Loke, S.L. et al., "Delivery of c–myc Antisense Phosphorothioate Oligodeoxynucleotides to Hematopoietic Cells in Culture by Liposome Fusion: Specific Reduction in c–myc Protein Expression Correlates with Inhibition of Cell Growth and DNA Synthesis", *Curr. Topics in Microbio. & Immunol.*, 1988, 141, 282–289.

Ma, M.Y. et al., "Design and synthesis of RNA miniduplexes via a synthtic linker approach. 2. Generation of covalently closed, double–stranded cyclic HIV–1 TAR RNA analogs with high Tat–binding affinity", *Nucl. Acids Res.*, 1993, 21, 2585–2589.

Marcus–Sekura, C.J. et al., "Comparative inhibition of chloramphenicol acetyltransferase gene expression by antisense oligonucleotide analogues having alkyl phosphotriester, methylphosphonate and phosphorothioate linkages", *Nucl. Acids Res.*, 1987, 15, 5749–5763.

Marriott, J.H. et al., "9–(4–Methoxyphenyl) Xanthen–9–Thiol: A useful Reagent for the Preparation of Thiols", *Tetrahedron Letts.*, 1990, 31, 7485–7488.

Matsuda, A. et al., "Synthesis and Biological Activities of 3'–Deoxy–3'–Isocyano, –Isothiocyano, and –Isoelenocyano–Thymidines", *Nucleosides & Nucleotides*, 1990, 9, 587–597.

Matteucci, M., "Deoxyoligonucleotide Analogs Based on Formacetal Linkages", *Tetrahedron Letts.*, 1990, 31, 2385–2388.

Matteucci, M. et al., "Deoxyoligonucleotides Bearing Neutral Analogs of Phosphodiester Linkages Recognize Duplex DNA via Triple–helix Formation", *J. Am. Chem. Soc.*, 1991, 113, 7767–7768.

Matthews, J.A. et al., "Analytical Strategies for the Use of DNA Probes", *Analyt. Biochem.*, 1988, 169, 1–25.

Mazur, A. et al., "Isoteres of Natural Phosphates. 11. Synthesis of a Phosphonic Acid Analogur of an Oligonucleotide", *Tetrahedron*, 1984, 40, 3949–3956.

Mertes, M.P. et al., "Synthesis of Carbonate Analogs of Dinucleosides. 3'–Thymidinyl 5'–Thymidinyl Carbonate, 3'–Thymidinyl 5'–(5–Fluoro–2'–deoxyuridinyl) Carbonate, and 3'–(5–Fluoro–2'–deoxyuridinyl) 5'–Thymidinyl Carbonate", *J. Med. Chem.*, 1969, 12, 154–157.

Miller, P.S., "Non–ionic Antisens Oligonucleotides", *Oligodeoxynucleotides*, 1989, Cohen, J.S. ed., CRC Press, Boca Raton, 79–80.

Miller, P.S. et al., "Biochemical and Biological Effects of Nonionic Nucleic Acid Methylphosphonates", *Biochem.*, 1981, 20, 1874–1880.

Miller, P.S., "Oligonucleoside Methylphophonates as Antisense Reagents", *Bio/Technology*, 1991, 9, 358–362.

Miller, P.S. et al., "Effects of a Trinucleotide Ethyl Phosphotriester, $G^m p(Et)G^m p(Et)U$, on Mammalian Cells in Culture", *Biochem.*, 1977, 16, 1988–1996.

Mirabelli, C.K. et al., "In vitro and in vivo pharmacologic activities of antisense oligonucleotides", *Anti–Cancer Drug Des.*, 1991, 6, 647–661.

Moffatt, J.G. and Jones, G.H., "Synthesis of Isosteric Phosphonate Analogs of Some Biologically Important Phosphodiesters", *J. Am. Chem. Soc.*, 1970, 92, 5510–5513.

Montgomery, J.A. et al., "Nucleosides containing chemically reactive groups 2. Chloromethylketo derivatives of pyrimidine nucleosides", *Nucl. Acids Res.*, 1981, 9, 95–97.

Montgomery, et al. "Potential inhibitors of nucleotidebiosynthesis. 2. Halomethyl ketone derivatives of pyrimidine nucleosides", *J. Med. Chem.*, 1984, 27(5), 680–684.

Motawia, M.S. et al., "A New Route to 2',3'–Dideoxycytidine", *Liebigs Ann. Chem*, 1990, 599–602.

Mungall, W.S. et al., "Carbamate Analogues of Oligonucleotides", *J. Org. Chem.*, 1977, 42, 703–706.

Musicki, B. et al., "Synthesis of Carbohydrate Sulfonates and Sulfonate Esters", *J. Org. Chem.*, 1990, 55, 4231–4233.

Musicki, B., et al., "Synthesis of nucleoside sulfonates and sulfones", *Tetrahedron Letters*, 1991, 32, 1267–1270.

Nair, V. et al., "Regiospecific 5'–Silation of Nucleosides", *Organic Preps. & Proced. Int.*, 1990, 22, 57–61.

Neumeyer, J.L. et al., "Isoquinolines. 4. The Synthesis of $C(\alpha)$–Hydroxylated Tetrahydrobenzylisoquinolines and Related Compounds Using the 4–Oxazolin–2–one System as a Protecting Group", *J. Org. Chem.*, 1973, 38, 2291–2293.

Nicolaou, K.C. et al., "A Mild and General Method for the Synthesis of O–Glycosides", *J. Am. Chem. Soc.*, 1983, 105, 2430–2434.

Nicolaou, K.C. et al., "Carbocyclic Thromboxane $A_2$", *J. Am. Chem. Soc.*, 1980, 10, 1404–1409.

Nielsen, P.E. et al., "Sequence–Selective Recognition of DNA by Strand Displacement with a Thymine–Substituted Polyamide", *Science*, 1991, 254, 1497–1500.

Niitsu et al., "Syntheses of a series of linear pentamines with three and four methylene chain intervals", *Chem. Pharm. Bull.* 1986, 34, 1032–1038.

Damha et al., "An improved procedure for derivatization of controlled–pore glass beads for solid–phase oligonucleotide synthesis", *Nucleic Acids Research* 1990, 18, 3813–3821.

Ogilvie et al., "Synthesis of a thymidine dinucleotide analogue containing an internucleotide silyl linkage", *Tetrahedron Letters*, 1985, 26, 4159–4162.

Parkes, K.E.B., and K. Taylor, "A Short Synthesis of 3'–Cyano–3'–Deoxythymidine", *Tetrahedron Letters*, 1988, 29, 2995–2996.

Pauling, "Molecular architecture and biological reactions", *Chemical & Engineering News*, 1946, 24, 1375–1377.

Perkins et al., "Accelerated displacement of duplex DNA strands by a synthetic circular oligodeoxynucleotide", *J. Chem. Soc., Chem. Commun.*, 1993, 215–216.

Pfitzer, K.E. and J. G. Moffatt, "The synthesis of nucleoside–5' aldehydes", *Journal of American Chemical Society*, 1963, 85, 3027.

Poopeiko et al., "A Simple Method for Azido Group Reduction", *Syn. Lett.* 1991, p. 342.

Prakash et al., "Molecular Recognitioin by Circular Oligonucleotides. Strong Binding of Single–stranded DNA and RNA", *J. Chem. Soc. Chem Commun.* 1991, 1161–1163.

Rawson et al., "The synthesis of 5'–homo–deoxycitidine", *Nucleosides & Nucleotides* 1990, 9, 89–96.

Rebek, Jr., "Molecular Recognition and Biophysical Organic Chemistry", *Ace. Chem. Res.*, 1990, 23, 399–404.

Rentzeperis et al., "Contribution of loops and nicks to the formation of DNA dumbbells: melting behavior and ligand binding", *Biochemistry*, 1993, 32, 2564–2572.

Samano, V. and M.J. Morris, "Mild periodinane oxidation of protected nucleosides to give 2'– and 3'–ketonucleosides. The first isolation of a purine 2'–deoxy–3'–ketonucleoside derivative" *Journal of Organic Chemistry*, 1990, 55, 5186–5188.

Sanghvi, Y. et al., "Synthesis and structure of methylene-(dimethylhdrazo)linked thymidine dimer and their utility as antisense oligonucleotides", *Collect. Czech. Chem. Commun.*, 1993, 58, 158–162.

Schneider and Benner, "Building blocks for oligonucleotide analogs with dimethylene–sulfide, –sulfoxide, and –sulfone groups replacing phosphodiester linkages", *Tetrahedron Letters*, 1990, 31, 335–338.

Secrist et al., "5'–C–chain–extended adenosine derivatives related to sinefungin. Synthesis and biological activity", *Nucleosides and Nucleotides*, 1990, 9(4), 619–627.

Secrist III. et al., "Synthesis and biological activity of 4'–Thionucleosides", Program & Abstracts, Tenth International Roundtable , Nucleosides, Nucleotides and their Biological Applications, Park City, Utah, Sep. 16–20, 1992.

Shaw et al., "Modified deoxyoligonucleotide stable to Exonuclease degradation in Serum", *Nucleic Acids Research*, 1991, 19, 747–750.

Shum, et al., Third Chemical Congress of North America, Organic Chemistry, 1988, Synthesis of 3',5'–Bis (Deoxythymidylyl) Difluoromethylphosphonate, Canada, Jun. 5–10, 1988, Abstract No. 319.

Sproat et al., "2'–O–methyloligoribonucleotides: synthesis and applications", Oligonucleotides and Analogues, F. Eckstein Ed., Ch.3, 49–86, IRL Press, 1991.

Stein, C.A. and Cheng, "Antisense Oligonucleotides as Therapeutic Agents—Is the Bullet Really Magical?", *Science*, 1993, 261, 1004–1012.

Stirchak and Summerton, "Uncharged Stereoregular Nucleic Acid Analogues. I. Synthesis of a Cytosine–Containing Oligomer with Carbamate Internucleoside Linkages", *Journal of Oranic Chemistry* 1987, 52, 4202–4206.

Stirchak, et al., "Uncharged Stereoregular Nucleic Acid Analogs. 2. Morpholino Nucleoside Oligomers with carbamate Internucleoside Linkages", *Nucleic Acids Research*, 1989, 17, 6129–6134.

Suami, T. "Sugar hydrazine derivatives", JP49024457 (Japanese patent)Jun. 22, 1974 (Abstract).

Fleet, G. et al, "Methyl 5–O–Tert–Butyldiphenylsilyl–2–Deoxy–αβ–D–Threo–Pentofuranoside as a Divergent Intermediate for the Synthesis of 3'–Substituted–2', 3'–Dideoxynucleosides: Synthesis of 3'–Azido'3'–Deoxythymidine, 3'–Deoxy–3'–Fluorothymidine and 3'–Cyano–3'–Deoxythymidine", *Tetrahedron* 1988, 44, 625.

Kozikowski, A. et al., "Synthesis and 2D NMR Analysis of a Cyclopropane Containing Analogue of Huperzine A", *Tetrahedron Letters*, 1992, 33, 2656.

Tittensor, J.F., "The preparation of nucleoside carbonates", *J. Chem Soc. (C)*, 1971, 2656–2662.

Townsend et al., "A new and novel approach towards the synthesis of 3'–deoxy–3'–hydroxymethyl ribofuranosides", *Tetrahedron Letters*, 1990, 31, 3101–3104.

Trainor et al., Third Chemical Congress of North America, Organic Chemistry, 1988, The Design and Synthesis of Fluorescence–Tagged Dideoxynucleotides for Automated DNA Sequencing, Canada, Jun. 5–10, 1988, Abstract No. ORGN 317.

Trapani et al., "N–1–alkenyl–n, s–diacyl–2–aminobenzethiols (enamides) by ring–opening of 2,3–dihydro–1,3–benzothiazoles with aliphatic carboxylic anhydrides", *Synthesis* 1988, 84–87.

Tronchet, J.M.J. et al., "Blocked disaccharide analogs bearing an oxyimino interglycosidic bridge", *J. Carbohydrate Chem.*, 1991, 10(4), 723–728.

Tseng & Brown, "Antisense oligonucleotide technology in the development of cancer therapeutics", *Can. Gene Therapy*, 1994, 1(1), 65–71.

Tuladhar et al., "A synthetic route to poly–n, N'–dimethylethylenediamines", *Tetrahedron Letters* 1992, 33, 2203–2206.

Uhlmann, et al., "Antisense oligonucleotides: A new therapeutic principle", *Chemical Review*, 1990, 90(4), 544–584.

Van der Krol et al., "Modulation of eukaryotic gene expression by complementary RNA or DNA sequences", *Biotechniques*, 1988, 6, 958–974.

Vasseur et al., "Oligonucleosides: Synthesis of a Novel Methylhydroxylamine–Linked Nucleoside Dimer and its Incorporation into Antisense Sequences", *J. Am. Chem. Soc.*, 1992, 114, 4006–4007.

Veeneman, G.A. et al., "Synthesis of oligodeoxynucleotides containing thymidines linked via an internucleosidic–(3'–5')–methylene bond", *Recueil des Trav. Chim.*, 1990, 109, 449.

Veeneman, G.A. et al., "An efficient approach to the synthesis of thymidine derivatives containing phosphate–isosteric methylene acetal linkages", *Tetrahedron*, 1991, 47, 1547–1562.

Verheyden et al., "Halo sugar nucleosides. I. Iodination of the Primary Hydroxyl groups of Nucleosides with Methyltriphenoxyphosphonium Iodide ", *J. Org. Chemistry* 1970, 35, 2319–2326.

Verheyden et al., "Halo sugar nucleosides. II. Iodination of secondary hydroxyl groups of nucleosid s with methyltriphenoxyphosphonium iodide", *J. Org. Chem.* 1970, 35, 2868–2877.

Wilson, D.B, "Cellular Transport Mechanisms", *Ann. Rev. Biochem.* 1978, 47, 933–965.

Wu and Chattoapadhyaya, "New Synthesis of 2',3'–Dideoxyl–3'–C–Cyano–2'–Substituted Thymidines by Michael Addition Reactions", *Tetrahedron*, 1989, 45, 855–862.

Yamamoto, Isamu et al., "One–step Synthesis of 5'–Azido–nucleosides", *J.C.S. Perkin I* 1978, 306–310.

Yang et al., "Construction of glycosidic n–o linkages in Oligosaccharides", *J. Am. Chem. Soc.*, 1991, 113, 4715–4716.

Zuckermann et al., "Efficient method for the preparation of peptoids (Oligo(N–substituted glycines) by submonomer solid–phase synthesis", *J. Am. Chem. Soc.* 1992, 114, 10646–10647.

Quadflieg, P. et al., "Synthesis of (3'–5') Methylene Acetal Linked Dinucleosides Containing Cytosine Bases", *Recueil des Travaux Chimiques des Pays–Bas*, 1991, 110, 435–436.

Heinemann, U., et al., "Effect of a Single e'–methylene Phosphonate Linkage on the Conformation of an A–DNA Octamer Double Helix", *Nucleic Acids Res.*, 1991, 19(3), 427–433.

Morr, M., et al., "Building Blocks for the Chemical Synthesis of DNA Containing C(3')–CH$_2$–P Bonds", in *Chemical Synthesis in Molecular Biology*, GBF (Gesellschaft fuer Biotechnologische Forschung Braunschweig–Stoeckheim), Bloecker, et al., Eds., 1987, vol. 8, pp. 107–113.

Khurshid, et al., "The Unique Conformational Stability of Poly–2'–O–Ethyladenylic Acid", *FEBS Letters*, 1972, 28, 25–28.

Kielanowska, et al., "Preparation and properties of poly 2'–O–ethylcytidylic acid", *Nucleic Acids Research*, 1976, 3, 817–824.

Kusmierek, et al., "Alkylation of Cytidine–5'–Phosphate: Mechanisms of Alkylation, Influence of O'–Alkylation on Susceptibility of Pyrimidine Nucleotides to Some Nucleolytic Enzymes, and synthesis of 2'–O–Alkyl Polynucleotides", *ACTA Biochemica Polonica*, 1973, 20, 365–381.

Pike, et al., "Mixed Alkylation(Methylation and Ethylation) of Andenosine by Diazoethane in Aqueous 1,2–Dimethoxyethane", *J. Org. Chem.*, 1974, 39, 3674–3676.

Ransford, et al., "2'–O–Ethyl Pyrimidine Nucleosides", *J. Carbohydrates—Nucleosides & Nucleotides*, 1974, 1, 275–278.

Rottman, et al., "Influence of 2'–O–Alkylation on the Structure of Single–Stranded Polynucleotides and the Stability of 2'–O–Alkylated Polynucleotide Complexes", *Biochemistry*, 1974, 13, 2762–2771.

Tazawa, et al., "A Novel Procedure for the Synthesis of 2'–O–Alkyl Nucleotides", *Biochemistry*, 1972, 11, 4931–4937.

Gura, et al., 1995, "Antisense Has Growing Pains", *Science*, 270, 575–577.

Crystal, R.G., "Transfer of Genes to Humans: Early Lessons and Obstacles to Success", 1995, *Science, 270*, 404–410.

Grimm, et al., "Characterization of a Naturally Occurring Antisense Transcript to 5–Lipoxygenase in HL–60 Cells", 1992, *FASEB J. 6(5)*, A1644, Abstract 4098.

Bertelsen, et al., "Tumor Suppressor Genes: Prospects for Cancer Therapies", 1995, *BIO/TECHNOL, 13*, 127–131.

Webster's II New Riverside University Dictionary, Soukhanov, et al., Eds., 1984, Houghton Mifflin Company, Boston, MA, p. 1108.

Miller, P.S., "Non–ionic Antisense Oligonucleotides", in: Oligonucleotides Antisense Inhibitors of Gene Expression (Cohen, J.S., ed.), CRC Press, Boca Raton, FL, 1989, pp. 79–93.

Webster's II New Riverside University Dictionary, 1984, Houghton Mifflin Company, Boston, MA, p. 67.

Wickstrom, E., "Strategies for administering targeted therapuetic oligodeoxynucleotides", 1992, TIBTECH, 10, 281–287.

Johnson, C.R., et al., "Synthesis of the Carbocyclic Nucleoside (–)–Neplanocin A", *Tetrahedron Letters*, 1987, 28, 4131–4134.

Atkinson, T. And Smith, M., "Oligonucleotide Synthesis Practical Approach", M.J. Gait, Ed., IRL Press, Washington, D.C., 1985, p. 49.

Nelson, et al., "Bifunctional Oligonucleotide Probes Synthesized Using a Novel LPG Support are Able to Detect Single Base Pair Mutations", *Nucleic Acids Res.*, 1989, 17, 7179.

Beaucage, S.L., et al., "3H–1,2–Benzodithiole–3–one 1,1–Dioxide as an Improved Sulfurinzing Reagent in the Solid–Phase Synthesis of Oligodeoxyribonucleoside Phosphorothioates", *Am. Chem. Soc..*, 112, 1990, 1253–1254.

Ceruzzi, M. And Draper, K., "The Cellular and Extracellular Fate of Oligodeoxyribonucleotides in Tissue Culture Systems", *Nucleosides & Nucleotides, 8*, 1989, 815–818.

Lemaitre, M., et al., "Specific antiviral activity of a poly(L–lysine)–conjugated oligodeoxyribonucleotide sequence complementary to vesivular stomatitis virus N protein mRNA initiation site", *Proc. Natl. Acad. Sci. USA*, 1987, 84, 648–652.

Letsinger, et al., "Cholesteryl–conjugated oligonucleotides: Synthesis, properties, and activity as inhibitors of replication of human immunodeficiency virus cell culture", *Proc. Natl. Acad. Sci. USA*, 1989, 86, 6553–6556.

Loke, S.L., et al., "Characterization of Oligonucleotide transport into living cells", *Proc. Natl. Acad. Sci. USA.*, 1989, 86, 3473–3478.

Overman, et al., "Tert–Butyldephenylsilylamines: A Useful Protecting Group for Primary Amines", *Tetrahedron Lett.*, 1986, 27, 4391–4394.

Stevenson, M. And Iversen, P.L., "Inhibition of Human Immunodeficiency Virus Type 1–Mediated Cytopathic Effects by Poly(L–lysine)–Conjugated Synthetic Antisense Oligodeoxyribonucleotides", *J. Gen. Virol.*, 1989, 70, 2673–2682.

Wu, G.Y. and Wu, C.H., "Evidence for Targeted Gene Delivery to hep g2 Hepatoma Cells in vitro", *Biochemistry*, 1988, 27, 887–892.

Zon, G., Oligodeoxynucleotides: "Antisense Inhibitors of Gene Expression", 234–247, J.S. Cohen, Ed. (CRC Press, Boca Raton, FL 1989.

* cited by examiner

BACKBONE MODIFIED OLIGONUCLEOTIDE ANALOGUES

CROSS REFERENCE TO RELATED APPLICATIONS

This application is a continuation of Ser. No. 09/058,470, filed Apr. 10, 1998 now abandoned which in turn is a divisional of Ser. No. 08/763,354 (now U.S. Pat. No. 5,965,721) filed Dec. 11, 1996 which is a divisional of Ser. No. 08/150,079 (now U.S. Pat. No. 5,610,289) file Apr. 7, 1994 which is a 371 of PCT/US92/04294, filed May 21, 1992 which is a continuation-in-part of Ser. No. 07/703,619 (now U.S. Pat. No. 5,378,825) filed May 21, 1991 which is a continuation-in-part of Ser. No. 07/566,836 (now U.S. Pat. No. 5,223,618) filed Aug. 13, 1990 which is a continuation-in-part of Ser. No. 07/558,663 (now U.S. Pat. No. 5,138,045) filed Jul. 27, 1990), the entirety of which is incorporated herein by reference.

FIELD OF THE INVENTION

This invention relates to the design, synthesis and application of nuclease resistant oligonucleotide analogues which are useful for therapeutics, diagnostics and as research reagents. Oligonucleotide analogues are provided that have modified linkages which replace phosphorodiester bonds which normally serve as inter-sugar linkages in natural nucleic acids. Such analogues are resistant to nuclease degradation and are capable of modulating the activity of DNA and RNA. Methods for synthesizing these oligonucleotide analogues and for modulating the production of proteins, utilizing the oligonucleotide analogues of the invention are also provided as are intermediate compositions and methods.

BACKGROUND OF THE INVENTION

It is well known that most of the bodily states in mammals including most disease states, are effected by proteins. Such proteins, either acting directly or through their enzymatic functions, contribute in major proportion to many diseases in animals and man.

Classical therapeutics has generally focused upon interactions with such proteins in an effort to moderate their disease causing or disease potentiating functions. Recently, however, attempts have been made to moderate the actual production of such proteins by interactions with the molecules, i.e. intracellular RNA, that direct their synthesis. These interactions have involved the hybridization of complementary "antisense" oligonucleotides or certain analogues thereof to RNA. Hybridization is the sequence-specific hydrogen bonding of oligonucleotides or oligonucleotide analogues to RNA or single stranded DNA. By interfering with the production of proteins, it has been hoped to effect therapeutic results with maximum effect and minimal side effects. In the same way, oligonucleotide analogues may modulate the production of proteins by an organism.

The pharmacological activity of antisense oligonucleotides and oligonucleotide analogues, like other therapeutics, depends on a number of factors that influence the effective concentration of these agents at specific intracellular targets. One important factor for oligonucleotides is the stability of the species in the presence of nucleases. It is unlikely that unmodified oligonucleotides will be useful therapeutic agents because they are rapidly degraded by nucleases. Modifications of oligonucleotides to render them resistant to nucleases is therefore greatly desired.

Modifications of oligonucleotides to enhance nuclease resistance have generally taken place on the phosphorus atom of the sugar-phosphate backbone. Phosphorothioates, methyl phosphonates, phosphoramidates and phosphotriesters have been reported to confer various levels of nuclease resistance; however, the phosphate modified oligonucleotides have generally suffered from inferior hybridization properties. Cohen, J. S., ed. *Oligonucleotides: Antisense Inhibitors of Gene Expression*, (CRC Press, Inc., Boca Raton Fla., 1989).

Another key factor is the ability of antisense compounds to traverse the plasma membrane of specific cells involved in the disease process. Cellular membranes consist of lipid-protein bilayers that are freely permeable to small, nonionic, lipophilic compounds and inherently impermeable to most natural metabolites and therapeutic agents. Wilson, D. B. *Ann. Rev. Biochem.* 47:933–965 (1978). The biological and antiviral effects of natural and modified oligonucleotides in cultured mammalian cells have been well documented, thus it appears that these agents can penetrate membranes to reach their intracellular targets. Uptake of antisense compounds into a variety of mammalian cells, including HL-60, Syrian Hamster fibroblast, U937, L929, CV-1 and ATH8 cells has been studied using natural oligonucleotides and certain nuclease resistant analogues, such as alkyl triesters, Miller, P. S., Braiterman, L. T. and Ts'O, P. O. P., *Biochemistry* 16:1988–1996 (1977); methyl phosphonates, Marcus-Sekura, C. H., Woerner, A. M., Shinozuka, K., Zon, G., and Quinman, G. V., *Nuc. Acids Res.* 15:5749–5763 (1987) and Miller, P. S., McParland, K. B., Hayerman, K. and Ts'O, P. O. P., *Biochemistry* 16: 1988–1996 (1977) and Loke, S. K., Stein, C., Zhang, X. H. Avigan, M., Cohen, J. and Neckers, L. M. *Top. Microbiol. Immunol.* 141: 282:289 (1988).

Often, modified oligonucleotide and oligonucleotide analogues are less readily internalized than their natural counterparts. As a result, the activity of many previously available antisense oligonucleotides has not been sufficient for practical therapeutic, research or diagnostic purposes. Two other serious deficiencies of prior art oligonucleotides that have been designed for antisense therapeutics are inferior hybridization to intracellular RNA and the lack of a defined chemical or enzyme-mediated event to terminate essential RNA functions.

Modifications to enhance the effectiveness of the antisense oligonucleotides and overcome these problems have taken many forms. These modifications include base ring modifications, sugar moiety modifications and sugar-phosphate backbone modifications. Prior sugar-phosphate backbone modifications, particularly on the phosphorus atom, have effected various levels of resistance to nucleases. However, while the ability of an antisense oligonucleotide to bind to specific DNA or RNA with fidelity is fundamental to antisense methodology, modified phosphorus oligonucleotides have generally suffered from inferior hybridization properties.

Replacement of the phosphorus atom has been an alternative approach in attempting to avoid the problems associated with modification on the pro-chiral phosphate moiety. Some modifications in which replacement of the phosphorus atom has been achieved are; Matteucci, M. *Tetrahedron Letters* 31:2385–2388 (1990), wherein replacement of the phosphorus atom with a methylene group is limited by available methodology which does not provide for uniform insertion of the formacetal linkage throughout the backbone, and its instability, making it unsuitable for work; Cormier, et al. *Nucleic Acids Research* 16:4583–4594 (1988), wherein replacement of the phosphorus moiety with a diisopropylsilyl moiety is limited by methodology, solubility of the homopolymers and hybridization properties; Stirchak, et al. *Journal of Organic Chemistry* 52:4202–4206 (1987) wherein replacement of the phosphorus linkage by short homopolymers containing carbamate or morpholino linkages is limited by methodology, the solubility of the resulting molecule, and hybridization properties; Mazur, et al. *Tetrahedron* 40:3949–3956 (1984) wherein replacement of the phosphorus linkage with a phosphonic linkage has not been developed beyond the synthesis of a homotrimer molecule; and Goodchild, J., *Bioconjugate Chemistry* 1:165–187 (1990) wherein ester linkages are enzymatically degraded by esterases and are therefore unsuitable to replace the phosphate bond in antisense applications.

The limitations of the available methods for modification of the phosphorus backbone have led to a continuing and long felt need for other modifications which provide resistance to nucleases and satisfactory hybridization properties for antisense oligonucleotide diagnostics, therapeutics, and research.

OBJECTS OF THE INVENTION

It is an object of the invention to provide oligonucleotide analogues for use in antisense oligonucleotide diagnostics, research reagents, and therapeutics.

It is a further object of the invention to provide oligonucleotide analogues which possess enhanced cellular uptake.

Another object of the invention is to provide such oligonucleotide analogues which have greater efficacy than unmodified antisense oligonucleotides.

It is yet another object of the invention to provide methods for synthesis and use of such oligonucleotide analogues.

These and other objects will become apparent to persons of ordinary skill in the art from a review of the present specification and the appended claims.

SUMMARY OF THE INVENTION

Compositions useful for modulating the activity of an RNA or DNA molecule in accordance with this invention generally comprise oligonucleotide analogues having at least portions of their backbone linkages modified. In these modifications the phosphorodiester linkage of the sugar phosphate backbone found in natural nucleic acids has been replaced with various four atom linking groups. Such four atom linking groups maintain a desired four atom spacing between the 3'-carbon of one sugar or sugar analogue and the 4'-carbon of the adjacent sugar or sugar analogue. Oligonucleotide analogues made in accordance with the teachings of the invention are comprised of a selected sequence which is specifically hybridizable with a preselected nucleotide sequence of single stranded or double stranded DNA or RNA. They are synthesized conveniently, through known solid state synthetic methodology, to be complementary to or at least to be specifically hybridizable with the preselected nucleotide sequence of the RNA or DNA. Nucleic acid synthesizers are commercially available and their use is generally understood by persons of ordinary skill in the art as being effective in generating nearly any oligonucleotide or oligonucleotide analogue of reasonable length which may be desired.

In the context of this invention, the term "nucleoside" as the term is used in connection with this invention refers to the unit made up of a heterocyclic base and its sugar. The term "nucleotide" refers to a nucleoside having a phosphate group on its 3' or 5' sugar hydroxyl group. Thus nucleosides, unlike nucleotides, have no phosphate group. "Oligonucleotide" refers to a plurality of joined nucleotide units formed in a specific sequence from naturally occurring bases and pentofuranosyl groups joined through a sugar group by native phosphodiester bonds. These nucleotide units may be nucleic acid bases such as guanine, adenine, cytosine, thymine or uracil. The sugar group may be a deoxyribose or ribose. This term refers to both naturally occurring and synthetic species formed from naturally occurring subunits.

"Oligonucleotide analogue" as the term is used in connection with this invention, refers to moieties which function similarly to oligonucleotides but which have non-naturally occurring portions. oligonucleotide analogues may have altered sugar moieties, altered base moieties or altered inter-sugar linkages. For the purposes of this invention, an oligonucleotide analogue having non-phosphodiester bonds, i.e. an altered inter-sugar linkage, can alternately be considered as an "oligonucleoside." Such an oligonucleoside thus refers to a plurality of joined nucleoside units joined by linking groups other than native phosphodiester linking groups. Additionally for the purposes of this invention the terminology "oligomers" can be considered to encompass oligonucleotides, oligonucleotide analogues or oligonucleosides. Thus in speaking of "oligomers" reference is made to a series of nucleosides or nucleoside analogues that are joined together via either natural phosphodiester bonds or via other linkages including the four atom linkers of this invention. Generally while the linkage is from the 3' carbon of one nucleoside to the 5' carbon of a second nucleoside, the term "oligomer" can also include other linkages such as a 2'–5' linkage.

Oligonucleotide analogues may also comprise other modifications consistent with the spirit of this invention, and in particular such modifications as may increase nuclease resistance of the oligonucleotide composition in order to facilitate antisense therapeutic, diagnostic, or research reagent use of a particular oligonucleotide. For example, when the sugar portion of a nucleoside or nucleotide is replaced by a carbocyclic or other moiety, it is no longer a sugar. Moreover, when other substitutions, such a substitution for the inter-sugar phosphorodiester linkage are made, the resulting material is no longer a true nucleic acid species. All such are denominated as analogues, however. Throughout this specification, reference to the sugar portion of a nucleic acid species shall be understood to refer to either a true sugar or to a species taking the traditional space of the sugar of natural nucleic acids. Moreover, reference to inter-sugar linkages shall be taken to include moieties serving to join the sugar or sugar analogue portions together in the fashion of natural nucleic acids.

In accordance with the present invention, novel types of antisense oligonucleotide analogues and oligonucleosides are provided which are modified to enhance cellular uptake, nuclease resistance, and hybridization properties and to provide a defined chemical or enzymatically mediated event to terminate essential RNA functions.

It has been found that certain classes of oligonucleotide analogue compositions can be useful in therapeutics and for other objects of this invention. Such oligonucleotide analogues are comprised of subunits, at least some of which have the structure:

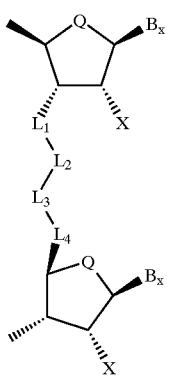

wherein $B_x$ is a variable base moiety; Q is O, $CH_2$, CHF or $CF_2$ and X is H; OH; $C_1$ to $C_{10}$ lower alkyl, substituted lower alkyl, alkaryl or aralkyl; F; Cl; Br; CN; $CF_3$; $OCF_3$; OCN; O—, S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino or substituted silyl. Moreover, X can be an RNA cleaving group; a group for improving the pharmacokinetic properties of an oligonucleotide; or a group for improving the pharmacodynamic properties of an oligonucleotide.

$L_1$ and $L_4$ are, independently, $CH_2$, C=O, C=S, C—$NH_2$, C—$NHR_3$, C—OH, C—SH, C—O—R, or C—S—$R_1$. $L_2$ and $L_3$ are, independently, $CR_1R_2$, C=$CR_1R_2$, C=$NR_3$, $P(O)R_4$, $P(S)R_4$, C=O, C=S, O, S, SO, $SO_2$, $NR_3$ or $SiR_5R_6$; or together, form part of an alkene, alkyne, aromatic ring, carbocycle or heterocycle. $L_1$, $L_2$, $L_3$ and $L_4$ are as noted with the proviso that if $L_1$ is C=O or C=S then $L_2$ is not $NR_3$ or if $L_4$ in C=O or C=S then $L_3$ is not $NR_3$. Further $L_1$, $L_2$, $L_3$ and $L_4$, together, may comprise a —CH=N—NH—$CH_2$— or —$CH_2$—O—N=CH— moiety.

$R_1$ and $R_2$ are, independently, H; OH; SH; $NH_2$; $C_1$ to $C_{10}$ alkyl, substituted alkyl, alkenyl, alkaryl or aralkyl; alkoxy; thioalkoxy; alkylamino; aralkylamino; substituted alkylamino; heterocycloalkyl; heterocycloalkylamino; aminoalkylamino; polyalkylamino; halo; formyl; keto; benzoxy; carboxamido; thiocarboxamido; ester; thioester; carboxamidine; carbamyl; ureido or guanidino. They may also independently comprise an RNA cleaving group; a group for improving the pharmacokinetic properties of an oligonucleotide; or a group for improving the pharmacodynamic properties of an oligonucleotide;

$R_3$ is H, OH, $NH_2$, lower alkyl, substituted lower alkyl, alkoxy, lower alkenyl, aralkyl, alkylamino, aralkylamino, substituted alkylamino, heterocycloalkyl, heterocycloalkylamino, aminoalkylamino, polyalkylamino, an RNA cleaving group, a group for improving the pharmacokinetic properties of an oligonucleotide or a group for improving the pharmacodynamic properties of an oligonucleotide. $R_4$ is OH, SH, $NH_2$, O-alkyl, S-alkyl, NH-alkyl, O-alkylheterocyclo, S-alkylheterocyclo, N-alkylheterocyclo or a nitrogen-containing heterocycle.

$R_5$ and $R_6$ are, independently, $C_1$ to $C_6$ alkyl or alkoxy; provided that if $L_2$ is $P(O)R_4$ and $R_4$ is OH and X is OH and $B_x$ is uracil or adenine, then $L_3$ is not O; and that if $L_1$, $L_2$ and $L_4$ are $CH_2$ and X is H or OH and Q is O then $L_3$ is not S, SO or $SO_2$.

In accordance with preferred embodiments, the oligonucleotide analogues of the invention comprise sugar moieties, such that Q is O. In accordance with other embodiments, each of $L_1$ and $L_4$ is $CR_1R_2$. It is also preferred that $L_2$ and $L_3$ be, independently, $CR_1R_2$, O, $P(O)R_4$, $P(S)R_4$ or $NR_3$ and especially that one of $L_2$ and $L_3$ be $CR_1R_2$ and the other of $L_2$ and $L_3$ be $P(O)R_4$ or $P(S)R_4$. Combinations where $L_2$ is O and $L_3$ is $P(O)R_4$ or $P(S)R_4$ are also preferred.

In accordance with other preferred embodiments, the oligonucleotide analogues of this invention are such that each of $L_2$ and $L_3$ is $NR_3$ where $R_3$ is preferably H. Alternatively, the analogues of the invention may be such that $L_2$ and $L_3$, taken together, form a portion of a cyclopropyl, cyclobutyl, ethyleneoxy, ethyl aziridine or substituted ethyl aziridine ring. $L_2$ and $L_3$ taken together may also form a portion of a $C_3$ to $C_6$ carbocycle or 4-, 5- or 6-membered nitrogen heterocycle.

It is preferred that the oligonucleotide analogues be such that X is H or OH, or, alternatively F, O-alkyl or O-alkenyl, especially where Q is O. The group $B_x$ is preferably adenine, guanine, uracil, thymine, cytosine, 2-aminoadenosine or 5-methylcytosine, although other non-naturally occurring species may be employed.

Other preferred embodiments are those where $L_1$ and $L_4$ are each $CH_2$, especially where $L_2$ and $L_3$ are each NH. Alternatively, one of $L_2$ and $L_3$, preferably, $L_3$, is O and the other of $L_2$ and $L_3$ is NH.

It is preferred that the oligonucleotide analogues of the invention comprise from about 5 to about 50 subunits having the given structure. While substantially each subunit of the oligonucleotide analogues may have said structure, it is also desirable for substantially alternating subunits to have said structure.

The oligonucleotide analogues of this invention are preferably prepared in a pharmaceutically acceptable carrier for therapeutic administration to patients. The analogues are believed to exhibit improved nuclease resistance as compared to corresponding natural oligonucleotides.

This invention is also directed to methods for modulating the production or activity of a protein in an organism comprising contacting the organism with an oligonucleotide analogue specifically hybridizable with at least a portion of a nucleic acid sequence coding for said protein, wherein at least some of the subunits of the analogue have the foregoing structure.

Additionally, the invention is directed to methods for treating an organism having a disease characterized by the undesired production of a protein comprising contacting the organism with an oligonucleotide analogue hybridizable with at least a portion of a nucleic acid sequence coding for said protein, either alone or in a pharmaceutically acceptable carrier, wherein at least some of the subunits of the analogue have the given structure.

This invention also provides methods for synthesizing oligonucleotide analogues including those useful in the practice of the therapeutic methods of the invention comprising providing a first moiety comprising the structure:

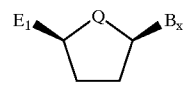

and a second moiety comprising the structure:

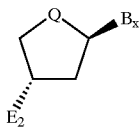

wherein $B_x$ is a variable base moiety; Q is O, $CH_2$, CHF or $CF_2$; and $E_1$ and $E_2$ are the same or different and are electrophilic reactive groups; and coupling said first and second moieties with a linking group through said electrophilic reactive groups to form said oligonucleotide analogue. In accordance with preferred methods, the electrophilic reactive group of the first moiety comprises halomethyl, trifluoromethyl, sulfonylmethyl, p-methyl-benzene sulfonyl-methyl, or 3'-C-formyl, while the electrophilic reactive group of the second moiety comprises halogen, sulfonylmethyl, p-methyl-benzene sulfonyl methyl, or aldehyde. It is preferred that the linking group be hydrazine or hydroxylamine.

The invention also provides a method of protecting the $L_2$ or $L_3$ nitrogen moiety of an oligonucleotide analogue as described above wherein one of $L_2$ or $L_3$ is $NR_3$ and $R_3$ is H. This method includes blocking the nitrogen moiety with phenoxyacetylchloride, further reacting the oligonucleotide analogue to modify the oligonucleotide and deblocking the nitrogen moiety with ammonium hydroxide.

The invention also provides a method of protecting a bifunctional nucleoside or oligonucleotide analogue wherein one of the bifunctionalities is an aldehyde. This method includes reacting the aldehyde with methoxyamine to form an oxime derivative of the aldehyde, further reacting the nucleoside or oligonucleoside analogue to modify the nucleoside or oligonucleotide analogue and reacting the oxime with an acetaldehyde to regenerate the aldehyde.

The invention also provides a method of synthesizing an oligonucleotide analogue as described above wherein the method includes generating a radical at the 3' carbon atom of a pentofuranosyl nucleoside and reacting that radical with an oxime moiety that is pendent on the 5' position of a further pentofuranosyl nucleoside.

It is useful to formulate therapeutic compositions where at least one portion of said oligonucleotide analogue is incorporated into a further oligonucleotide species to provide said further oligonucleotide analogue with natural phosphodiester bonds substantially alternating with areas so coupled. The incorporation is preferably achieved by phosphodiester linkage of a desired sequence of dinucleotides, said dinucleotides having been previously so coupled.

Precursor nucleosides are also contemplated by this invention having the structure:

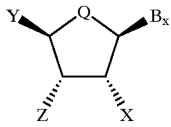

wherein $B_x$ is a variable base moiety Q is O, $CH_2$, CHF or $CF_2$; and X is H; OH; $C_1$ to $C_{10}$ lower alkyl, substituted lower alkyl, alkaryl or aralkyl; F; Cl; Br; CN; $CF_3$; $OCF_3$; OCN; O—, S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a group for improving the pharmacokinetic properties of an oligonucleotide; or a group for improving the pharmacodynamic properties of an oligonucleotide.

In such species, Y is hydroxyl, aminomethyl, hydrazinomethyl, hydroxymethyl, C-formyl, phthalimidohydroxymethyl, aryl-substituted imidazolidino, aminohydroxylmethyl, ortho-methylaminobenzenethio, methylphosphonate and methyl-alkylphosphonate. Z is H, hydroxyl, aminomethyl, hydrazinomethyl, hydroxymethyl, C-formyl, phthalimidohydroxymethyl, aryl substituted imidazolidino, aminohydroxylmethyl, ortho-methylaminobenzenethio, methylphosphonate or methyl alkylphosphonate.

All of the foregoing is with the proviso that when Q is O and Y is hydroxymethyl and X is H or OH then Z is not H or C-formyl; and that when Q is O and X is H or OH and Z is hydroxyl then Y is not aminohydroxylmethyl, hydrazinomethyl or aryl-substituted imidazolidino. It is preferred that X be H or OH and that Q be O.

Oligonucleotide analogues having modified sugar linkages have been found to be effective in accomplishing these goals. The oligonucleotide analogues may preferably range in size from about 5 to about 50 nucleic acid base subunits in length. Oligonucleotide analogues described in this invention are hybridizable with preselected nucleotide sequences of single stranded or double stranded DNA and RNA. The nucleic acid bases which comprise this invention may be pyrimidines such as thymine, uracil or cytosine or purines such as guanine or adenine, or modifications thereof such as 5-methylcytosine, arranged in a selected sequence. The sugar moiety may be of the ribose or deoxyribose type or a sugar mimic such as a carbocyclic ring. In accordance with one preferred embodiment of this invention, the oligonucleotide analogues or oligonucleosides hybridize to HIV mRNA encoding the tat protein, or to the TAR region of HIV mRNA. In another preferred embodiment, the oligonucleotide analogues or oligonucleosides mimic the secondary structure of the TAR region of HIV mRNA, and by doing so bind the tat protein. Other preferred antisense oligonucleotide analogue or oligonucleoside sequences include complementary sequences for herpes, papilloma and other viruses.

The modified linkages of this invention preferably are comprised of a four atom linking group to replace the naturally occurring phosphodiester-5'-methylene linkage. Replacement of the naturally occurring linkage by four atom linkers of the present invention confers nuclease resistance and enhanced cellular uptake upon the resulting oligonucleotide analogue. Included within the four atom linker is preferably a 3'-deoxy function on one of the linked sugars. The four atom linker is of the structure —$L_1$—$L_2$—$L_3$—$L_4$— wherein $L_1$ and $L_4$ are methylene carbon atoms or substituted carbon atoms and $L_2$ and $L_3$ are methylene carbon atoms, substituted carbon atoms, oxygen atoms, nitrogen or substituted nitrogen atoms, substituted phosphorus atoms, sulfur or substituted sulfur atoms or substituted silicon atoms. It is preferred that the modified linkage occur at substantially each linkage location. Alternatively, modification may occur at less than every location such as at alternating linkage locations. The linkage may be neutral or may be positively or negatively charged.

This invention is also directed to methods for synthesizing such oligonucleosides. The invention provides for the coupling of a 3'-deoxy-3'-substituted, especially methyl substituted, nucleoside with a 5'-deoxy-5'-substituted nucleoside through the addition of a two atom fragment or substituted two atom fragment. The addition reaction may occur through a stepwise procedure involving the activation of the 3' and 5' positions of respective nucleosides to a variety of suitable electrophilic moieties, followed by the addition of a suitable linking group to react with the electrophiles. In the alternative, the procedure may occur in a concerted manner. Such methods may employ solid supports via a DNA synthesizer, by manual manipulation of the support, or otherwise.

This invention is also directed to methods for modulating the production of proteins by an organism comprising contacting the organism with a composition formulated in accordance with the foregoing considerations. It is preferred that the RNA or DNA portion which is to be modulated be preselected to comprise that portion of DNA or RNA which codes for the protein whose formation or activity is to be modulated. The targeting portion of the composition to be employed is, thus, selected to be complementary to the preselected portion of DNA or RNA, that is to be an antisense oligonucleotide for that portion.

This invention is also directed to methods for treating an organism having a disease characterized by the undesired production of a protein. This method comprises contacting the organism with a composition in accordance with the foregoing considerations. The composition is preferably one which is designed to specifically bind with messenger RNA which codes for the protein whose production or activity is to be modulated. The invention further is directed to diagnostic methods for detecting the presence or absence of abnormal RNA molecules or abnormal or inappropriate expression of normal RNA molecules in organisms or cells.

This invention is also directed to methods for the selective binding of RNA for research and diagnostic purposes. Such selective, strong binding is accomplished by interacting such RNA or DNA with compositions of the invention which are resistant to degradative nucleases and which hybridize more strongly and with greater fidelity than known oligonucleotides or oligonucleotide analogues.

DETAILED DESCRIPTION OF PREFERRED EMBODIMENTS

Figure 1:
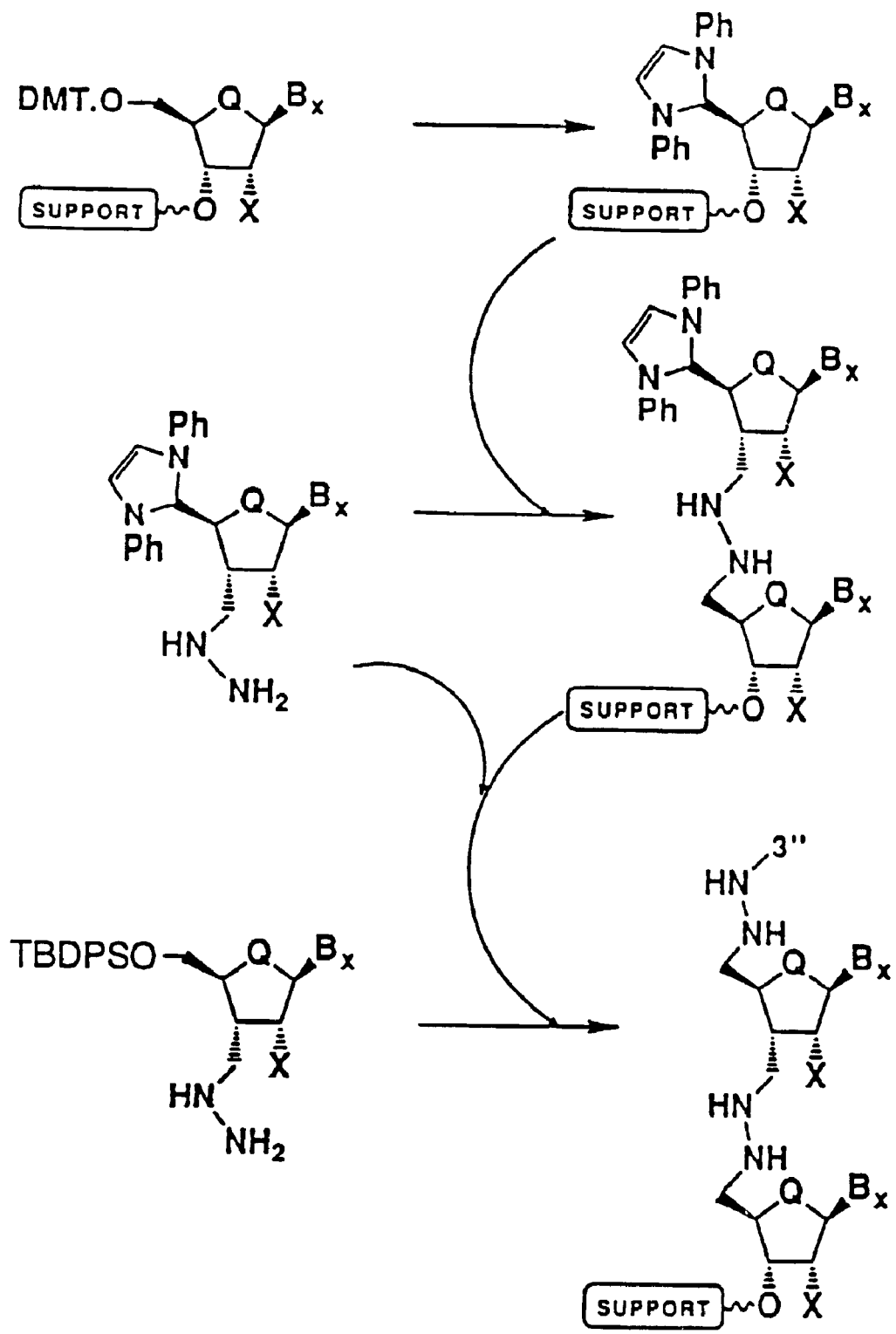
FIG. 1 is a schematic, synthetic scheme in accordance with certain embodiments of the invention.

The biological activity of the antisense oligonucleotides previously available has not generally been sufficient for practical therapeutic research or diagnostic use. This invention directs itself to modified oligonucleotides, i.e. oligonucleotide analogues or oligonucleosides, and methods for effecting such modifications. These modified oligonucleotides and oligonucleotide analogues exhibit increased stability relative to their naturally occurring counterparts. Extracellular and intracellular nucleases generally do not recognize and therefore do not bind to the backbone modified oligonucleotide analogues or oligonucleosides of the present invention. Any binding by a nuclease to the backbone will not result in cleavage of the nucleosidic linkages due to the lack of sensitive phosphorus-oxygen bonds. In addition, the, resulting, novel neutral or positively charged backbones of the present invention may be taken into cells by simple passive transport rather than requiring complicated protein mediated processes. Another advantage of the present invention is that the lack of a negatively charged backbone facilitates the sequence specific binding of the oligonucleotide analogues or oligonucleosides to targeted RNA, which has a negatively charged backbone, and which will accordingly repel incoming similarly charged oligonucleotides. Still another advantage of the present invention is that sites for attaching functional groups which can initiate catalytic cleavage of targeted RNA are found in these structure types.

In accordance with preferred embodiments, this invention is directed to replacing inter-sugar phosphate groups to yield analogues having linkages as found in the structure:

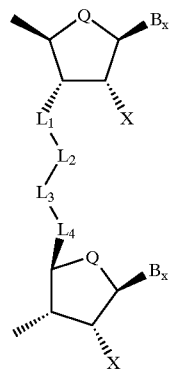

wherein
$B_x$ is a variable base moiety;
Q is O, $CH_2$, CHF or $CF_2$;
X is H; OH; $C_1$ to $C_{10}$ lower alkyl, substituted lower alkyl, alkaryl or aralkyl; F; Cl; Br; CN; $CF_3$; $OCF_3$; OCN; O—, S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a group for improving the pharmacokinetic properties of an oligonucleotide; or a group for improving the pharmacodynamic properties of an oligonucleotide;
$L_1$ and $L_4$ are, independently, $CH_2$, C=O, C=S, C—$NH_2$, C—$NHR_3$, C—OH, C—SH, C—O—$R_1$ or C—S—$R_1$; and
$L_2$ and $L_3$ are, independently, $CR_1R_2$, C=$CR_1R_2$, C=$NR_3$, P(O)$R_4$, P(S)$R_4$, C=O, C=S, O, S, SO, $SO_2$, $NR_3$ or $SiR_5R_6$; or, together, form part of an alkene, alkyne, aromatic ring, carbocycle or heterocycle; or
$L_1$, $L_2$, $L_3$ and $L_4$, together, comprise a —CH=N—NH—$CH_2$— or —$CH_2$—O—N=CH— moiety;
$R_1$ and $R_2$ are, independently, H; OH; SH; $NH_2$; $C_1$ to $C_{10}$ alkyl, substituted alkyl, alkenyl, alkaryl or aralkyl; alkoxy; thioalkoxy; alkylamino; aralkylamino; substituted alkylamino; heterocycloalkyl; heterocycloalkylamino; aminoalkylamino; polyalkylamino; halo; formyl; keto; benzoxy; carboxamido; thiocarboxamido; ester; thioester; carboxamidine; carbamyl; ureido; guanidino; an RNA cleaving group; a group for improving the pharmacokinetic properties of an oligonucleotide; or a group for improving the pharmacodynamic properties of an oligonucleotide;
$R_3$ is H, OH, $NH_2$, lower alkyl, substituted lower alkyl, alkoxy, lower alkenyl, aralkyl, alkylamino, aralkylamino, substituted alkylamino, heterocycloalkyl, heterocycloalkylamino, aminoalkylamino, polyalkylamino, an RNA cleaving group, a group for improving the pharmacokinetic properties of an oligonucleotide and a group for improving the pharmacodynamic properties of an oligonucleotide;

$R_4$ is OH, SH, $NH_2$, O-alkyl, S-alkyl, NH-alkyl, O-alkylheterocycle, S-alkylheterocycle, N-alkylheterocycle or a nitrogen-containing heterocycle; and $R_5$ and $R_6$ are, independently, $C_1$ to $C_6$ alkyl or alkoxy; provided that if $L_1$ is C=O or C=S then $L_2$ is not $NR_3$ or if $L_4$ is C=O or C=S then $L_3$ is not $NR_3$; and that if one of $L_2$ or $L_3$ is C=O or C=S then the other of $L_2$ or $L_3$ is not $NR_3$; and that if $L_2$ is $P(O)R_4$ and $R_4$ is OH and X is OH and $B_x$ is uracil or adenine, then $L_3$ is not O; and that if $L_1$, $L_2$ and $L_4$ are $CH_2$ and X is H or OH and Q is O then $L_3$ is not S, SO or $SO_2$.

In accordance with preferred embodiments of the invention, $L_1$ and $L_4$ are methylene groups. In such preferred embodiments one of $L_2$ or $L_3$ can comprise an amino group and the other comprise an amino group or an oxygen. Thus in certain preferred embodiments $L_2$ and $L_3$ together are hydrazino, aminohydroxy or hydroxyamino. In other preferred embodiments one of $L_1$ or $L_4$ together with one of $L_2$ or $L_3$ are a CH=N group and the other of $L_2$ or $L_3$ is an oxygen or nitrogen atom thus the linker includes oxime and hydrazone groupings, respectively. Such oxime or hydrazone linking groups can be reduced to the above referenced aminohydroxy or hydrazine groups.

In other preferred embodiments of the present invention, $L_2$ and $L_3$ are substituted carbon, amino, substituted amine, oxygen, sulfur, oxides of sulfur, phosphorus or silicon. The substituents on carbon include hydrogen, hydroxy, thio, amino, lower alkyl, substituted lower alkyl, alkoxy, thioalkoxy, lower alkenyl, aralkyl, alkylamino, aralkylamino, substituted alkylamino, heterocycloalkyl, heterocycloalkylamino, aminoalkylamino, polyalkylamino, halogen, formyl, keto, benzoxy, ester, thioester, carboxamidine, guanidino, an RNA cleaving group, a group for improving the pharmacokinetic properties of an oligonucleotide or a group for improving the pharmacodynamic properties of an oligonucleotide. Additional preferred embodiments include $L_2$ and $L_3$ together being C=C. Further preferred embodiments include $L_2$ and $L_3$ together being a C—C, C=C, C—N or N—C two atom pair of a ring structure including carbocyclic, aromatic, heteroaromatic or heterocyclic rings. Still another preferred embodiment of the present invention provides that $L_1$ and $L_4$ independently are carboxy, thiocarboxy, methylamino, methylhydroxy, methylthio, ether or thioether.

The invention is also directed to methods for the preparation of oligonucleosides with modified inter-sugar linkages. These modifications may be effected using solid supports which may be manually manipulated or used in conjunction with a DNA synthesizer using methodology commonly known to those skilled in DNA synthesizer arts. Generally, the procedure involves functionalizing the sugar moieties of two nucleosides which will be adjacent to one another in the selected sequence. In a 5' to 3' sense, the "upstream" nucleoside is generally modified at the 3' sugar site and is referred to hereinafter as "synthon 1". In one process of the invention ribo- and 2'-deoxyribonucleosides of adenine, guanine, cytosine, uracil, thymine and their analogues are modified to give their 3'-deoxy-3-hydroxymethyl analogues. These 3'-hydroxymethyl groups are then converted into various types of electrophilic centers. This may be accomplished in a number of ways such as the following, preferred scheme.

One class of starting materials, 3'-deoxy-3'-hydroxymethyl ribonucleosides, can be prepared as described by Townsend et al., *Tetrahedron Letters*, 31:3101–3104 (1990), Samano, V. and M. J. Morris, *Journal of Organic Chemistry*, 55:5186–5188 (1990) and Bergstrom, D. E., *Nucleosides and Nucleotides* 8(8): 1529–1535 (1989). Appropriate, known, selective sugar hydroxyl protection of these nucleosides followed by standard 2'-deoxygenation procedures will afford the 2',3'-dideoxy-3'-hydroxymethyl-ribonucleosides. Nucleosides of this type can be selectively protected and the 3'-hydroxymethyl moiety functionalized to a variety of suitable electrophilic moieties. In accordance with preferred embodiments of this invention, such electrophilic moieties include halomethyl, trifluoromethyl, sulfonylmethyl, p-methylbenzene sulfonylmethyl, hydrazinomethyl or 3'-C-formyl.

The "downstream" nucleoside is generally modified at the 5' sugar site and is referred to hereinafter as "synthon 2". Modification to produce ribo and 2'-deoxyribonucleosides of adenine, guanine, cytosine, uracil, thymine and their analogues, with their 5'-hydroxymethylene group converted into various types of electrophilic centers can be accomplished through various procedures using commercially available nucleosides. For example, 5'-deoxy-5'-halo nucleoside, 5'-deoxy-5'-tosyl nucleosides, and 5'-aldehydic nucleosides have been prepared by Jones, G. H. and J. G. Moffatt in *Journal of the American Chemical Society* 90:5337–5338 (1968).

In general, synthon 1 may be represented as comprising the structure:

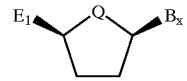

while synthon 2 generally comprises the structure:

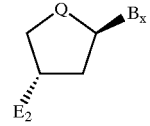

wherein $B_x$ is a variable base moiety; Q is O, $CH_2$, CHF or $CF_2$; and $E_1$ and $E_2$ are the same or different and are electrophilic reactive groups.

The two synthons are coupled via a linking group reactive with the electrophilic reactive groups or otherwise. Coupling between synthon 1 and synthon 2 may occur either stepwise or in a concerted manner and may result in dinucleosides linked through the modified linkage of the present invention or may result in a chain of nucleosides, each of which may be linked to the next through said modified linkage.

Coupling via a concerted action may occur between the electrophilic centers of synthon 1 and synthon 2 such as in the presence of ammonia or an ammonia derivative to produce a dinucleoside. A preferred embodiment of the present invention is the coupling of known, bromomethyl type synthons by the addition of hydrazine to produce a preferred linkage having —$L_1$—$L_2$—$L_3$—$L_4$— equal to —$CH_2NHNHCH_2$—. Another preferred embodiment of the present invention is the coupling of bromomethyl type synthons by the addition of hydroxylamine to produce a linkage having —$L_1$—$L_2$—$L_3$—$L_4$— equal to —$CH_2NHOCH_2$— or —$CH_2ONHCH_2$—.

Another procedure whereby inter-sugar linkages may be modified to provide the dinucleoside structure described herein is via a Wittig reaction. Preferably, the starting material of such reaction is a 3'-keto nucleoside such as described by Townsend, et al. in *Tetrahedron Letters* 31:3101–3104 (1990); Samano, V. and M. J. Morris in

*Journal of Organic Chemistry* 55:5186–5188 (1990); and Bergstrom, D. E., et al. in *Nucleosides and Nucleotides* 8(8):1529–1535 (1989); or a 5'-aldehydic nucleoside as described by Jones, G. H. and J. G. Moffatt in *Journal of the American Chemical Society* 90:5337–5338 (1968). The starting material is preferably reacted with a phosphorus ylide having a benzyl or other protecting group. One preferred ylide useful for this invention is triphenylphosphorane-benzyloxymethylidine. Another useful ylide preferably used for this invention is triphenylphosphorane-benzyloxyethylidine. Reduction of the vinyl group and hydrogenolysis of the benzyl protecting group provides hydroxymethyl and hydroxyethyl moieties respectively, in the 5' or 3' positions of the desired nucleoside of guanine, adenine, cytosine, thymine, uracil or the analogues of these nucleosides. In addition, the Wittig reaction may be used to provide the 5' and 3' hydroxy alkyl moieties of carbocyclic nucleosides.

Conversion of the hydroxyl groups to provide electrophilic centers and subsequent coupling of a 3' electrophilic center with a 5' electrophilic center will afford dinucleosides of the present invention. In one embodiment of the invention, the hydroxyl groups are converted to provide electrophilic centers such as bromides, triflates, and tosylates. Coupling affords dinucleosides connected by a carbon chain with one or two heteroatoms. Preferably such heteroatoms may be O, NH, $NR_3$, S, SO, $SO_2$, $P(O)R_4$, $P(S)R_4$ or $SiR_5R_6$ as depicted in the generic formula provided previously.

Other useful dinucleosides which likely may be derived from a Wittig reaction involving 3' or 5' carbonyl nucleosides and triphenylphosphorine methylidine diphenylphosphonate are phosphonate dinucleosides. This reaction provides the methyl or ethyl phosphonate which can be condensed with the corresponding 5'- or 3'-hydroxy group to provide 3'- or 5'-phosphonate linked oligonucleosides. Chemistry of this type has been described in the preparation of phosphonates of dinucleosides for the study of biochemical processes, Moffatt, J. G., et al., *Journal of American Chemical Society* 92:5510–5513 (1970) and Mazur, A., B.E. Tropp, and R. Engel, *Tetrahedron* 40:3949–3956 (1984). Utilizing this type of coupling a preferred embodiment is prepared by the coupling a 3'-keto nucleoside to a 5'-nucleoside with a symmetrical bis(methyltriphenylphosphane)phenylphosphate to provide 3',5'-dimethylphosphonate linked oligonucleotides.

In addition to the Wittig reaction, 3'-hydroxymethyl nucleosides may also be prepared through the inversion of alpha carbocyclic nucleosides. This will provide the desired 3' hydroxymethyl group on the "down" or alpha face. This group can now be protected and the 3"-hydroxyl group (identifying the exo-cyclic methyl linked to the sugar 3' position as 3" methyl) can be converted to an hydroxymethyl or longer alkyl group. One method of converting the 3" group involves oxidation to the keto group followed by a Wittig reaction with triphenylphosphorine methylidine diphenylphosphonate and reduction. Longer hydroxyalkyl groups can be placed in the 3"-position in this manner. This embodiment also provides a 4'-desmethyl-3'-hydroxymethyl nucleoside synthon. Coupling between this 4'-desmethyl and the normal 3'-hydroxy-nucleoside with a two atom coupler will provide dinucleoside synthons as described in prior pending application (Ser. No. 566,836 filed Aug. 13, 1990, now U.S. Pat. No. 5,223,618, which is assigned to the assignee of this application). Coupling of the 4'-desmethyl hydroxyl group with appropriate 3'-synthons as described above will provide a number of other types of novel dinucleoside synthons.

Yet another approach to functionalize the methyl group of 3'-deoxy-3'-methyl nucleosides may be elaborated from 3'-deoxy-3'-cyanonucleosides. Parkes, K. E. B., and K. Taylor, *Tetrahedron Letters* 29:2995–2996 (1988) described a general method of synthesis of 3'-cyano nucleosides. In this method, 5'-trityl protected 2'-deoxynucleosides are 3'-iodinated with methyltriphenylphosphonium iodide. These materials are then treated with hexamethylditin, t-butylisonitrile, and 2,2'-azo-bisisobutrylonitrile (AIBN) to provide the radical addition of a cyano group to the 3'-position. Conversion of the cyano group to the aldehyde was accomplished in high yield. Subsequently, the intermediate was converted to hydroxymethyl functions which are valuable precursors to the electrophilic synthon 1.

An additional procedure whereby inter-sugar linkages may be modified to provide dinucleosides utilizes 3'-C-formyl derivatized nucleosides as synthon 1 and 5'-aminohydroxy derivatized nucleosides as synthon 2. Direct coupling of synthons 1 and 2 gave a dinucleoside coupled via an oxime linkage. In this instance the oxime is present as E/Z isomers. The isomeric compounds are separated utilizing HPLC. Further in this instance the oxime nitrogen atom is adjacent to a carbon atom on the 3' end of the upstream nucleoside. Dinucleosides having the oxime nitrogen adjacent to a carbon atom on the 5' or downstream nucleoside are synthesized utilizing a 5'-C-formyl derivatized nucleoside as synthon 2 and a 3'-deoxy-3'-aminohydroxymethyl derivatized nucleoside as synthon 1. In this instance oxime E/Z isomers are also obtained. In both instances the oxime linked dimers are useful for direct incorporation into an oligomer or then can be reduced to the corresponding hydroxyamino linked dinucleoside. Reduction of oxime linked dinucleosides either as the dinucleoside or as a dinucleoside moiety in an oligomer with sodium cyanoborohydride yields the corresponding aminohydroxyl linked compounds. The hydroxyamino linked dinucleoside or a large oligomer could be alkylated at the amino moiety of the aminohydroxyl linkage to yield a corresponding N-alkylamino linkage.

The 3'-C-formyl derivatized synthon 1 can be formed via several synthetic pathways. The presently preferred method utilizes a radical carbonylation of the corresponding 3'-deoxy-3'-iodo nucleoside. The iodo compound is treated with CO, AIBN, i.e. 2,2'-azobisisobutrylnitrile, and TTMS, i.e. tris(trimethylsilyl)silane. Alternately it can be synthesized from either a 3'-deoxy-3'cyano sugar or nucleoside. Both 5'-C-formyl (also identified as 5'-aldehydo) and 3'-C-formyl group can be blocked in a facile manner utilizing o-methylaminobenzenthiol as a blocking group. Both of the 5' and the 3'-C-formyl groups can be deblocked with silver nitrate oxidation.

In an alternate method of 3'-C-formyl nucleoside synthesis, 1-O-methyl-3'-deoxy-3'-O-methylaminobenzene thiol-5'-O-trityl-β-D-erythro-pento furanoside can be used for its preparation. This compound then serves as a precursor for any 3'-deoxy-3'-C-formyl nucleoside. The 1-O-methyl-3'-deoxy-3'-O-methyl amino benzenethiol-5'-O-trityl-β-D-erythro-pentofuranoside is reacted with an appropriate base utilizing standard glycosylation conditions followed by deblocking to yield the nucleoside. In even a further alternate method a 3'-deoxy-3'-cyano nucleoside is prepared from either the corresponding 3'-deoxy-3'-iodo nucleoside or via a glycosylation reaction with 1-O-methyl-3'-deoxy-3'-O-cyano-5'-O-trityl-β-D-erythro-pentofuranoside.

The 3"-O-amino-3"-hydroxymethyl nucleoside and the corresponding 5'-O-amino nucleoside can be conveniently prepared via a protected phthalimido intermediate via Mitsunobu conditions using N-hydroxyphthalimide, triphenylphosphine and diisopropylazodicarboxylate. This in turn is prepared by a Mitsunobu reaction on the unprotected hydroxyl group of the nucleoside. In forming the 3"-O-amino-3"-hydroxymethyl nucleoside, trityl serves as a blocking group for the 5'-hydroxyl group of the nucleoside. For both purine and pyrimidine nucleosides prior to reacting with N-hydroxyphthalimide the 3'-hydroxy group is protected with TBDPS. With pyrimidine bases, in forming the 5'-O-amino nucleoside the 3'-hydroxyl can be protected with TBDPS blocking groups after introduction of the phthalimido on the 5' position.

A further procedure whereby inter-sugar linkages may be modified to provide phosphonate linked dinucleotides utilizes the Michaelis-Arbuzov procedure of Mazur et al., *Tetrahedron*, 20:3949 (1984) for formation of 3'-C-phosphonate dimers. This procedure would utilize a 3'-hydroxymethyl nucleosides as synthon 1. This is treated with N-bromosuccinimide to yield the corresponding 3"-bromomethyl derivative. Synthon 2 is selected as a 5'-phosphite. Coupling of synthons 1 and 2 gives a dinucleoside coupled via a 3'-C-phosphonate linkage. The corresponding 5'-C-phosphonate dimers could be obtained by first reacting a suitable blocked phosphite with synthon 1 followed by deblocking to yield the 3'-CH$_2$-phosphite intermediate. Synthon 2 is selected as a 5'-bromonucleoside. The 3'-CH$_2$-phosphite intermediate is then reacted with synthon 2 to give the 5'-C-phosphate dimer. By selecting tribenzylphosphite as the blocked phosphite after coupling to synthon 1 the benzyl groups can be removed by hydrogenolysis. Alternately a 5'-deoxy-5'-bromonucleoside is reacted with a phosphite ester resulting in a 5'-phosphonate. This in turn is reacted with 3'-hydroxymethyl nucleoside to yield the 5'-C-phosphonate linked dimer.

Resulting dinucleosides from any of the above described methods, linked by hydrazines, hydroxyl amines and other linking groups of the inventions, can be protected by a dimethoxytrityl group at the 5'-hydroxyl and activated for coupling at the 3'-hydroxyl with cyanoethyldiisopropylphosphite moieties. These dimers may be inserted into any desired sequence by standard, solid phase, automated DNA synthesis utilizing phosphoramidite coupling chemistries. Therefore, the protected dinucleosides are linked with the units of a specified DNA sequence utilizing normal phosphodiester bonds. The resulting oligonucleotide analogue or oligomer has a mixed backbone—part normal phosphodiester links and part novel four atoms links of the inventions. In this manner, a 15-mer, sequence-specific oligonucleotide can easily be synthesized to have seven hydroxylamine, hydrazine or other type linked dinucleosides. Such a structure will provide increased solubility in water compared to native phosphodiester linked oligonucleotides.

Oligonucleosides containing an uniform backbone linkage can be synthesized by use of CPG-solid support and standard nucleic acid synthesizing machines, i.e., Applied Biosystems Inc. 380B and 394 and Milligen/Biosearch 7500 and 8800 s. The initial nucleoside (number 1 at the 3'-terminus) is attached to a solid support such as controlled pore glass and in sequence specific order each new nucleoside is attached either by manual manipulation or by the automated synthesizer system. In the case of a methylene-hydrazine linkage, the repeating nucleoside unit can be of two general types, e.g., a nucleoside with a 5'-protected aldehydic function and a 3'-deoxy-3'-C-hydrazinomethyl group, or a nucleoside bearing a 5'-deoxy-5'-hydrazino group protected by an acid labile group and a 3'-deoxy-3'-C-formyl group. In each case, the conditions which are repeated for each cycle to add the subsequent sequence required base include: acid washing to remove the 5'-aldehydo protecting group; addition of the next nucleoside with a 3'-methylenehydrazino group to form the respective hydrazone connection; and reduction with any of a variety of agents to afford the desired methylene-hydrazine linked CPG-bound oligonucleosides. One such useful reducing agent is sodium cyanoborohydride.

A preferred method is depicted in FIG. 1. This method employs a solid support on which a synthon 2 with a protected 5' site is bound. Preferably, the 5' site of said synthon may be protected with DMT. Thereafter, the 5' site of the synthon 2 is liberated with mild acid, washed, and oxidized to produce an intermediate product. In one preferred method, the aldehyde derivative reacts with N,N-diphenylethylene diamine to produce an intermediary product, 5'-diphenylimidazolidino protected synthon 2. In a more preferred method the 5'-diphenylimidazolidino protected synthon 2 is directly loaded on the support. With either method the intermediary product may be subsequently deblocked to provide a synthon 2 with a nucleophilic 5' position. Addition of a synthon 1 with a protected 5'-aldehyde group, such as a 5'-diphenylimidazolidino protected 3'-deoxy-3'-C-hydrazine base, may then react, such as by the addition of sodium cyanoborohydride, with the attached synthon 2. Following a wash, a dinucleoside linked through a hydrazino moiety is formed. Thereafter, the cycle may be repeated as desired by the addition of a synthon 1 species followed by acid/base deprotection to create a polysynthon, a resulting oligomer, of a desired sequence, linked together through modified inter-sugar linkages. In some preferred embodiments of this invention, the synthon 1 species may be a 5'-DMT protected 3'-C-hydrazine base.

One preferred embodiment of this stepwise process utilizes a diphenylethyldiamine adduct (1,3-disubstituted imidazolidino) to protect the electrophilic center of synthon 2 during attachment to the solid support. Moffatt, J. G., et al., *Journal of American Chemical Society* 90:5337–5338 (1968). Synthon 2 may preferably be attached to a solid support such as a controlled pore glass support or other suitable supports known to those skilled in the art. Attachment may take place via a standard procedure. Gait, M. J., ed., *Oligonucleotide Synthesis, A Practical Approach* (IRL Press 1984). Alternatively, preparation may occur by directly oxidizing the protected bound nucleoside with various standard oxidizing procedures. Bound synthon 2 is preferably reacted with hydrazine to produce a Schiff's base which may be subsequently reduced. Hydroxyamine is also a preferred reactant useful in this method.

Figure 2:
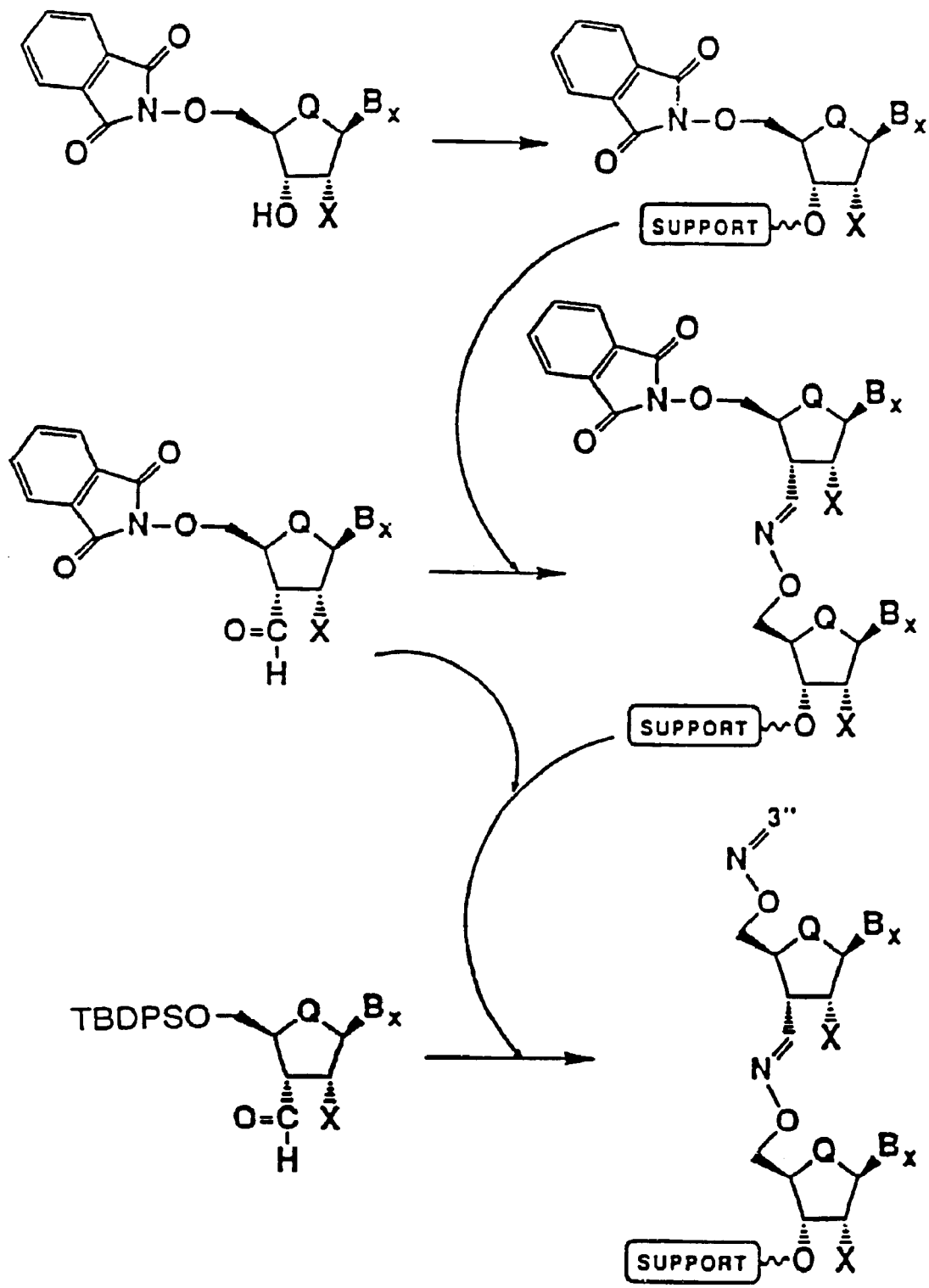
FIG. 2 is a schematic, synthetic scheme in accordance with further embodiments of the invention.

A further method of synthesizing uniform backbone linked oligonucleosides is depicted in FIG. 2. This method also employs a solid support on which a synthon 2, with a protected 5' site is bound. In this instance the 5' site of the synthon is protected with a phthalimido group. Thereafter, the 5' site of the synthon 2 is liberated with methylhydrazine in DCM and washed with DCM:methanol. The aminohydroxyl group at the 5' position of synthon 1 is also protected with a phthalimido group. Such synthon 1 is a 5'-phthalimido protected 3'-deoxy-3'-C-formyl nucleoside. Synthon 1 is reacted with synthon 2 followed by deprotection at the 5' position and washing to liberate the next 5'-aminohydroxy reaction site. The cycle is repeated with the further addition of synthon 1 sufficient times until the desired sequence is constructed. Each nucleoside of this sequence is linked together with an oxime linkage. The terminal nucleoside of the desired oligonucleoside is added to the sequence as a 5'-DMT blocked 3'-deoxy-3'-C-formyl nucleoside. The oxime linked oligonucleoside can be removed from the support. If a aminohydroxyl linked oligonucleoside is desired the oxime linkages are reduced with sodium cyanoborohydride. Alternately reduction can be accomplished while the oxime linked oligonucleoside is still connected to the support.

Also in accordance with this invention, nucleosides are provided having the structure:

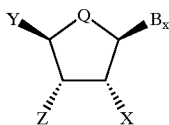

wherein $B_x$ is a variable base moiety; Q is O, $CH_2$, CHF or $CF_2$; X is H; OH; $C_1$ to $C_{10}$ lower alkyl, substituted lower alkyl, alkaryl or aralkyl; F; Cl; Br; CN; $CF_3$; $OCF_3$; OCN; O—, S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a group for improving the pharmacokinetic properties of an oligonucleotide; or a group for improving the pharmacodynamic properties of an oligonucleotide.

In such species, Y is hydroxyl, aminomethyl, hydrazinomethyl, hydroxymethyl, C-formyl, phthalimidohydroxymethyl, aryl-substituted imidazolidino, aminohydroxylmethyl, methylaminobenzenethio, methylphosphonate and methyl-alkyl phosphonate; and Z is H, hydroxyl, aminomethyl, hydrazinomethyl, hydroxymethyl, C-formyl, phthalimidohydroxymethyl, aryl substituted imidazolidino, aminohydroxylmethyl, ortho-methylaminobenzenethio, methylphosphonate or methyl alkylphosphonate.

All of the foregoing is with the proviso that when Q is O and Y is hydroxymethyl and X is H or OH then Z is not H or C-formyl; and when Q is O and X is H or OH and Z is hydroxyl then Y is not aminohydroxylmethyl, hydrazinomethyl or aryl-substituted imidazolidino.

The oligonucleotide analogues of this invention can be used in diagnostics, therapeutics, and as research reagents and kits. For therapeutic use the oligonucleotide analogue is administered to an animal suffering from a disease modulated by some protein. It is preferred to administer to patients suspected of suffering from such a disease an amount of oligonucleotide analogue that is effective to reduce the symptomology of that disease. One skilled in the art may determine optimum dosages and treatment schedules for such treatment regimens.

It is generally preferred to administer the therapeutic agents in accordance with this invention internally such as orally, intravenously, or intramuscularly. Other forms of administration, such as transdermally, topically, or intralesionally may also be useful. Inclusion in suppositories may also be useful. Use of pharmacologically acceptable carriers is also preferred for some embodiments.

EXAMPLES

The following examples are illustrative, but not limiting, of the invention. In these examples, for the NMR of dimers and other higher oligonucleosides, the monomeric units of the dimer and other higher oligonucleosides are numbered, i.e $T_1$, $T_2$, from the 5' terminus nucleoside towards the 3' terminus nucleoside—thus the 5' nucleoside of a T-T dimer is $T_1$ and the 3' nucleoside is $T_2$.

Example 1

Synthesis of CPG-bound Nucleosides for methylenehydrazine, i.e. (3'-$CR_2$—NH—NH—$CH_2$-5'), Linked Oligonucleoside Diphenylimidazolidino Protected 5'-aldehydic thymidine CPG-bound thymidine (30 micromoles of thymidine on one gram of CPG support, ABI, Foster City, Calif.) is treated at ambient temperature with a mixture of DMSO, benzene, DCC, pyridine, and trifluoroacetic acid (15 ml/15 ml/2.48 g/0.4 ml/0.2 ml in a procedure similar to the oxidation procedure of Pfitzer, K. E. and J. G. Moffatt, *Journal of American Chemical Society* 85:3027 (1963), to provide the 5'-aldehydic nucleoside. The mixture is filtered after storing overnight. The support is washed with oxalic acid (1.3 g in 5 ml benzene/DMSO, 1 to 1) and treated with 1,2-dianilinoethylene (3.0 g) for one hour, filtered, and washed with acetonitrile to afford the 5'-diphenylimidazolidino protected 5'-aldehydic thymidine.

5'-Deoxy-5'-hydrazino-thymidine

Treatment of the support-bound 5'-aldehydo thymidine with a solution of hydrazine hydrate/sodium cyanoborohydride in acetonitrile provides CPG-3'-bound 5'-deoxy-5'-hydrazino thymidine which is stored as its hydrochloride salt.

5'-Diphenylimidazolidino Protected-3'-deoxy-3'-C-hydrazinomethyl thymidine

Commercially available 3'-O-acetylthymidine was oxidized and subsequently protected as its N,N-diphenylethylenediamine derivative (1,3-diphenylimidazolidino). This provides the known 5'-deoxy-5'-diphenylimidazolidino-3'-O-acetylthymidine. Pfitzer, K. E. and J. G. Moffatt, *Journal of American Chemical Society* 85:3027 (1963). Hydrolysis of this material was achieved by methanolic ammonia treatment at ambient temperature for 15 hours. 5'-Deoxy-5'-diphenylimidazolidinothymidine (4.5 g) was dissolved in DMF (100 ml) and treated with triphenylmethyl phosphonium iodide at room temperature for 15 hours. The solvent was removed under reduced pressure and the resulting residue recrystallized from methanol to provide the 3'-deoxy-3'-iodo derivative. The 3'-deoxy-3'-iodo-5'-diphenylimidazolino thymidine was dissolved in toluene and treated with hexamethylditin, t-butylisonitrile, and AIBN. This radical reaction provides the 3'-deoxy-3'-cyano derivative which was subsequently reduced with diisobutylaluminum hydride (DIBAL-H) in toluene/THF at 0° C., to afford 3'-deoxy-3'-C-formyl-5'-diphenylimidazolidino thymidine. This material was treated with hydrazine hydrate and sodium cyanoborohydride in acetonitrile to afford 5'-diphenylimidazolidino protected-3'-deoxy-3'-C-hydrazinomethyl thymidine. The material is conveniently stored as the acetate salt.

Example 2

Synthesis of Uniform (3'-$CH_2$—NH—NH—$CH_2$-5'), i.e. methylenehydrazine, Linked Oligonucleosides on a DNA Synthesizer CPG-bound thymidine with a diphenylimidazolidino protected 5'-aldehyde from Example 1 that will become the 3'-terminal nucleoside is placed in an Applied Biosystems, Inc. (ABI) column (250 mg, 10 micromoles of bound nucleoside) and attached to an ABI 380B automated DNA Synthesizer. The automated (computer controlled) steps of a cycle that are required to couple a desmethyl nucleoside unit to the growing chain are as follows.

| STEP | REAGENT OR SOLVENT MIXTURE | TIME (min:sec) |
|------|---------------------------|----------------|
| 1 | 3% DCA in dichloroethane | 3:00 |
| 2 | Dichloroethane wash | 1:30 |
| 3 | 5'-Deoxy-5'-(1,3-diphenylimidazolidino)-3'-deoxy-3'-C-methylene hydrazine nucleoside (the second nucleoside); 20 micromoles in 30 ml of acetonitrile | 2:50 |
| 4 | Sodium borohydride (50 micromole in THF/EtOH, 50 ml) | 1:1<br>3:00 |
| 5 | Dichloroethane wash | 2:00 |
| 6 | Recycle starting at step 1 (acid wash) | 3:00 |

This procedure yields as its product nucleoside the 5'-dimethyoxytrityl substituted nucleoside unit.

At the completion of the synthesis, base deprotection and oligomer removal from the support is accomplished by the standard procedure described in oligonucleotide Synthesis: a practical approach, Ed. M. J. Gait, IRL Press, 1984. Trityl-on HPLC purification followed by acetic acid deprotection and precipitation provides the oligonucleosides as the acetate salts.

Example 3

Synthesis of 5'-deoxy-5'-hydrazino Nucleosides

5'-Deoxy-5'-hydrazinothymidine hydrochloride

To provide 5'-benzylcarbazyl-5'-deoxythymidine, 5'-O-tosylthymidine, [*Nucleosides & Nucleotides* 9:89 (1990)] (1.98 g, 5 mmol), benzylcarbazide (4.15 g, 25 mmol), activated molecular sieves (3A, 2 g), and anhydrous dimethylacetamide (100 ml) were stirred together with exclusion of moisture at 110° C. (bath temperature) for 16 hours. The products were cooled and concentrated under reduced pressure (bath temperature <50° C.). The residue was purified on a silica gel column (5×45 cm) with $CH_2Cl_2$/MeOH (9:1, v/v) as the solvent. The homogeneous fractions were pooled, evaporated to dryness and the foam recrystallized from EtOH to yield 0.7 g (36%) of 5'-benzylcarbazyl-5'-deoxythymidine; mp 201° C.; $^1$H NMR ($Me_2SO$-$d_6$) δ 1.79 (s, 3, C$\underline{H}_3$), 2.00–2.18 (m, 2, $C_2$,C$\underline{H}_2$), 2.95 (t, 2, $C_5$,C$\underline{H}_2$), 3.75 (m, 1, $C_4$,$\underline{H}$), 4.18 (m, 1, $C_3$,$\underline{H}$), 4.7 (brs, 1, O'$_2$N$\underline{H}$), 5.03 (s, 2, PhC$\underline{H}_2$), 5.2 (d, 1, $C_3$,$\underline{H}$), 6.16 (t, 1, $C_1$,$\underline{H}$), 7.2–7.4 (m, 5, $C_6\underline{H}_5$), 7.6 (s, 1, $C_6\underline{H}$), 8.7 (brs, 1, $CH_2N\underline{H}$), 11.2 (brs, 1, $C_3N\underline{H}$).

To provide the hydrochloride salt of 5-'-deoxy-5'-hydrazinothymidine as a hygroscopic powder, a mixture of the above carbazate (0.78 g, 2 mmol) and palladium on charcoal (10%, 150 mg) in anhydrous MeOH/HCl (30 ml, 2%, HCl by weight) was stirred under an atmosphere of hydrogen at room temperature for 1.5 hours. The methanolic solution was filtered through Celite to remove the catalyst. The filter cake was washed with EtOH (2×25 ml). The filtrate was concentrated under vacuum and the residue was dried overnight to remove traces of HCl. The yellow residue was dissolved in methanol (3 ml) and added dropwise to a rapidly stirred solution of ethyl acetate (150 ml). The filtered precipitate was washed with ethyl acetate (3×100 ml) and the pale yellow solid was dried under vacuum to yield 0.51 g (88%) of 5'-deoxy-5'-hydrazinothymidine hydrochloride (hygroscopic powder); $^1$H NMR ($Me_2SO$-$d_6$) δ 1.81 (s, 3, C$\underline{H}_3$), 2.02–2.22 (m, 2, $C_2$,C$\underline{H}_2$), 3.2 (m, 2, $C_5$,C$\underline{H}_2$), 3.8, (m, 1, $C_4$,$\underline{H}$), 4.2 (m, 1, $C_3$,$\underline{H}$), 6.17 (t, 1, $C_1$, $\underline{H}$), 7.54 (s, 1, $C_6$ $\underline{H}$), 11.18 (brs, 1, $C_3N\underline{H}$), the hydrazino and 3'-OH were masked by $H_2O$.

Example 4

Synthesis of 5'-trityl-1-[2,3-dideoxy-3-C-(formyl)-β-D-*erythro*-pentofuranosyl]-thymine and -uracil
Method A
3'-C-Cyano-3'-deoxy-5'-O-tritylthymidine "The following preparation should to be performed under a hood and all precautions taken not to inhale any of reagent fumes."

A suspension of 3'-deoxy-3'-iodo-5'-O-tritylthymidine (Verheyden, J. P. H.; Moffatt, J. G., *J. Org. Chem.*, 35:2868 (1970)) (60 g, 0.1 mol), hexamethylditin (36 g, 22.7 ml, 0.11 mol), t-butylisocyanide (166 g, 225 ml, 2 mol), and AIBN (1.6 g, 10 mmol) in toluene (freshly distilled over Na/benzophenone, 2 lt) was thoroughly deoxygenated by bubbling argon through the reaction mixture for 30 min. and then heated at 38° C. for 13 h. The reaction mixture was cooled at 60° C. and AIBN (1.6 g, 10 mmol) was added and heating continued for 24 h. During this period addition of AIBN was repeated for 3 times in an identical manner. The reaction mixture was cooled to room temperature and transferred on the top of a prepacked silica gel column (1.5 kg, in hexanes) and eluted with hexanes: $Et_2O$ (100% hexanes→100% $Et_2O$ with a 10% gradient change each time using 1 lt of eluent). Most of the impurities were removed during the gradient elution as non-polar compounds. Final elution with $Et_2O$ (2 lt), pooling and evaporation of appropriate fractions gave two compounds in the order these were collected. (i) 12.93 g (25%) of 3'-$\underline{C}$-Cyano-3'-deoxy-5'-$\underline{O}$-tritylthymidine as white powder (crystallized from toluene/$Et_2O$, mp 153–157° C.); $^1$H NMR ($CDCl_3$) δ 8.83 (s, 1, N$\underline{H}$), 7.04–7.4 (m, 18.5, Tr$\underline{H}$, $C_6\underline{H}$, and 0.5 Ar$\underline{H}$ from toluene), 6.10 (dd, 1, $\underline{H}_{1'}$, $J_{1',2'}$=4.1 Hz, $J_{1',2''}$=7.1 Hz), 4.20 (m, 1, $\underline{H}_{4'}$, $J_{3',4'}$=8.4 Hz, $J_{4',5'}$=2.8 Hz), 3.33–3.60(m, 3, $\underline{H}_{5',5'',3'}$) 2.68 (m, 1, $\underline{H}_{2'}$, $J_{2',2''}$=13.8 Hz), 2.52 (m, 1, $\underline{H}_{2''}$), 2.28 (s, 1.5, 0.5 C$\underline{H}_3$ from toluene), and 1.50 (s, 3, C$\underline{H}_3$). Anal. Calcd. for $C_{30}H_{27}N_3O_4$·0.5 $C_7H_8$ (toluene from crystallization): C, 74.56; H, 5.79; N, 7.78. Found: C, 74.27; H, 5.78; N, 7.66. The reaction mixture also gave 4.82 g, (10%) of 1-(3'-C-cyano-2',3'-dideoxy-5'-O-trityl-β-D-*threo*-pentofuranosyl)-thymine; $^1$H NMR ($CDCl_3$) δ 8.72 (s, 1, N $\underline{H}$), 7.03–7.44 (m, 18.5, Tr$\underline{H}$, $C_6\underline{H}$, and 0.5 Ar$\underline{H}$ from toluene), 6.13 (pseudo t, 1, $\underline{H}_{1'}$, $J_{1',2'}$=6.7 Hz, $J_{1',2''}$=5.7 Hz), 4.09 (m, 1, $\underline{H}_{4'}$, $J_{3',4'}$=6.7 Hz, $J_{4',5'}$=4.9 Hz), 3.56 (m, 2, $\underline{H}_{5',5''}$), 3.28 (m, 1, $\underline{H}_{3'}$, $J_{3',2'}$=8.2 Hz, $J_{3',2''}$=5.2 Hz), 2.70 (m, 1, $\underline{H}_{2'}$, $J_{2',2''}$=14 Hz), 2.28 (s, 1.5, C$\underline{H}_3$ from toluene) and 1.60 (s, 3, C$\underline{H}_3$). Anal. Calcd. for $C_{30}H_{27}N_3O_4$·0.5 $C_7H_8$ (toluene from crystallization): C, 74.56; H, 5.79; N, 7.78. Found: C, 74.10; H, 5.74; N, 7.52.

Epimerization: To a suspension of 1-(3'-$\underline{C}$-Cyano-2',3'-dideoxy-5'-$\underline{O}$-trityl-β-$\underline{D}$-threo-pentofuranosyl)thymine (0.30 g, 0.61 mmol) in methanol (20 ml) was added dropwise a 1N solution of NaOMe until the pH of solution reached≈9. The resulting mixture was heated to reflux for 20 h. The solution was cooled (0° C.) and neutralized with 1N HCl/MeOH and evaporated under reduced pressure. The residue was purified as described above to furnish 0.185 g (62%) of 3'-$\underline{C}$-cyano-3'-deoxy-5'-$\underline{O}$-tritylthymidine. (A synthesis for 3'-deoxy-3'-$\underline{C}$-cyano-5'-$\underline{O}$-tritylthymine was reported in *Tetrahedron Letters* 29:2995 (1988). This report suggested 3'-deoxy-3'-$\underline{C}$-cyano-5'-$\underline{O}$-tritylthymine is formed as a single product, however, we found a mixture is produced. By the above epimerization, the xylo component of this mixture is converted to the compound of interest, 3'-deoxy-3'-$\underline{C}$-cyano-5'-$\underline{O}$-tritylthymine.)

3'-Deoxy-3'-C-formyl-5'-O-tritylthymine

DIBAL-H (1M in toluene, 50 ml, in 5 portions over a period of 5 h) was added to a stirred solution of 3'-

C-cyano-3'-deoxy-5'-O-tritylthymidine (9.92 g, 20 mmol) in dry THF (10 ml) under argon at 0° C. The solution was stirred at room temperature for 1 h and cooled again to 0° C. MeOH (25 ml) was added dropwise to the cold solution while stirring and after complete addition the solution was brought to room temperature. A saturated aqueous $Na_2SO_4$ solution (11 ml) was added to the reaction mixture and stirred for 12 h. Powdered anhydrous $Na_2SO_4$ (30 g) was added to the reaction mixture and suspension was stirred for 30 min. The suspension was filtered and residue was thoroughly washed with MeOH:$CH_2Cl_2$ (1:9 v/v) until all of the product was washed off. The filtrates were combined and concentrated under vacuum, to furnish a gummy residue. The residue was purified by silica gel chromatography using $CH_2Cl_2$:MeOH (100% $CH_2Cl_2$→9:1, v/v) for elution to obtain 5.45 g (55%) of 3'-deoxy-3'-C-formyl-5'-O-tritylthymine as a white foam. $^1$H NMR (CDCl$_3$) δ 9.61 (d, 1, CHO, $J_{3',3''}$=1.5 Hz), 8.44 (s, 1, NH), 7.46 (s, 1, C$_6$H), 7.17–7.45 (m, 15, TrH), 6.04 (pseudo t, 1, H$_{1'}$, $J_{1',2'}$=5.3 Hz, $J_{1',2''}$=6.6 Hz), 4.31 (m, 1, H$_{4'}$, $J_{4',5'}$=3.3 Hz, $J_{3',4'}$=7 Hz), 3.28–3.55 (m, 3, H$_{5',5'',3'}$), 2.69 (m, 1, H$_{2'}$), 2.28 (m, 1, H$_{2''}$), 1.48 (s, 3, CH$_3$). Anal. Calcd. for $C_{30}H_{28}N_2O_5 \cdot H_2O$: C, 70.03; H, 5.88; N, 5.44. Found: C, 70.40; H, 6.00; N, 5.33.

1-[3-Deoxy-3-C-(formyl)-5-O-trityl-β-D-erythro-pentofuranosyl]uracil

To a stirred solution of 3'-cyano-2',3'-dideoxy-5'-O-trityl uridine (0.96 g, 2 mmol), (prepared in a manner equivalent to that of the thymidine analogue above) in dry THF (20 ml) under argon, was added a solution of DIBAL-H in toluene (Aldrich) (1M, 4 ml) at −10° C. over a period of 10 min. After 30 mins the reaction was quenched with MeOH (5 ml) at −10° C. The mixture was further stirred at ambient temperature for 30 mins and diluted with $CH_2Cl_2$ (25 ml) before concentrating under vacuum. This process was repeated with $CH_2Cl_2$ (3×25 ml) in order to remove the residual THF. The residue was purified by flash chromatography on silica gel (25 g). Elution with $CH_2Cl_2$ (9:1, v/v) and crystallization from $CH_2Cl_2$/MeOH gave 5'-O-trityl-3'-C-formyl-2',3'-dideoxyuridine (0.53 g, 53%); mp 100° C.; $^1$H NMR (CDCl$_3$) δ 2.25–2.8 (m, 2, CH$_2$), 3.4 (m, 1, C$_3$H), 3.45–3.6 (m, 2, C$_5$CH$_2$), 4.37 (m, 1, C$_4$H), 5.4 (d, 1, C$_5$H), 6.1 (m, 1, C$_1$H), 7.2–7.4 (m, 15, C$_6$H$_5$), 7.81 (d, 1, C$_6$H), 7.95 (br s, 1, NH), 9.61 (s, 1, HC=O).

Method B

1-[3-deoxy-3-C-(formyl)-5-O-trityl-β-D-erythro-pentofuranosyl]thymine

1-Methyl-5-O-(t-butyldiphenylsilyl)-2,3-dideoxy-3-C-(formyl)-D-erythro-pentofuranose was obtained as an oil in 90% yield using the DIBAL-H reduction of 1-methyl-5-(t-butyldiphenylsilyl)-2,3-dideoxy-3-C-cyano-D-erythro-pentofuranose as described in *Tetrahedron*, 44:625 (1988). The 3-C-formyl group is derivatized to the oxime with methoxyamine. The oxime blocked intermediate was glycosylated with silyated thymine to give an α and β mixture of the title compound. After deblocking, the β anomer compares to that prepared via method A.

Method C

1-[3-deoxy-3-C-(formyl)-5-O-trityl-β-D-erythro-pentofuranosyl]-uracil and -thymine A mixture of 3'-deoxy-3'-iodo-5'-O-tritylthymidine (0.59 g, 4 mmol), tris(trimethylsilyl) silane (2.87 g, 1.2 mmol), AIBN (12 mg, 0.072 mmol), and toluene (20 ml) were mixed in a glass container and saturated with argon (bubbling at room temperature). The glass vessel was inserted into a stainless steel pressure reactor, and pressurized with carbon monoxide (80 psi), closed and heated (90° C., bath) for 26 hrs. The reaction mixture was cooled (0° C.) and the CO was allowed to escape carefully (under the fume hood). The product was purified by flash column chromatography on silica gel (20 g). Elution with EtOAc:Hexanes (2:1, v/v) and pooling the appropriate fractions furnished 0.30 g (61%) of the title compound as a foam.

A radical carbonylation of 2',3'-dideoxy-3'-iodo-5'-trityluridine in a similar manner gives the 3'-C-formyl uridine derivative.

Example 5

Synthesis of methylenehydrazone Linked (3'-CH=NH—NH—CH$_2$-5'), methylenehydrazine Linked (3'-CN$_2$—NH—NH—CH$_2$-5') and methylene(dimethylhydrazo) Linked (3'-CH$_2$—N (CH$_3$)—N(CH$_3$)—CH$_2$-5') dinucleosides 3'-De(oxyphosphinico)-3'-[methylene(hydrazone)]-5'-O-tritylthymidylyl-(3'→5')-5'-deoxythymidine A mixture of 3'-deoxy-3'-C-formyl-5'-O-tritylthymidine, 0.645 g, 1.30 mmol), 5'-deoxy-5'-hydrazinothymidine hydrochloride (0.397 g, 1.36 mmol) in dry $CH_2Cl_2$/MeOH/ AcOH (20 ml/10 ml/0.5 ml) was stirred for 30 min at room temperature. The solvent was evaporated under vacuum and the hydrazone intermediate was analyzed by $^1$H NMR (DMSO-d$_6$) δ 1.1 (br s, 2 NH), 8.3 (s, 1, C=N—NH), 7.5–7.74 (m, 17, Tr H, 2C$_6$H), 6.8 (1d, 1t, 1, HC=N, two isomers), 6.0–6.1 (2m, 2, H$_{1'}$), 5.30 (br t, 1, OH), 3.8–4.2 (3m, 3, H$_{3'}$, 2 H$_{4'}$), 3.0–3.3 (m, 5, 2H$_{5',5''}$, H$_{3'}$), 2.0–2.4 (m, 4, 2H$_{2',2}$), 1.5 and 1.7 (2s, 6, 2 CH$_3$).

3'-De(oxyphosphinico)-3'-[methylene(dimethylhydrazo)]-5'-O-tritylthymidylyl-(3'→5')-5'-deoxythymidine The above hydrazone dimer was dissolved in AcOH (10 ml) and to this was added small portions of NaBH$_3$CN (4×0.12 g, 7.74 mmol) while stirring at room temperature for 30 min. The solution was stirred for an additional 15 min before the addition of aqueous HCHO (20%, 3.9 ml, 26 mmol), NaBH$_3$CN (3.9 mmol), and AcOH (10 ml). The suspension was further stirred for 15 min. and solution evaporated under vacuum. The residue was coevaporated with MeOH (3×25 ml) to give the methylenehydrazo dimer; $^1$H NMR (CDCl$_3$) δ 6.8–7.8 (m, 15, TrH, 2 C$_6$H), 6.12 (m, 2, 2H$_{1'}$), 4.20 ((m, 1, T2 H$_{3'}$), 4.05 (m, 1, T2 H$_{4'}$), 3.89 (m, 1, T1 H$_{4'}$), 3.80 (s, 6, 2 OCH$_3$), 3.21–3.53 (m, 2, T1 H$_{5',5''}$), 2.11–2.75 (m, 10, T2 H$_{5',5''}$H, T1 H$_{3'}$, T1 H$_{3'}$, T1 T2 H$_{2',2''}$) 2.26 (s, 6, 2N—CH$_3$), 1.88 and 1.49 (2s, 6, 2 CH$_3$), and other protons.

3'-De(oxyphosphinico)-3'-[methylene(dimethylhydrazo)]-thymidylyl-(3'-5')-5'-deoxythymidine The above hydrazine dimer was then stirred with 37% aqueous HCl (1 ml) in MeOH (25 ml) at room temperature for 24 h. The resulting mixture was neutralized with NH$_4$OH (pH≈8) and evaporated to dryness. The residue was purified by reverse phase HPLC (supelcosil LC18, 5 m, H$_2$O: CH$_3$CN gradient) to furnish 0.61 g of the title methylene (dimethylhydrazine) linked dimer (89%). $^1$H NMR (90° C., DMSO-d$_6$+1 drop of D$_2$O) δ 7.66 and 7.43 (2s, 2, 2 C6H), 6.02 (pseudo t, 1, T2 H$_{1'}$, $J_{1',2'}$=7.2 Hz, $J_{1',2''}$=7.7 Hz), 5.96 (pseudo t, 1, T1 H$_{1'}$, $J_{1',2'}$=5.6 H$_2$, $J_{1',2''}$=6.2 Hz), 4.12 (m, 1, T2 H$_{3'}$), 3.90 (m, 1, T2 H$_{4'}$), 3.71 (m, 1, T1 H$_{4'}$), 3.61 (m, 2, T1 H$_{5',5''}$), 2.4–2.8 (m, 5, T2 H$_{5',5''}$, T1 H$_{3''}$, T1 H$_{3'}$), 2.29 (2s, 6, 2 N—CH$_3$), 2.12 (m, 4, 2H$_{2',2''}$), 1.76 and 1.74 (2s, 6, 2 CH$_3$). Anal. Calcd. for $C_{23}H_{34}N_6O_8 \cdot H_2O$: C, 51.10, H, 6.71; N, 15.54. Found: C, 51.05; H, 6.68; N, 15.54. MS FAB m/z 523 (M+H)$^+$.

Example 6

Synthesis of methylene(dimethylhydrazine) Linked (3'-CH$_2$—N(CH$_3$)—N(CH$_3$)—CH$_2$-5') 5'-dimethoxytrityl-3'-β-cyanoethoxydiisopropylphosphoramidite dinucleosides 3'-De(oxyphosphinico)-3'-[methylene(dimethylhydrazo)]-thymidylyl-5'-O-(dimethoxytriphenylmethyl)-(3'→5')-3'-O-(β-cyanoethyl-N-diisopropylaminophosphiryl)thymidine The methylene(dimethylhydrazine) dimer of Example 5 was dimethyoxytritylated following the standard procedure described in oligonucleotide Synthesis: a practical approach, Ed. M. J. Gait, IRL Press, 1984, to furnish a homogenous foam $^1$H NMR (CDCl$_3$) δ 6.8–7.8 (m, 20, DMTr, 2$\underline{H}_6$), 6.12 (m, 2, 2$\underline{H}_{1'}$), 4.20 (m, 1, T$_2$ $\underline{H}_{3'}$), 4.05 (m, 1, T$_2$ $\underline{H}_{4'}$), 3.89 (m, 1, T$_1$ $\underline{H}_{4'}$), 3.80 (s, 6, 2 OC$\underline{H}_3$ of DMTr), 3.21–3.53 (m, 2, T$_1$ $\underline{H}_{5'5"}$), 2.11–2.75 (m, 9, T$_1$ $\underline{H}_{5'5"}$, $\underline{H}_{3"}$, T$_1$ H$_{3'}$, 2$\underline{H}_{2'2"}$), 2.26 (2s, 6, 2 N—C$\underline{H}_3$) and 1.88 and 1.49 (2s, 2, C$_5$ C$\underline{H}_3$)] which on phosphitylation via the procedure described in Oligonucleotide Synthesis: a practical approach, Ed. M. J. Gait, IRL Press, 1984, provided a 65% yield of the title compound. $^1$H NMR (CDCl$_3$) δ 6.14 (m, 1, T2 $\underline{H}_{1'}$), 6.01 (m, 1, T1 $\underline{H}_{1'}$), 3.80 (s, 6, 2 O C$\underline{H}_3$), 2.23 (m, 6, 2 N—C$\underline{H}_3$), 1.78 and 1.45 (2s, 6, 2 C$\underline{H}_3$), and other protons. $^{31}$P NMR (CDCl$_3$) δ 149.43 and 148.85 ppm.

Example 7

Synthesis of Intermittent methylene (dimethyhydrazine) (3'-CH$_2$—NCH$_3$—NCH$_3$—CH$_2$-5') Linked Oligonucleosides CPG-bound thymidine (or any other nucleoside that is to become the 3'-terminal base) was placed in an Applied Biosystems, Inc. (ABI) column (250 mg, 10 micromoles of bound nucleoside) and attached to an ABI 3808 automated DNA Synthesizer. The standard, automated (computer controlled) steps utilizing phosphoramidite chemistries are employed to place the methylenehydrazine thymidine dimer into the sequence at any desired location.

Example 8

Synthesis of (3'-CH$_2$—NH—S—CH$_2$-5') Linkage 3'-de(oxyphosphinico)-3'-[methylene(methylsulfenyl)]-thymidylyl-(3'→5')-5'-deoxythymidine The title compound will be prepared from two intermediate nucleosides. The first nucleoside, 3'-$\underline{O}$-benzyl-5'-deoxy-5'-mercaptothymidine will be prepared in 3 steps from 3'-$\underline{O}$-benzoylthymidine according to the procedure of J. H. Marriott et al., Tet. Letts., 31:7385 (1990), via a formation of the 5'-$\underline{S}$-[9-(4-methoxyphenyl)xanthen-9-yl] group and subsequent deblocking to yield a 5'-SH group. The second nucleoside, 3'-$\underline{C}$-methylamino-5'-$\underline{O}$-tritylthymidine will be prepared in 3 steps from 3'-$\underline{C}$-formyl-5'→$\underline{O}$-tritylthymidine described in Example 4 above. The 3 steps procedure includes NaBH$_4$ reduction of the formyl group followed by conversion to an azido group with LiN$_3$/DMF and subsequent reduction with TBTH/toluene to furnish the 3'-$\underline{C}$—CH$_2$NH$_2$ group. Addition of 3'-$\underline{C}$-methylamino-5'-$\underline{O}$-tritylthymidine nucleoside (1 mmol) to an aqueous sodium hypochloride (4 mmol) solution will furnish the chloramide intermediate, which on cooling (0 °C.) and reaction with the 3'-$\underline{O}$-benzyl-5'-deoxy-5'-mercaptothymidine nucleoside (0.9 mmol) for 15 min followed by the usual work-up and purification by chromatography will furnish the title compound.

Example 9

Synthesis of 5'-O-phthalimido Nucleosides
5'-O-Phthalimidothymidine

To a stirred solution of thymidine (24.22 g, 0.1 mol), N-hydroxyphthalimide (21.75 g, 0.13 mol), triphenylphosphine (34 g, 0.13 mol) in dry DMF (400 ml) was added diisopropylazodicarboxylate (30 ml, 0.15 mol) over a period of 3 h at 0° C. After complete addition the reaction mixture was warmed up to room temperature and stirred for 12 h. The solution was concentrated under vacuum (0.1 mm,<40° C.) to furnish an orange-red residue. The residual gum was washed several times with Et$_2$O and washing were discarded. The semi-solid residue was suspended in EtOH (500 ml) and heated (90° C.) to dissolve the product. On cooling 30.98 g (80%) of 5'-$\underline{O}$-phthalimidothymidine was collected in 3-crops as white crystalline material, mp 233–235° C. (decomp.); $^1$H NMR (DMSO-d$_6$) δ 11.29 (s, 1, N$\underline{H}$), 7.85 (m , 4, Ar$\underline{H}$), 7.58 (s, 1, C$_6\underline{H}$), 6.20 (t, 1, $\underline{H}_{1',2'}$=7.8 Hz, J$_{1',2"}$=6.5 Hz), 5.48 (d, 1, O$\underline{H}_{3'}$), 4.36 (m, 3, $\underline{H}_{4',5',5"}$), 4.08 (m, 1, $\underline{H}_{3'}$), 2.09–2.13 (m, 2, $\underline{H}_{2',2"}$), and 1.79 (s, 3, C$\underline{H}_3$). Anal. Calcd. for C$_{18}$H$_{17}$O$_7$N$_3$.0.7H$_2$O: C, 54.05; H, 4.64; N, 10.51. Found: C, 53.81; H, 4.25; N, 10.39.
2'-deoxy-5'-O-phthalimidouridine An analogous reaction on 2'-deoxyuridine gave the corresponding 2'-deoxy-5'-$\underline{O}$-phthalimidouridine; mp 241–242° C.

Example 10

Synthesis of 5'-O-phthalimido-3'-O-(t-butyldiphenylsilyl)thymidine and 2'-deoxy-5'-O-phthalimido-3'-O-(t-butyldiphenylsilyl)uridine
3'-O-(t-butyldiphenylsilyl)-5'-O-phthalimidothymidine A mixture of 5'-$\underline{O}$-phthalimidothymidine (8.54 g, 22 mmol), t-butyldiphenylsilylchloride (6.9 ml, 26.5 mmol), imidazole (3.9 g, 57.3 mmol) and dry DMF (130 ml) was stirred at room temperature for 16 h under argon. The reaction mixture was poured into ice-water (600 ml) and the solution was extracted with CH$_2$Cl$_2$ (2×400 ml). The organic layer was washed with water (2×250 ml) and dried (MgSO$_4$). The CH$_2$Cl$_2$ layer was concentrated to furnish a gummy residue which on purification by silica gel chromatography (eluted with EtOAc:Hexanes; 1:1, v/v) furnished 12.65 g (92%) of 3'-$\underline{O}$-(t-butyldiphenylsilyl)-5'-$\underline{O}$-phthalimidothymidine as crystalline material (mp 172–173.5° C.). $^1$H NMR (DMSO-d$_6$) δ 11.31 (s, 1, N$\underline{H}$), 7.83 (m, 4, Ar$\underline{H}$), 7.59 (m, 4, TBDPh$\underline{H}$), 7.51 (s, 1, C$_6\underline{H}$), 7.37–7.45 (m, 6, TBDPh$\underline{H}$), 6.30 (dd, 1, $\underline{H}_{1'}$, J$_{1',2'}$=8.8 Hz, J$_{1',2"}$=5.6 Hz), 4.55 (m, 1, $\underline{H}_{4'}$), 4.15 (m, 1, $\underline{H}_{3'}$) 3.94–4.04 (m, 2, $\underline{H}_{5',5"}$), 2.06–2.13 (m, 2, $\underline{H}_{2',2"}$), 1.97 (s, 3, C$\underline{H}_3$), 1.03 (s, 9, C(C$\underline{H}_3$)$_3$). Anal. Calcd. for C$_{34}$H$_{35}$O$_7$N$_3$Si: C, 65.26; H, 5.64; N, 6.71. Found: C, 65.00; H, 5.60; N, 6.42.
3'-O-(t-butyldiphenylsilyl)-2'-deoxy-5'-O-phthalimidouridine An analogous reaction of 2'-deoxy-5'-$\underline{O}$-phthalimidouridine will give the corresponding 3'-$\underline{O}$-(t-butyldiphenylsilyl)-2'-deoxy-5'-$\underline{O}$-phthalimidouridine.

Example 11

Synthesis of 5'-O-amino Nucleoside
5'-O-amino-3'-O-(t-butyldiphenylsilyl)thymidine To a stirred solution of 3'-$\underline{O}$-(t-butyldiphenylsilyl)-5'-$\underline{O}$-phthalimidothymidine (10 g, 16 mmol) in dry CH$_2$Cl$_2$ (100 ml) was added methylhydrazine (1.3 ml, 24 mmol) under argon at room temperature and solution stirred for 12 h. The solution was cooled (0° C.) and filtered. The white residue was washed with CH$_2$Cl$_2$ (2×25 ml) and combined filtrates were evaporated to furnish gummy residue. The residue on purification by silica gel column chromatography (elution with CH$_2$Cl$_2$:MeOH, 98:2, v/v) furnished 7.03 g (89%) of 5'-$\underline{O}$-amino-3'-$\underline{O}$-(t-butyldiphenylsilyl)thymidine that crystallized from CH$_2$Cl$_2$/MeOH mp 141–143° C. $^1$H NMR (DMSO-d$_6$) δ 11.29 (s, 1, N$\underline{H}$), 7.42–7.62 (m, 11, TBDPh$\underline{H}$, C$_6$ $\underline{H}$), 6.25 (dd, 1, $\underline{H}_{1'}$, J$_{1',2'}$=8.4 Hz, J$_{1',2''}$=6.3 Hz), 6.02 (s, 2, N$\underline{H}_2$), 4.35 (m, 1, $\underline{H}_{4'}$), 4.04 (m, 1, $\underline{H}_{3'}$), 3.34–3.51 (m, 2, $\underline{H}_{5',5''}$) 2.04 (m, 2, $\underline{H}_{2',2''}$), 1.73 (s, 3, C$\underline{H}_3$), 1.03 (s, 9, C(C$\underline{H}_3$)$_3$). Anal. Calcd. for C$_{26}$H$_{33}$O$_5$N$_3$Si: C, 63.00; H, 6.71; N, 8.48. Found: C, 62.85; H, 6.67; N, 8.32.

Example 12

Synthesis of (3'-CH=N—O—CH$_2$-5') Linked Oligonucleoside (an Oxime Linked Dimer) 3'-De(oxyphosphinico)-3'-(methylidynenitrilo)thymidylyl-(3'→5')-thymidine A mixture of 3'-deoxy-3'-$\underline{C}$-formyl-5'-$\underline{O}$-tritylthymine (0.99 g, 2 mmol), 5,-amino-3-$\underline{O}$-(t-butyldiphenylsilyl)thymidine (0.99 g, 2 mmol) and AcOH (0.3 ml) in dry CH$_2$Cl$_2$ (20 ml) was stirred for 1 h at room temperature. The solvent was evaporated under vacuum and the crude blocked 3'-de(oxyphosphinico-3'-(methylidynenitrilo)thymidylyl-(3'→5')-3'-(t-butyldiphenylsilyl)thymidine product was dissolved in THF (20 ml). A THF solution of nBU$_4$NF (1M, 5 ml) was added to the stirred reaction mixture at room temperature. After 1 h solution was purified by silica gel chromatography (elution with CH$_2$Cl$_2$:MeOH; 99:4, v/v) to furnish 3'-deblocked dimer. The dimer was dissolved in anhydrous MeOH (50 ml) and to this a MeOH/HCl solution (0.14M, 2.5 ml) was added. The reaction mixture was stirred at room temperature for 15 h. Anhydrous pyridine (10 ml) was added to the above solution and solvents were evaporated to dryness to furnish crude oxime dimer. The crude product was purified by silica gel chromatography (elution with CH$_2$Cl$_2$:MeOH; 92:8, v/v) to furnish the title compound, 3'-De(oxyphosphinico)-3'-(methylidynenitrilo)thymidylyl-(3'→5')-thymidine, (0.87 g, 89%) as a mixture of E/Z isomers. The two geometrical isomers were separated by reverse phase HPLC (Supelcosil LC18, 5μ, H$_2$O:CH$_3$CN gradient). (Z-isomer of title compound) $^1$H NMR (DMSO-d$_6$) δ 11.28 (br s, 2, 2N$\underline{H}$), 7.39 and 7.78 (2s, 2, 2C6H), 6.92 (d, 1, T1 $\underline{H}_{3''}$, J$_{3',3''}$=6.7 Hz), 6.15 (pseudo t, 1, T2 $\underline{H}_{1'}$, J$_{1',2'}$=7.8 Hz, J$_{1',2''}$=6.3 Hz), 6.04 (dd, 1, T1 $\underline{H}_{1'}$, J$_{1',2'}$=7.1 Hz, J$_{1',2''}$=6.3 Hz), 5.34 (d, 1, T2 O$\underline{H}$), 5.12 (t, 1, T1 O$\underline{H}$), 4.11–4.25 (m, 3, T2 $\underline{H}_{5'5''}$, T2 $\underline{H}_{3'}$). 3.96 (m, 1, T2 $\underline{H}_{4'}$), 3.90 (m, 1, T1 $\underline{H}_{4'}$), 3.49–3.69 (m, 3, T1 $\underline{H}_{5',5''}$, T1 $\underline{H}_{3'}$), 2.06–2.31 (m,4, T1 $\underline{H}_{2',2''}$, T2 $\underline{H}_{2',2''}$), 1.73 (s, 6, 2C$\underline{H}_3$). Anal. Calcd. for C$_{21}$H$_{27}$N$_5$O$_9$.H$_2$O: C, 49.31; H, 5.72; N, 13.69. Found: C, 49.32; 5.57; N, 13.59. (E-isomer of the title compound) $^1$H NMR (DMSO-d$_6$) δ 11.3 (2 br s, 2, 2N$\underline{H}$), 7.81 (s, 1, C$_6$$\underline{H}$), 7.52 (d, 1, T1 $\underline{H}_{3''}$, J$_{3',3''}$=6.7 Hz), 7.45 (s, 1, C$_6$$\underline{H}$), 6.10 (pseudo t, 1, T2 $\underline{H}_{1'}$, J$_{1',2'}$=7.6 Hz, J$_{1',2''}$=6.4 Hz), 6.04 (dd, 1, T1 $\underline{H}_{1'}$, J$_{1',2'}$=7.3 Hz, J$_{1',2''}$=3.4 Hz), 5.36 (d, 1, T2 O$\underline{H}$), 5.16 (t, 1, T1 O$\underline{H}$), 4.07–4.22 (m, 3, T2 $\underline{H}_{3',5',5''}$), 3.91 (m, 2, T1 T2 $\underline{H}_4$), 3.50–3.73 (m, 2, T1 $\underline{H}_{5',5''}$), 3.12 (m, 1, T1 $\underline{H}_{3'}$), 2.05–2.44 (m, 4, T1 T2 $\underline{H}_{2',2''}$) and 1.76 (s, 6, 2C$\underline{H}_3$). MS FAB: M/z 494 (M+H)$^+$.

Example 13

Synthesis of Phosphoramidate Containing (3'-CH=N—O—CH$_2$-5') Linked Oligonucleoside 3'-De(oxyphosphinico)-3'-methylidynenitrilo)-5'-O-(dimethyoxytriphenylmethyl)-thymidylyl-(3'→5')-3'-O-(β-cyanoethyldiisopropylaminophosphiryl)thymidine The isomeric dimer of Example 12 was further dimethyoxytrityled at the hydroxyl group of the 5' terminus nucleoside followed by conversion to its 3'-$\underline{O}$-β-cyanoethyldiisopropylphosphoramidite derivative at the hydroxyl group at the 3' terminus nucleoside of the dimer following the procedure described in Oligonucleotide Synthesis: a practical approach, Ed. M. J. Gait, IRL Press, 1984, to yield the title compound. $^1$H NMR (CDCl$_3$) δ 8.77 (br s, 2, 2N$\underline{H}$), 7.68 (s, 0.77, T1 C$_6$$\underline{H}$ E-isomer), 7.59 (s, 0.23, T1 C$_6$$\underline{H}$ E-isomer), 6.3 (ps t, 1, T2 C$\underline{H}_{1'}$), 6.14 (m, 0.77, T1 C $\underline{H}_1$,E-isomer), 6.08 (m, 0.23, T$_1$ C$\underline{H}_{1'}$ Z-isomer), 1.80 and 1.50 (2S, 6, 2 C$\underline{H}_3$) and other protons. $^{31}$P NMR (CDCl$_3$) 150.77 and 150.38 (Z-isomer); 150.57 and 150.38 (E-isomer).

The protected dimer can be conveniently stored and used for coupling utilizing an automated DNA synthesizer (ABI 380B) as and when required for specific incorporation into oligomers of therapeutic value. Further as per further examples of the specification, the oxime linked dimer is reduced to a dimer bearing a corresponding hydroxylamine linkage and this in turn can be alkylated to a hydroxylmethylamine or other hydroxyalkylamine linkage.

Example 14

Synthesis of (3'-CH$_2$—NH—O—CH$_2$-5') Linked Oligonucleoside 3'-De(oxyphosphinico)-3'-(methyleneimino)thymidylyl-(3'→5')-thymidine To a stirred solution of blocked dimer 3'-de (oxyphosphinico)-3'-(methylidynenitrilo)thymidylyl-(3'→5')-3'-$\underline{O}$-(t-butyldiphenylsilyl)thymidine (0.49 g, 1 mmol) in glacial AcOH (5 ml) was added NaBH$_3$CN (0.19 g, 3 mmol) in 3-portions under argon at room temperature. The suspension was stirred for 1 h until bubbling of solution ceased. Additional NaBH$_3$CN (0.19 g, 3 mmol) was added in a similar manner and stirring continued for 1 h. The AcOH was removed under reduced pressure to furnish 3'-de (oxyphosphinico)-3'-(methyleneimino)thymidylyl-(3'→5')-3'-$\underline{O}$-(t-butyldiphenylsilyl)thymidine. Deblocking of this dimer as described before using nBu$_4$NF/THF and HCl/MeOH furnished the title compound, 3'-de (oxyphosphinico)-3'-(methyleneimino)-thymidylyl-(3'→5')-thymidine, (0.44 g, 90%) as white powder. This dimer was further purified by HPLC (as described for the 3'-de (oxyphosphinico)-3'-(methylidynenitrilo)thymidylyl-(3'→5')-thymidine dimer of Example 12) to obtain an analytically pure sample. $^1$H NMR (DMSO-d$_6$) δ 11.23 (br s, 2, 2N$\underline{H}$), 7.83 and 7.49 (2s, 2, 2C$_6$$\underline{H}$), 6.82 (t, 1, N$\underline{H}$O), 6.14 (pseudo t, 1, T2 $\underline{H}_{1'}$, J$_{1',2'}$=7.6 Hz, J$_{1',2''}$=6.5 Hz), 5.96 (dd, 1, T1 $\underline{H}_{1'}$, J$_{1',2'}$=6.9 Hz, J$_{1',2''}$=4.3 Hz), 5.28 (s, 1, T2 O$\underline{H}$), 5.08 (s, 1, T1 O$\underline{H}$), 4.18 (m, 1, T2 $\underline{H}_{3'}$), 3.89 (m, 1, T1 $\underline{H}_{4'}$), 3.54–3.78 (m, 5, T1 T2 $\underline{H}_{5',5''}$, T2 $\underline{H}_{4'}$), 2.76–2.94 (m, 2, T1 $\underline{H}_{3''}$), 2.42 (m, 1, T1 $\underline{H}_{3'}$), 2.0–2.17 (m, 4, T1, T2 $\underline{H}_{2',2''}$), 1.77 and 1.74 (2s, 6, 2 C$\underline{H}_3$). MS FAB: M/z 496 (M+H)$^+$. Anal. Calcd. for C$_{21}$H$_{29}$N$_5$O$_9$.H$_2$O: C, 49.12; H, 6.09; N, 13.64. Found: C, 48.99; H, 5.96; N, 13.49.

Example 15

Synthesis of Methylated [3'-CH$_2$—N(CH$_3$)—O—CH$_2$-5'] Linked Oligonucleoside 3'-De(oxyphosphinico)-3'-[methylene(methylimino)] thymidylyl-(3'→5') thymidine To a stirred solution of 3'-de(oxyphosphinico)-3'-(methyleneimino)thymidylyl-(3'→5')-3'-$\underline{O}$-(t-butyldiphenylsilyl)thymidine dimer (0.99 g, 1 mmol) in glacial AcOH (10 ml) was added aqueous HCHO (20%, 3 ml). The solution was stirred for 5 min. at room temperature and to this was added NaBH$_3$CN (0.19 g, 3 mmol) in 3-portions under argon at room temperature. The addition of NaBH$_3$CN (0.19 g) was repeated once more and solution was further stirred for 1 h. The reaction mixture was concentrated to furnish crude 3'-de(oxyphosphinico)-3'-

[methylene(methylimino)]thymidylyl-(3'→5')-3'-O-(t-butyldiphenylsilyl)thymidine dimer, which on deblocking (nBu$_4$NF/THF, HCl/MeOH) furnished the title compound, 3'-de(oxyphosphinico)-3'-[methylene (methylimino)]thymidylyl-(3'→5') thymidine, (0.44 g, 87%) as white solids. The 3'-de(oxyphosphinico)-3'-[methylene-(methylimino)]thymidylyl-(3'→5') thymidine dimer was further purified by preparative HPLC furnishing an analytically pure sample. $^1$H NMR (DMSO-d$_6$) δ 11.30 and 11.24 (2s, 2, 2N$\underline{H}$), 7.82 and 7.50 (2s, 2, 2C$_6\underline{H}$), 6.15 (pseudo t, 1, T2 $\underline{H}_{1'}$, $J_{1',2'}$=6.3 Hz, $J_{1',2''}$=7.3 Hz), 6.00 (pseudo t, 1, T1 $\underline{H}_{1'}$, $J_{1',2'}$=4.2 Hz, $J_{1',2''}$=6.1 Hz), 5.31 (m, 1, T2 O$\underline{H}$), 5.08 (m, 1, T1, O$\underline{H}$), 4.17 (m, 1, T2 $\underline{H}_{3'}$), 3.88 (m, 1, T2 $\underline{H}_{4'}$), 3.57–3.83 (m, 5, T1 T2, $\underline{H}_{5',5''}$, T1 $\underline{H}_{4'}$), 2.69 (m, 2, T1 $\underline{H}_{3''}$), 2.57 (s, 3, N—C$\underline{H}_3$), 2.50 (m, 1, T1 $\underline{H}_{3'}$), 2.05–2.14 (m, 4, T1 T2 $\underline{H}_{2',2''}$), 1.79 and 1.76 (2s, 6, 2 C$\underline{H}_3$). MS FAB: M/z 510 (M+H)$^+$. Anal. Calcd. for $C_{23}H_{31}N_5O_9 \cdot H_2O$: C, 50.09; H, 6.31; N, 13.28. Found: C, 50.05; H, 6.21, N, 13.08.

Example 16

Synthesis of Phosphoramidate Containing [3'-CH$_2$—N(CH$_3$)—O—C$_2$-5'] Linked Oligonucleoside 3'-De(oxyphosphinico)-3'-[methylene(methylimino)]-5'-O-(dimethoxytriphenylmethyl)thymidylyl-(3'→5')-3'-O-(β-cyanoethyldiisopropylaminophosphiryl)thymidine The 3'-de(oxyphosphinico)-3'-[methylene (methylimino)]-thymidylyl-(3'→5') thymidine dimer of Example 15 was tritylated and phosphitylated as described in Oligonucleotide Synthesis: a practical approach, Ed. M. J. Gait, IRL Press, 1984, in an overall yield of 82%. The protected dimer was purified by silica gel column chromatography (CH$_2$Cl$_2$:MeOH:Et$_3$N; 9:1:0.1, v/v) and homogenous fractions were pooled and evaporated to furnish pure 3'-de(oxyphosphinico)-3'-[methylene(methylimino)]-thymidylyl-5'-$\underline{O}$-(dimethoxytriphenylmethyl)-(3'→5')-3'-$\underline{O}$-(β-cyanoethyldiisopropylaminophosphiryl)thymidine as a white foam (used as such for DNA synthesis). The product was isolated as a mixture of diastereoisomer: $^{31}$P NMR (CDCl$_3$) δ 149.62 and 149.11 ppm; $^1$H NMR (CDCl$_3$) δ 6.22 (pseudo t, 1, T2 $\underline{H}_{1'}$, $J_{1',2'}$=$J_{1',2''}$=6.7 Hz), 6.16 (pseudo t, 1, T1 $\underline{H}_{1'}$, $J_{1',2''}$=5.8 Hz), 2.58, 2.56 (2s, 3, N—C$\underline{H}_3$), 1.82, 1.49 (2s, 6, 2 C$\underline{H}_3$), and other protons.

The above protected phosphoramidate bearing dimer can be conveniently stored and used for coupling utilizing an automated DNA synthesizer (ABI 380B) as and when required for specific incorporation into oligomers of therapeutic value. Other dimers of the inventions, as for example but not limited the above noted methylidynenitrilo, i.e. oxime, and methyleneimino, i.e. aminohydroxy, dimers are converted to their corresponding phosphoramidate derivatives in the same manner as this example and incorporated into oligonucleotide in the standard manner as noted below. An oligomer bearing the oxime linked nucleoside dimer is reduced to an oligomer bearing a corresponding hydroxylamine linked nucleoside dimer. As noted in other examples, reduction can be effected as an CPG bound oligomer or after removal from the CPG.

Example 17

Synthesis of Intermittent (3'-CH=N—O—CH$_2$-5'), i.e. oxime; (3'-CH$_2$—NH—O—CH$_2$-5'), i.e. aminohydroxy; (3'-CH$_2$—N(CH$_3$)—O—CN$_2$-5'), i.e. N-methyl-aminohydroxy; (3'-CH$_2$—O—N (CN$_3$)—CH$_2$-5'), i.e. N-methyl-hydroxyamino; or (3'-CH$_2$—N(CN$_3$)—N(CH$_3$)—CH$_2$-5'), i.e. N,N'-dimethyl-hydrazino Linked Oligonucleosides An appropriate 2'-deoxynucleoside that will become the 3'-terminal nucleoside of an oligonucleoside is bound to a CPG column for use on an ABI 380B automated DNA synthesizer. Standard phosphoramidite chemistry program steps were employed to place the dimer bearing the (3'-CH=N—O—CH$_2$-5'), i.e. oxime; (3'-CH$_2$—NH—O—CH$_2$-5'), i.e. aminohydroxy; (3'-CH$_2$—N(CH$_3$)—O—CH$_2$-5'), i.e. N-methyl-aminohydroxy; (3'-CH$_2$—O—N(CH$_3$)—CH$_2$-5'), i.e. N-methyl-hydroxyamino; or (3'-CH$_2$—N (CH$_3$)—N(CH$_3$)—CH$_2$-5'), i.e. N,N'-dimethylhydrazino, linkages into the desired position or positions of choice within the sequence.

Example 18

Synthesis of Uniform (3'-CH=N—O—CH$_2$-5') or (3'-CH$_2$—NH—O—CH$_2$-5') Linked Oligonucleosides Via an ABI 380B DNA Synthesizer, Utilizing 3 Nucleoside Subunits Subunit 1: CPG-bound 5'-$\underline{O}$-phthalimidothymidine prepared according to the procedure of *Nucleic Acids Research*, 18:3813 (1990), and used as a 3'-terminal unit for oligonucleoside synthesis.

Subunit 2: Bifunctional (3'-$\underline{C}$-formyl and 5'-$\underline{O}$-phthalimido deoxyribonucleoside) derived by standard glycosylation of methyl 3-deoxy-3-$\underline{C}$-cyano-5-$\underline{O}$-(phthalimido)-β-$\underline{D}$-erythro-pentofuranoside with an appropriate base and DIBAL-H reduction of the nucleoside product.

Subunit 3: 5'-$\underline{O}$-DMT-3'-$\underline{C}$-formyl thymidine, employed for the incorporation of the last (the 5'-end of the oligonucleoside) nucleoside.

The automated steps of a cycle that is required to synthesize a uniform linkage (on a 10 μM scale : loading of unit 1 on CPG) are as follows:

| STEP | REAGENT/SOLVENT | Time/min |
|---|---|---|
| 1 | 5% Methylhydrazine in DCM | 10 |
| 2 | DCM:MeOH (9:1, v/v) | 5 |
| 3 | DCM wash | 2 |
| 4 | 3'-C-formyl-5'-O-phthalimido-deoxyribo-nucleoside (Unit 2, 20 μM in 20 ml of DCM) | 3 |
| 5 | DCM:Acetone (9:1, v/v): Capping | 2 |
| 6 | DCM wash | 3 |

Foregoing steps 1 through 6 are repeated for each addition of a nucleoside unit depending on desired sequence and length. The final unit is then added:

| | | |
|---|---|---|
| 8 | Final nucleoside (20 μM in 20 ml DCM) or Unit 3 | 5 |

Example 19

General and Specific NaBH$_3$CN Reduction for Conversion of (3'-CH=N—O—CH$_2$-5') Linkage to (3'-CH$_2$—NH—O—CH$_2$-5')

Reduction of a Dimer

To a solution of a dimer (0.49 g, 1 mmol) in glacial acetic acid (AcOH) (5 ml) was added sodium cyanoborohydride (0.19, 3 mmol) in AcOH (1 ml), under an argon atmosphere at room temperature. The suspension was stirred for 1 h, and an additional amount of NaBH$_3$CN in AcOH (1 ml) was added and stirring continued for 1 h. The excess of AcOH was removed under reduced pressure at room temperature. The residue was coevaporated with toluene (2×50 ml) and purified by silica gel (25 g) column chromatography. Elution with $CH_2Cl_2$:MeOH (9:1, v/v) and pooling of appropriate fractions, followed by evaporation furnished 0.36 g (75%) of solid dimer.

Reduction of an Oligonucleoside

CPG-bound oligonucleoside (1 μM), that contains one (or more) backbone modified linkages is taken off the DNA synthesizer after completion of its synthesis cycles. A 1.0 M $NaBH_3CN$ solution in THF:AcOH (10 ml, 1:1 v/v) is pumped through the CPG-bound material in a standard way utilizing a syringe technique for 30 min. The column is washed with THF (50 ml), and the reduced oligonucleoside is released from the support column in a standard way.

Alternative Reduction of an Oligonucleoside

As an alternative to the above reduction, reduction can also be accomplished after removal from the CPG support. At the completion of synthesis the oligonucleoside is removed from the CPG-support by standard procedures. The 5'-O-trityl-on oligonucleoside is purified by HPLC and then reduced by the $NaBH_3CN$/AcOH/THF method as described above.

Example 20

Synthesis of (3'-$CH_2$—N($CH_3$)—O—$CN_2$-5') Linked Oligonucleoside having a 2',3'-didehydro Nucleoside as its 5' Terminal Nucleoside 3'-De(oxyphosphinico)-2',3'-didehydro-3'-[methylene-(methylimino)]thymidylyl-(3'→5')thymidine.

To a stirred solution of 1-(5'-O-(MMTr)-β-D-glyceropentofuran-3'-ulosyl]thymine (0.13 mmol; prepared according to the procedure of T.-C. Wu, et al., *Tetrahedron*, 45:855 (1989), 5'-O-(methyleneamino)-3'-O-(t-butyldiphenylsilyl)thymidine (0.13 mmol; prepared according to the procedure of F. Debart et al. *Tet. Letters*, 33, in press, (1992), ethylene glycol (0.5 mmol), and HMPA (0.5 ml) was added $SmI_2$ in THF (0.1 mol, 3 ml, 3 mmol) at room temperature. The color of $SmI_2$ fades out as the reaction proceeds to form the desired adduct. After complete disappearance of starting materials the reaction mixture is worked-up in the usual way. (The product could be purified by silica column chromatography for characterization). The crude mixture of 3'-epimeric adduct is then alkylated ($HCHO/NaCNBH_3/AcOH$) as described in other of these examples. The methylated product is then treated with methylsulfonylchloride in pyridine to obtain a 3'-epimeric mesylate, which on base treatment would furnish the title compound.

Example 21

Synthesis of (3'-$CH_2$—$CH_2$—NH—$CH_2$-5') Linked Oligonucleoside

3'-De(oxyphosphinico)-3'-(1,2-ethanediylimino)-thymidylyl-5'-O-(t-butyldimethylsilyl)-(3'→5')-3'-O-(t-butyldiphenylsilyl)-5'-deoxythymidine To a stirred solution of aldehyde [2.5 g, 6.5 mmol, freshly prepared according to the procedure described by Fiandor, J. and Tam, S. Y., *Tetrahedron Letts.*, 33:597 (1990)], 5'-amino-3'-O-(t-butyldiphenylsilyl)-5'-deoxythymidine [3.13 g, 6.5 mmol, prepared in two steps via 3'-O-silylation of 5'-azido-5'-deoxythymidine in the manner of Hata et al. *J. Chem. Soc. Perkin I*, p. 306 (1980) and subsequently reduction of the product by the method of Poopeiko et al., *Syn. Lett.*, p. 342 (1991)], AcOH (0.39, and 6.5 mmol) in dicholoroethane (65 ml) was added followed by NaBH$(OAc)_3$ (2.759, 13.08 mmol) under argon. The suspension was stirred for 3 hours at room temperature. The reaction mixture was diluted with $CH_2Cl_2$ (250 ml) and washed with water (2×100 ml). The organic layer was dried ($MgSO_4$) and concentrated to furnish the crude product as a syrup. The product was purified by silica gel column chromatography to furnish the title compound as white foam (3.5 g, 64%). $^1$H NMR ($CDCl_3$) δ 0.1 [s, 6, Si($CH_3$)$_2$]; 0.9 and 1.1 [2s, 18, 2 Si($CH_3$)$_3$]; 1.85 and 1.95 (2s, 6, 2 $CH_3$); 2.5 (m, 2, 3"$CH_2$); 3.7 (m, 2, 5'$CH_2$); 4.0 (m, 2, 3',4'$CH$); 4.2 (m, 1, 3'$CH$); 6.05 (m, 1, 1'$H$); 6.28 (t, 1, 1'$H$); 7.1 and 7.57 (2s, 2, C6$H$); 7.35–7.7 [2m, 12, Si Ar$H$)$_2$], and other sugar protons.

3'-De(oxyphosphinico)-3'-(1,2-ethanediylimino) thymidylyl-(3'→5')-5'-deoxythymidine The protected dimer was deblocked in 81% yield following the standard procedure using (Bu)$_4$NF in THF. The deblocked dimer was purified by HPLC for analysis. $^1$H NMR (DMSO-d$_6$) δ1.76 and 1.78 (2s, 6, $CH_3$); 2.0–2.2 (3m, 4, 2'$CH_2$); 3.15 (m, 2, N$CH_2$); 3.56 (m, 2, 4'$H$, 5'$CH_2$); 4.18 (br s, 1, 3'$H$); 5.17 and 5.22 (2 br s, 2, 2 O$H$); 5.95 (t, 1, 1' $H$); 6.1 (t, 1, 1'$H$); 7.6 and 7.85 (2s, 2, 2($C_6H$)); 11.25 (br s, 2 2N$H$) and other protons.

Example 22

Synthesis of Bi-functional Nucleoside Alternate Method to that of Example 18 Subunit 2

3-Deoxy-3'-C-[(methoxyimino)methyl]-thymidine

To a stirred solution of 3'-deoxy-3'-C-formyl-5'-O-tritylthymidine (0.59, 1 mmol, prepared as per Example 4 in $CH_2Cl_2$:MeOH (2:1, 30 vol.) was added AcOH (0.5 ml) and methoxyamine hydrochloride (0.189, 2.2 mml) at room temperature. The mixture was stirred for 30 min., concentrated under vacuum and the residue dissolved in MeOH (20 ml). To this solution, concentrated HCl (0.1 ml) was added and stirred for 1 h. The solution was neutralized with $NH_4OH$ (≈2 ml) and concentrated under a vacuum to furnish the 3'-C-[(methoxyimido)methyl] derivative of thymidine. $^1$H NMR ($CDCl_3$) δ 9.67 (s, 1, N$H$); 7.67 (s, 1, $H$-6); 7.33 (d, 0.70, $H$-3" E isomer), 6.65 (d, 0.30, $H$-3' Z isomer); 6.15 (m, 1, $H$-1'); 3.60–4.12 (m, 3.3, $H$-4', $H$-5'5", $H$-3' Z isomer); 3.91 (s, 0.9, O$CH_3$ Z isomer); 3.82 (s, 2.1, O$CH_3$ oxime E isomer); 3.26 (m, 0.7, $H$-3' E isomer); 2.27–2.60 (m, 2, $H$-2',2"); 1.91 (2s, 3, $C_6CH_3$).

3'-Deoxy-3'-C-[(methoxyimino)methyl]-5-methylcytidine

The 5-methyl cytidine analogue was prepared in a like manner to the thymidine above. $^1$H NMR ($CDCl_3$) δ 7.82 (s, 0.34, $H$-6 Z isomer), 7.75 (s, 0.66, $H$-6 E isomer); 7.32 (d, 0.66, $H$-3" E isomer, J$_{3',3"}$=6.63 Hz); 6.64 (d, 0.34, $H$-3" Z isomer, J$_{3',-3"}$=6.8 Hz); 6.12 (m, 1, $H$-1); 3.50–4.15 (m, 3.34, $H$-4', $H$-5'5", $H$-3' Z isomer); 3.91 (s, 1.02, O$CH_3$) oxime Z isomer); 3.83 (s, 1.98, O$CH_3$ oxime E isomer); 3.20 (m, 0.66, $H$-3' E isomer); 2.3–2.6 (m, $H$-2',2"); 1.92 and 1.94 (2s, 3, $C_5CH_3$ E and Z isomers).

3'-Deoxy-3'-C-[(methoxyimino)methyl]-5'-O-phthalimidothymidine

3,-Deoxy-3'-C-[(methoxyimino)methyl]-thymidine on treatment with $Ph_3P$, N-hydroxyphthalimide and DEAD (Mitsunobu conditions) furnished the 5'-O-phthalimidothymidine derivative. $^1$H NMR ($CDCl_3$) δ 8.45 (br s, 1, N$H$); 7.4–8 (m, ≈5.64, aromatic $H$, $H$-6, $C_3"$ $H$=N E isomer); 6.72 (d, 0.36, $H$-3" Z isomer); 6.15 (m, 1, $H$-1'); 4.4–4.65 (m, 3, $H$-4', $H$-5',5"); 4.25 (m, 0.36, $H$-3' Z isomer); 3.92 (s, 1.08, O$CH_3$ oxime Z isomer); 3.85 (s, 1.92, O$CH_3$ oxime E isomer); 3.46 (m, 0.64, $H$-3' E isomer); 2.30–2.60 (m, 2, $H$-2', 2"); 1.97 (2s, 3, $C_5CH_3$).

3,-Deoxy-3'-C-(formylmethyloxime)-5'-phthalimido-5-methylcytidine

The 5-methyl cytidine analogue was prepared in a like manner to the thymidine above. $^1$H NMR (CDCl$_3$) δ 7.7–7.95 (m, 5, aromatic H, H-6); 7.40 (d, 0.65, H-3" E isomer; J$_{3',3''}$=5.87 Hz); 6.69 (d, 0.35, H-3" Z isomer, J$_{3',3''}$=6.3 Hz); 6.16 (m, 1, H-1'); 4.35–4.70 (m, 3, H-4', H5',5"); 4.30 (m, 0.35, H-3' Z isomer); 3.88 (s, 1.05, OCH$_3$ Z isomer); 3.81 (s, 1.95, OCH$_3$ E isomer); 3.26 (m, 0.65, H-3' E isomer); 2.30–2.65 (m, 2, H-2',2"); 2 and 1.98 (2s, C$_5$H$_3$Z and E isomers).

3'-Deoxy-3'-C-formyl-5'-O-phthalimidothymidine

3'-Deoxy-3'-C-[(methoxyimino)methyl]-5'-O-phthalimidothymidine upon treated with CH$_3$CHO in MeOH regenerated the 3'-C-formyl group. The product on purification by silica gel column chromatography furnished the title compound as homogeneous material in 81% overall yield for 3 steps. $^1$H NMR (CDCl$_3$) δ 9.95 (s, 1, CH=O); 8.62 (br s, 1, NH); 7.71–7.90 (m, 5, aromatic H, H-6); 6.06 (t, 1, H-1', J$_{1',2'}$=6.61 Hz, J$_{1',2'}$=6.6 Hz); 4.36–4.73 (m, 3, H-4', H-5',5"); 3.78 (m, 1, H-3'); 2.20–2.90 (m, 2, H-2',2"); 1.98 (s, 3, C$_5$CH$_3$).

Example 23

Synthesis of Uniform 3'-CH=N—O—CH$_2$-5' or 3'-CH$_2$—NH—O—CH$_2$-5'- or 3'-CH$_2$—N(CH$_3$)—O—CH$_2$-5' Linked Tetramer via Solution Phase Chemistry 3'→5' Elongation A standard coupling (as described in Example 12) of 3'-deoxy-3'-C-formyl-5'-O-phthalimidothymidine with 5'-O-amino-3'-O-(t-butyldiphenylsilyl)thymidine furnished 3'-de(oxyphosphinico)-3'-(methylidynenitrilo)-thymidylyl-5'-O-phthalimido-(3'→5')-3'-O-(t-butyldiphenylsilyl)thymidine. The latter product on the treatment with methylhydrazine (as described in Example 11) gave 5'-O—NH$_2$-T-3'-CH=N—O—CH$_2$-5'-T-3'-O-TBDPSi, which on another round of coupling with 5'-O-Phth-T-3'-CHO gave the trimmer 5'-O-Phth-T-3'—CH=N—O—CH$_2$-5'-T-3'-CH=N—O—CH$_2$-5'-T-3'-O-TBDPSi in an overall 83% yield. The tetramer was reduced according to Example 14 using NaBH$_3$CN/AcOH to furnish 5'-O-Tr-T-3'-CH$_2$NH—O—CH$_2$-5'-T-3'-CH$_2$—NH—O—CH$_2$-5'-T-3'-CH$_2$—NH—O—CH$_2$-5'-T-O-3'-TBDPSi. The reduced tetramer on further reductive alkylation using HCHO/NaBH$_3$CN/AcOH gave 5'-O-Tr-T-3'-CH$_2$—N(CH$_3$)—O—CH$_2$-5'-T-3'-CH$_2$—N(CH$_3$)—O—CH$_2$-5'-T-3'-CH$_2$—N(CH$_3$)—O—CH$_2$-5'-T-3'-O-TBDPSi. The methylated tetramer was finally deblocked using HCl and n(Bu)$_4$NF treatments to yield free tetramer 5'-OH-T-3'-CH$_2$—N(CH$_3$)—O—CH$_2$-5'-T-3'-CH$_2$—N(CH$_3$)—O—CH$_2$-5'-T-3'-CH$_2$—N (CH$_3$) —O—CH$_2$-5'-T-3'-OH in 79% overall yield. The tetramer was purified by HPLC utilizing a reverse phase column (Supelcosil LC18 5$_\mu$, 15 cm×4.5 cm) and elution with H$_2$O→CH$_3$CN (H$_2$O:CH$_3$CN, 95:5, 1 min; 8:2, 20 min; 7:3, 30 min; 2:8; 40 min/ml) gradient. The tetramer was eluted after 26.96 min as single isolated peak that corresponded to 86% of the total products eluted. The fractions at 26–27.5 min were pooled and lyophilized to furnish white powder. The exact molecular weight of the tetramer was determined by MS FAB: m/z 1045 (M+H)$^+$. As noted above, for the NMR data the rings are numbered from the 5' terminus to the 3' terminus. $^1$H NMR (D$_2$O, 40° C.) TOSEY (30, 100 M sec Mix)

| | | |
|---|---|---|
| Unit T$_4$ | H-1' | 6.36 |
| | H-2', 2" | 2.53 |
| | H-3' | 4.55 |
| | H-4' | 4.22 |
| | H-5', 5" | 4.04, 4.18 |
| | H-6 | 7.05 |
| Unit T$_3$ | H-1' | 6.22 |
| | H-2' | 2.52 |
| | H-2" | 2.71 |
| | H-3' | 2.90 |
| | H-3" | 2.91, 2.97 |
| | H-4' | 4.12 |
| | H-5', 5" | 4.04, 4.23 |
| | H-6 | 7.18 |
| | C$_5$CH$_3$ | 1.88 |
| Unit T$_2$ | H-1' | 6.23 |
| | H-2' | 2.52 |
| | H-2" | 2.71 |
| | H-3' | 2.91 |
| | H-3" | 2.91, 2.97 |
| | H-4' | 4.12 |
| | H-5', 5" | 4.04, 4.23 |
| | H-6 | 7.14 |
| | C$_5$CH$_3$ | 1.88 |
| Unit T$_1$ | H-1' | 6.26 |
| | H-2' | 2.54 |
| | H-2" | 2.73 |
| | H-3' | 3.03 |
| | H-3" | 3.03, 2.93 |
| | H-4' | 4.06 |
| | H-5', 5" | 4.05, 3.90 |
| | H-6 | 7.26 |
| | C$_5$CH$_3$ | 1.90 |
| | N-CH$_3$ backbone broad | 2.83 |

The above solution phase reactions can be easily transferred to an ABI 380B DNA synthesizer, utilizing 3-nucleoside sub units as described above.

Example 24

Synthesis of Monomer Unit for (3'-CH$_2$—O—N=CH-5'), (3'-CH—O—NH—CH$_2$-5') and (3'-CH$_2$—O—N(CH$_3$)—CH$_2$-5') Linkages 1-[3'-Deoxy-3'-C-(hydroxymethyl)-5'-O-(trityl)-β-D-erythropentofuranosyl]-thymine A suspension of NaBH$_4$ (1.36 g, 9.6 mmol) was added dropwise to a stirred solution of 3'-C-formyl-5'-O-tritylthymidine in EtOH:H$_2$O (22 ml, 3:1, v/v) mixture at room temperature. After 3 h, EtOAc (300 ml) was added and the organic layer was washed with H$_2$O (2×150 ml). The dried (MgSO$_4$) EtOAc extract was evaporated under reduced pressure and the residue was purified by silica gel column chromatography. Elution with CH$_2$Cl$_2$:MeOH (9:1, v/v), pooling and concentration of appropriate fractions gave the title compound (1.13 g, 83%). $^1$H-NMR (CDCl$_3$) δ 8.29 (br s, 1, NH), 7.59 (s, 1, C$_6$H) 7.47–7.22 (m, 15, TrH) 6.13 (dd, 1, H$_1$, J$_{1',2'}$=6.5 Hz); 3.98 (m, 1, H$_4$); 3.62 (m, 2, H$_3$), 3.56–3.33 (m, 2, H$_{5'}$,H$_{5''}$), 2.60 (m, 1, H$_3$); 2.33–2.20 (m, 2, H$_2$,H$_{2'}$); 1.91 (br s, 1, OH); 1.53 (S, 3, CH$_3$).

1-[3'-Deoxy-3'-C-[O-(phthalimidohydroxymethyl)]-5'-O-trityl-β-D-erythro-pentofuranosyl]-thymine Diisopropylazodicarboxylate (0.47 ml, 2.41 mmol) was added to a stirred solution of 3'-deoxy-3'-C-(hydroxymethyl)-5'-O-trityl-thymidine (0.8 g, 1.62 mmol), N-hydroxyphthalimide (0.35 g, 2.15 mmol), triphenylphosphine (0.56 g, 2.15 mmol) in dry THF (10 ml) at room temperature. After 48 h, the products were concentrated and the residue was extracted with CH$_2$Cl$_2$ (2×100 ml). The CH$_2$Cl$_2$ extracts were washed with NaHCO$_3$ (5%, 100 ml) and water (100 ml). The dried (MgSO$_4$) extract was evaporated under reduced pressure and the residue was purified by short-silica gel chromatography. Elution with EtOAC:Hexanes (1:1, v/v), pooling and concentration of appropriate fractions gave the title compound as white foam (0.82 g, 79%). $^1$H-NMR (CDCl$_3$) δ 8.24 (s, 1, N$\underline{H}$), 7.85–7.20 (m, 2O, Tr$\underline{H}$, Ar$\underline{H}$, C$_6\underline{H}$), 6.20 (m, 1, $\underline{H}_{1'}$), 4.22–4.16 (m, 3, $\underline{H}_{4'}$, $\underline{H}_{3''}$), 3.63–3.40 (m, 2, $\underline{H}_{5'}$, $\underline{H}_{5''}$), 3.02 (m, 1, $\underline{H}_{3'}$), 2.50–2.43 (m, 2, $\underline{H}_{2'}\underline{H}_{2''}$); 1.51 (s, 3, C$\underline{H}_3$). Anal. Calcd. for C$_{38}$H$_{33}$N$_3$O$_7$. 0.5 EtOAc:C, 69.86; H, 5.42, N, 6.11. Found: C, 70.19; H, 5.27; N, 5.75

1-{3'-Deoxy-3'-C-[O-(aminohydroxymethyl)]-5'-O-trityl-β-D-erythro-pentofuranosyl}-thymine Methylhydrazine (0.12 ml, 2.25 mmol) was added to a stirred solution of 3'-deoxy-3'-C-[O-(phthalimidohydroxymethyl)]-5'-$\underline{O}$-tritylthymidine (0.77 g, 1.2 mmol) in day CH$_2$Cl$_2$ (9 ml) at room temperature. After 1 h, the precipitate was filtered and the residue washed with CH$_2$Cl$_2$ (2×10 ml). The combined filtrates were concentrated and the residue was purified by silica gel column chromatography. Elution with CH$_2$Cl$_2$:MeOH (97:3, v/v), pooling and evaporation of appropriate fractions gave the title compound as white powder (0.43 g, 70%). $^1$H-NMR (CDCl$_3$) δ 8.59 (br s, 1, N$\underline{H}$), 7.66 (m, 1, C$_6$H), 7.40–7.15 (m, 15, Tr$\underline{H}$), 6.06 (pseudo t, 1, $\underline{H}_{1'}$), 5.22 (br s, 2, N$\underline{H}_2$), 3.89 (m, 1, $\underline{H}_{4'}$), 3.65–3.20 (m, 4, $\underline{H}_{5'}$, $\underline{H}_{5''}$, $\underline{H}_{3''}$), 2.81 (m, 1, $\underline{H}_{3'}$), 2.21–2.13 (m, 2, $\underline{H}_{2'}$, $\underline{H}_{2''}$), 1.37 (s, 3, C$\underline{H}_3$).

Example 25

Synthesis of (3'-CH$_2$—O—N═CH-5'), (3'-CH$_2$—O—NH—CH$_2$-5') and (3'-CH$_2$—O—N(CH$_3$)—CH$_2$-5') Linked Oligonucleosides 3'-De(oxyphosphinico)-3'-[methyleneoxy(methylimino)]thymidylyl-(3'→5')-5'-deoxythymidine A mixture of 1-[4-$\underline{C}$-formyl-3-$\underline{O}$-(t-butyldiphenylsilyl)-β-D-erythro-pentofuranosyl)thymine (1 mmol, prepared according to the procedure of *Nucleosides and Nucleotides*, 9:533 (1990)], 3'-deoxy-3'-$\underline{C}$-[($\underline{O}$-(aminohydroxymethyl)]-5'-$\underline{O}$-tritylthymidine (1 mmol), AcOH (0.1 ml), and dry CH$_2$Cl$_2$ (25 ml) was stirred at room temperature for 1 h. The solvent was evaporated and the residue was dissolved in glacial AcOH (5 ml). NaBH$_3$CN (3 mmol) was added to the stirred AcOH reaction mixture. After 1 h, an additional amount of NaBH$_3$CN (3 mmol) was added and the mixture stirred for 1 h. The reaction was concentrated under vacuum and the residue was purified by silica gel column chromatography to furnish 5'-$\underline{O}$-Tr-T-3'-CH$_2$—O—NH—CH$_2$-5'-T-3'-$\underline{O}$-TBDPSi dimer. $^1$H-NMR (CDCl$_3$) δ 8.73 (br s, 2, 2N$\underline{H}$), 7.67 (s, 1 C$_6$H), 7.674–7.23 (m, 20, Tr$\underline{H}$, TBDPh$\underline{H}$), 6.96 (s, 1, C$_6\underline{H}$), 6.23 (pseudo t, 1, T$_2$ $\underline{H}_{1'}$), 6.11 (pseudo t, 1, T$_1$, $\underline{H}_{1'}$) 5.51 (br s, 1, N$\underline{H}$), 4.16 (m, 1, T$_2\underline{H}_{3'}$) 4.02 (m, 1, T$_2$ $\underline{H}_{4'}$), 3.87 (m, 1, T$_1$ $\underline{H}_{4'}$), 3.52 (m, 3, T1 C$\underline{H}_{23''}$, T$_1$ $\underline{H}_{5''}$), 3.23 (m, 1, T$_1$ $\underline{H}_{5'}$), 2.55–2.76 (m, 3, T1 $\underline{H}_{3'}$, T2 $\underline{H}_5\underline{H}_{5''}$) 2.33–2.27 (m, 1, T2 $\underline{H}_{2'}$), 2.23–2.12 (m, 2, T1 $\underline{H}2$ $\underline{H}_{2''}$), 1.95–1.85 (m, 1, T$_2$ $\underline{H}_{2''}$), 1.83 (s, 3, C$\underline{H}_3$) 1.45 (s, 3, C$\underline{H}_3$), 1.06 (s, 9, (C$\underline{H}_3$)$_3$CSi).

The latter dimer was methylated using HCHO/NaBH$_3$CN/AcOH and finally deblocked with nBu$_4$NF/THF and HF/CH$_3$CN in two-steps to furnish the title compound (65% yield). $^1$H-NMR (DMSO-d$_6$) δ 11.27 (br s, 2, N$\underline{H}$); 7.85 (s, 1, T1 C$_6$H); 7.51 (s, 1, T$_2$ C$_6\underline{H}$); 6.15 (pseudo t, 1, T$_2$ $\underline{H}_{1'}$, J$_{1'-2'}$=7.8 Hz, J$_{1'-2''}$=6.3 Hz); 6.00 (pseudo t, 1, T$_1$ $\underline{H}_{1'}$, J$_{1'-2''}$=6.9 Hz, J$_{1'-2''}$=4.5 Hz), 5.32 (br s, 1, O$\underline{H}_{3'}$), 5.09 (br s, 1, O$\underline{H}_{5'}$); 4.17 (m, 1, T$_2$ $\underline{H}_{3'}$); 3.90 (m, 1, T$_2$ $\underline{H}_{4'}$); 3.76–3.66 (m, 4, T$_1$ $\underline{H}_{4'}$, T$_1$ $\underline{H}_{5'}$, C$\underline{H}_{2\ 3''}$); 3.60–3.52 (m, 1, T$_1$ $\underline{H}_{5''}$); 2.82 (m, 2, T$_2$ $\underline{H}_{5'}$, $\underline{H}_{5''}$); 2.57 (s, 3, N—C$\underline{H}_3$); 2.47 (m, 1, T$_1\underline{H}_{3'}$); 2.23–2.02 (m, 4, $\underline{H}_{2'}\underline{H}_{2''}$) 1.81 (s, 3, C$_5$C$\underline{H}_3$); 1.78 (s, 3, C$_5$ C$\underline{H}_3$). Anal. Calcd. for C$_{22}$H$_{31}$N$_5$O$_9$.0.5 H$_2$O: C, 50.96; H. 6.22; N, 13.50. Found: C, 51.01; H, 6.22; N, 13.19. MS (FAB+, glycerol) M+H$^+$ m/z=510.

Example 26

Synthesis of Phosphoramidate Containing (3'-CH$_2$—O—N(CH$_3$)—CH$_2$-5') Linked Oligonucleoside 3'-De(oxyphosphinico)-3'-[methyleneoxy(methylimino)]-thymidylyl-5'-O-(dimethyoxytriphenylmethyl)-(3'→5')-3'-(O-β-cyanoethyldiisopropylaminophosphiryl)thymidine Dimethyoxytritylation of the dimer 5'-OH-T-3'-CH$_2$—O—NCH$_3$—CH$_2$-5'-T-3'-OH following the procedure described in oligonucleotide Synthesis: a practical approach, Ed. M. J. Gait, IRL Press, 1984, furnished the 5'-$\underline{O}$-DMTr protected dimer as white foam. $^1$H-NMR (CDCl$_3$) δ 7.67 (s, 1, $\underline{H}_6$); 7.44–6.82 (m, 14, $\underline{H}_6$, DMTr$\underline{H}$); 6.20 (pseudo t, 2, $\underline{H}_{1'}$); 4.3 (m, 1, T$_2\underline{H}_{3'}$); 4.15 (m, 1, T$_2$ $\underline{H}_{4'}$); 4.00 (m, 1, T$_1$ $\underline{H}_{4'}$); 3.80 (s, 6, OC$\underline{H}_3$); 3.77–3.23 (m, 4, T$_1$ $\underline{H}_{5'}$ $\underline{H}_{5''}$, CH$_{2\ 3''}$); 2.89–2.50 (m, 3, T$_2$ $\underline{H}_{5'}\underline{H}_{5''}$, T1 $\underline{H}_{3'}$); 2.62 (s, 3, N—C$\underline{H}_3$); 2.48–2.08 (m, 4, $\underline{H}_{2'}\underline{H}_{2''}$); 1.9 (s, 3, C$_5$C$\underline{H}_3$) 1.48 (s, 3 C$_5$C$\underline{H}_3$).

Above compound was phosphitylated following the procedure described in Oligonucleotide Synthesis: a practical approach, Ed. M. J. Gait, IRL Press, 1984, to furnish the title compound in 70% yield over two steps as white powder. $^1$H NMR (CDCl$_3$) δ 8.25 (br s, 2, N$\underline{H}$), 7.66 (s, 1, C$_6\underline{H}$), 7.15–7.45 (m, 10, Ar$\underline{H}$, C$_6\underline{H}$), 6.8–6.9 (m, 4, Ar$\underline{H}$), 6.12 (m, 2, 2C$_1\underline{H}$), 3.79 (s, 6, ArOC$\underline{H}_3$), 2.56 (s, 3, N—C$\underline{H}_3$), 1.88, 1.44 (2s, 6, 2 C$_5$ C$\underline{H}_3$) and other protons. $^{31}$P NMR (CDCl$_3$) 149.42 and 148.75 ppm.

Example 27

Synthesis of Oligonucleosides having Linkages that Include Pharmacokinetic and Pharmacodynamic Property Modifying Groups Located Therein On 3'-De(oxyphosphinico)-3'-[methylene(benzylimino)]-thymidylyl-5'-O-(dimethyoxytriphenylmethyl)-(3'→5')-3'-O-β-(cyanoethyldiisopropylaminophosphiryl)thymidine A reductive coupling of 3'-deoxy-3'-$\underline{C}$-formyl-5'-$\underline{O}$-tritylthymidine (1.5 mmol) with 5'-$\underline{O}$-amino-3'-$\underline{O}$-(t-butyldiphenylsilyl)thymidine (1.5 mmol) as described in Example 12 furnished 5'-$\underline{O}$-Tr-T-3'-CH$_2$—NH—O—CH$_2$-5'-T-3'-$\underline{O}$-TBDPSi dimer. This dimer was benzylated with C$_6$H$_5$CHO/NaBH$_3$CN/AcOH in the same manner as the above described methylation to yield N-benzylated dimer 5'-$\underline{O}$-Tr-T-3'-CH$_2$-NBz-O—CH$_2$-5'-T-3'-$\underline{O}$-TBDPSi. The latter dimer was deblocked using nBu$_4$NF/THF and HCl/MeOH methodology as described in above examples to furnish deblocked dimer 5'-OH-T-3'-CH$_2$-NBn-O—CH$_2$-5'-T-3'-OH, which on dimethoxytritylation and subsequent phosphitylation following the procedure described in Oligonucleotide Synthesis: a practical approach, Ed. M. J. Gait, IRL Press, 1984, gave the title compound (45% overall yield). $^1$H NMR (CDCl$_3$) δ 6.15 (pseudo t, 1, T2 C$_1\underline{H}$); 6.09 (m, 1, T1 C$_1\underline{H}$); 3.76 (s, 6, 2OC$\underline{H}_3$); 1.7 and 1.48 (2S, 6, 2-C $\underline{H}_3$) and other protons. $^{31}$p NMR (CDCl$_3$) 149.59 and 149.23 ppm.

The phosphiltylated dimer was successfully incorporated into an oligomer using an automated DNA synthesizer in the manner of Example 8 illustrating the ability to attach of various pharmacokinetic and pharmacodynamic property modifying groups into the backbone linkage prior to the DNA synthesis of an oligonucleotide.

Example 28

Of (3'-CH$_2$—NH—CH$_2$—CH$_2$-5'), (3-CH$_2$—N(CH$_3$) —CH$_2$—CH$_2$-5'), and Phosphoramidate Derivative 3'-De(oxyphosphinico-3'-[(methyleneimino)methylene]-5'-O-(dimethyoxytrityl)thymidylyl-(3'→5')-thymidine A reductive amination [according to the procedure of A. F. Abdel-Magid et al., *Tetrahedron Letts.* 31:5595 (1990)] of 3'-deoxy-3'-C-formyl-5'-O-tritylthymidine (1 mmol) with 1-[6'-amino-2',5',6'-trideoxy-3'-O-(t-butyldiphenylsilyl)-β-D-erythro-hexofuranosyl]thymine [1.2 mmol, prepared according to the procedure of G. Et Zold et al., *J.C.S. Chem. Comms.*, 422 (1968)] in presence of AcOH gave a blocked dimer 5'-O-Tr-T-3'-CH$_2$NH—CH$_2$—CH$_2$-5'-T-3'-O-TBDPSi, which on deprotection as described in above examples gave 5'-OH-T-3'-CH$_2$—NH—CH$_2$—CH$_2$-5'-T-3'-OH dimer as white powder (70% yield). $^1$H NMR (D$_2$O), pH 5.6, 20° C.) δ T1 thymidine unit: 7.78 (s, 1, C$_6$H); 6.17 (t, 1, C$_1$ H); 4.45 (m, 1, C$_3$H); 4.08 (m, 1, C$_4$H); 4.00, 3.72 (m, 2, C$_{5',5''}$H); 2.9 (m, 2 C$_{6',6''}$H); 2.34 (m, 2, C$_{2',2''}$H); 1.77 (s, 3, CH$_3$); T2 thymidine unit: 7.47 (s, 1 C$_6$H); 6.07 (t, 1, C$_1'$ H); 3.89 (m, 2, C$_{5',5''}$H); 3.79 (m, 1, C$_4$H); 2.89 (m, 1, C$_{3''}$ H); 2.38 (m, 1, C$_2$H); 2.32 (m, 1, C$_3$H); 1.72 (s, 3, CH$_3$); and 2.68 (s, N—CHhd 3).

Pka Determination:

The sensitivity of the proton chemical shift of the N-Me group of the foregoing dimer to change in response to change in pH was measured by NMR as an indicator of the pka of the backbone amine. The chemical shift moved downfield as the amino group was protonated. A 4 mg sample of 5'-OH-T-3'-CH$_2$—NCH$_3$—CH$_2$—CH$_2$-5'-T-3'-OH dimer was dissolved in 0.6 ml of 30 mM bicarbonate buffer. The pH was varied between 5.1 and 10.0 using 0.1 N NaOH in 6-steps. The chemical shift of the N-methyl proton varied between 2.26 and 2.93 ppm, giving rise to a pka of 7.8±0.1. While we do not wish to be bound by theory, it is thus believed that at physiological pH this backbone will be protonated.

3'-De(oxyphosphinico-3'-[methylene(methylimino)methylene]-5'-O-(dimethyoxytrityl)-thymidylyl-(3'→5')-3'-O-(β-cyanoethyldiisopropylaminophosphiryl)thymidine The proceeding diner was methylated using HCHO/NaBH$_3$CN in AcOH to furnish 5'-OH-T-3'-CH$_2$—N(CH$_3$)—CH$_2$—CH$_2$-5'-T-3'-OH dimer, which on dimethoxytritylation and phosphitylation following the procedure described in Oligonucleotide Synthesis: a practical approach, Ed. M. J. Gait, IRL Press, 1984, gave the title compound as foam (68% yield). $^1$H NMR (CDCl$_3$) δ 6.12 (m, 2, 2C$_1'$ H) ; 2.15, 2.14 (2s, 3, N—CH$_3$); 1.88, 1.45 (2s, 6, 2 C$_5$CH$_3$) and other protons. $^{31}$P NMR (CDCl$_3$) 149.49 and 148.96 ppm.

Example 29

A (3'-CN$_2$—N(Labile Blocking Group)-O—CH$_2$-5') Dimer and Phosphoramidate Derivative—a Dimer Incorporating a 3'-de(oxyphosphinico)-3'-(methyleneimino) (3→5') Linkage Having a Labile N-protecting Group for Regeneration of a (3'-CH$_2$—NH—O—CH$_2$-5) Linkage 3'-De(oxyphosphinico)-3'-[methylene(phenoxyacetylimino)]-thymidylyl-(3'→5')-thymidine To a stirred solution of 5'-O-Tr-T-3'-CH$_2$—NH—O—CH$_2$-5'-T-3'-O-TBDPSi (1 mmol, prepared according to the procedure of F. Debart et al. *Tetrahedron Letts.*, 33:in press 1992) in dry pyridine (10 ml) was added phenoxyacetylchloride (1.2 mmol). After 12 h, the products were diluted with CH$_2$Cl$_2$ (200 ml) and washed with sat. NaHCO$_3$ (2×50 ml), water (2×50 ml) and dried (MgSO$_4$). The CH$_2$Cl$_2$ extract was concentrated and residue purified by silica gel column chromatography. Elution with CH$_2$Cl$_2$: MeOH (9:1, v/v), pooling of appropriate fractions and evaporation furnished 5'-O-Tr-T-3'-CH$_2$—N(COCH$_2$OPh)—O—CH$_2$-5'-T-3'-O-TBDPSi dimer as white foam. $^1$H NMR (DMSO-d$_6$) δ 11.35 (br s, 2, NH); 7.6–6.65 (m, 32, Tr, TBDPS, phenoxyacetyl, C$_6$H); 6.3 (pseudo t, 1, H$_{1'}$); 6.03 (pseudo t, 1, H$_{1'}$); 4.5 (m, 2, CH$_2$); 4.3 (m, 1, T$_2$ H$_3$); 3.9–3.3 (m, 6, T$_1$ H$_{4'}$, T$_2$H$_{4'}$, T$_2$ H$_{4'}$, T$_2$H$_{5'}$, H$_{5''}$, CH$_{2\ 3''}$); 3.10 (m, 2, T, H$_{5'}$, H$_{5''}$); 2.65 (m, 1, T$_1$ H$_3$); 2.2–2.05 (m, 4, H$_{2'}$, H$_{2''}$); 1.58 (s, 3, C H$_3$); 1.4 (s, 3, CH$_3$); 1.02 (s, 9, (CH$_3$)$_3$CSi).

The foregoing dimer was sequentially deblocked with HF (48%)/CH$_3$CN (5:95, v/v) treatment to remove the trityl group, and the product on treatment with nBu$_4$NF/THF removed the silyl group to furnish title compound as white powder (70% yield for 3-steps). $^1$H NMR (DMSO-d$_6$) δ 11.35 (br s, 1, NH); 11.25 (br s, 1, NH) 7.92 (s, 1, C$_6$H); 7.5 (s, 1, C$_6$H); 7.2–6.8 (m, 5, ArH); 6.23 (pseudo t, 1, H$_{1'}$); 5.98 (dd, 1, H$_{1'}$); 5.45 (d, 1, OH$_{3'}$), 5.15 (t, 1, OH$_{5'}$); 4.9 (m, 2, C H$_2$); 4.3–3.5 (m, 9, T$_2$ H$_{3'}$, H$_{4'}$, H$_{5'}$H$_{5''}$, CH$_{23''}$); 2.6 (m, 1, T$_1$ H$_{3'}$); 2.25–2.00 (m, 4, H$_{2'}$H$_{2''}$); 1.75 (s, 3, CH$_3$); 1.65 (s, 3, CH$_2$).

The latter dimer was dimethoxytritylated as per the procedure of described in Oligonucleotide Synthesis: a practical approach, Ed. M. J. Gait, IRL Press, 1984, to furnish 5'-O-DMT-T-3'-CH$_2$—N—(COCH$_2$OPh)—O—CH$_2$-5'-T-3'-OH as pale yellow colored foam. $^1$H NMR (DMSO d$_6$) δ 11.3 (br s, 2, NH); 7.55 (s, 1, C$_6$H). 7.45 (s, 1, C$_6$H); 7.38–6.75 (m, 18, DMTrH, phenoxyacetyl-H); 6.22 (pseudo t, 1, T$_2$ H$_{1'}$); 6.05 (pseudo t, 1, T$_1$H$_{1'}$); 4.75–4.60 (m, 2, CH$_2$); 4.25 (m, 1, T$_2$ H$_{5'}$); 4.18 (m, 1, T$_2$ H$_{3'}$); 4.05 (m, 1, T$_2$ H$_{5''}$); 3.9 (m, 2, H$_{4'}$); 3.8–3.6 (m, 2, CH$_{2\ 3''}$); 3.65 (s, 6, 2OCH$_3$) 3.2 (m, 2, T$_1$, H$_5$H$_{5''}$) 2.82 (m, 1, T$_1$ H$_{3'}$); 2.3–2.05 (m, 4, H$_{2'}$H$_{2''}$); 1.6 (s, 3, T$_2$ CHCH$_3$); 1.38 (s, 3, T1 CH$_3$).

The above dimer on phosphitylation following the procedure described in Oligonucleotide Synthesis: a practical approach, Ed. M. J. Gait, IRL Press, 1984, furnished the phosphoramidate derivatized dimer (appropriate for use on DNA synthesizer) as a foam (75% in 2 steps). $^1$H NMR (CDCl$_3$) δ 7.62 (s, 1, C$_6$H); 7.2–7.45 (2m, 12, ArH); 6.77–7.05 (3m, 7, ArH, C$_6$H); 6.15 (pseudo t, 1, C$_1$H); 6.05 (t, 1, C$_1$H); 4.7 (m, 2, 2C$_4$H); 3.74 (2s, 6, 2ArOCH$_3$); 2.95 (m, 1, C$_3$H); 1.78, 1.77 (2s, 3, C$_5$CH$_3$); 1.41 (s, 3, C$_5$CH$_3$), and other protons. $^{31}$P NMR (CDCl$_3$) 1.49.76 and 149.56 ppm.

Example 30

Regeneration of (3'-CH$_2$—NH—O—CH$_2$-5') Linkage from (3'-CH$_2$—N(Labile Blocking Group)—CH$_2$—CH$_2$-5') Linkage in an Oligonucleotide The phosphitylated dimer of Example 29 will be incorporated within an oligonucleotide as per the procedure of Example 8. After completion of the oligonucleotide on the support, the oligonucleotide is cleaved from the support utilizing standard ammonium hydroxide conditions. Concurrent with the cleavage from the support the ammonium hydroxide treatment will further cleave the phenoxyacetyl blocking group from the imino nitrogen of the incorporated (3'-CH$_2$—N(COCH$_2$OPh)—O—CH$_2$-5') oligonucleoside dimer to yield the (3'-CH$_2$—NH—O—CH$_2$-5') linked oligonucleoside dimer within the oligonucleotide structure.

Example 31

Synthesis of (3'-CH$_2$—P(O)$_2$—O—CH$_2$-5') and (3'-CH$_2$—O—P(O)$_2$—CH$_2$-5') Linked Oligonucleosides Synthesis of 3'-C-phosphonate Dimer 3'-hydroxymethyl-5'-O-(t-butyldiphenylsilyl)thymidine will be converted into its bromide by treatment with NBS.

The bromide is subjected to an Arbuzov reaction to furnish the phosphonate diester. Cleavage of the phosphonate diester with trimethylbromosilane gives the free acid which on treatment with 3'-O-(t-butyldiphenylsilyl)thymidine and DCC in pyridine yields the dimer.

Synthesis of 3'-C-phosphonate Linked Oligonucleosides

The above dimer will be incorporated into an oligonucleoside by suitably protecting and activating the dimer as the 5'-O-DMT and 3'-O-phosphoramide derivative for insertion into desired locations in oligonucleosides by standard DNA synthesizer chemistry.

Synthesis of 5'-C-phosphonate Linked Oligonucleosides

The corresponding 5'-C-phosphonate dimers will be obtained by a reacting a 5'-deoxy-5'-bromonucleoside with a phosphite ester resulting in a 5'-phosphonate. This in turn is reacted with a 3'-hydroxymethyl nucleoside to yield the 5'-C-phosphonate linked dimer.

Evaluation

Procedure 1—Structure and Integrity of Oligonucleotides

A. Digest of Oligonucleotides

Enzymatic Digestion of Oligonucleotides

The incorporation of backbone modification as in various antisense oligonucleotides was proved by enzymatic hydrolysis using following protocol. In the sequence listing of this procedure a "*" is used to denote the positioning of a linkage of the invention within the sequence and in a like manner a "p" is used to denote the positioning of a normal phosphodiester linkage.

The modified oligonucleotide (5'-GpCpGpTpTpTpTpT*TpTpTpTpTpGpCpG-3') (0.2 OD at $A_{260}^{nm}$) was dissolved in 0.1M tris-HCl buffer (pH 8.3 200 µl) and treated with snake venom phosphodiesterase (0.4 µg), alkaline phosphatase (0.4 µg), and calf spleen phosphodiesterase (0.4 µg) for 24–60 h at 37° C. The resulting mixture was diluted and analyzed by HPLC. Column: C-18 Nucleosil (5 µ). Flow rate: 1 ml/min. Solvent A: 10 mM triethylammonium acetate, Solvent B: acetonitrile/water (1:1). A 20 min. linear gradient from 0% B to 50% B. Quantification of the material was made on the basis of the peak areas which were directed by the extinction coefficients of the nucleoside constituents. The identity of each modified backbone containing dimer was proved by co-injecting a synthetic sample with fully digested oligonucleotide. In all cases, integration of the peaks of HPLC analyses demonstrated the correct gross composition of the digested oligonucleotide.

B. Integrity of Backbone Linkage

In addition, the integrity of each incorporation of modified backbone was further supported by $^1$H and $^{31}$p NMR analyses of a CpT*TpG tetramer prepared on the same ABI 380B DNA synthesizer. Thus, indirectly validating the computer program on the synthesizer.

Procedure 2—Hybridization Analysis.

The relative ability of an oligonucleotide, an oligonucleotide analogue or oligonucleoside of the invention to bind to complementary nucleic acids can be compared by determining the melting temperature of a particular hybridization complex. The melting temperature ($T_m$), a characteristic physical property of complementary nucleic acids, denotes the temperature in degrees centigrade at which 50% double helical versus coil (unhybridized) forms are present. $T_m$ is measured by using the UV spectrum to determine the formation and breakdown (melting) of hybridization. Base stacking, which occurs during hybridization, is accompanied by a reduction in UV absorption (hypochromicity). Consequently a reduction in UV absorption indicates a higher $T_m$.

The higher the $T_m$, the greater the strength of the binding of the strands. Non-Watson-Crick base pairing has a strong destabilizing effect on the $T_m$. Consequently, absolute fidelity of base pairing is necessary to have optimal binding of an antisense oligonucleotide or oligonucleoside to its targeted RNA.

A. Evaluation of the Thermodynamics of Hybridization of Oligonucleotide Analogues.

The ability of selected oligonucleotide analogues of the invention to hybridize to their complementary RNA or DNA sequences was determined by thermal melting analysis. The RNA complement was synthesized from T7 RNA polymerase and a template-promoter of DNA synthesized with an Applied Biosystems, Inc. 380B nucleic acid synthesizer. The RNA species is purified by ion exchange using FPLC (LKB Pharmacia, Inc.). Antisense oligonucleotide analogues are added to either the RNA or DNA complement at stoichiometric concentrations and the absorbance (260 nm) hyperchromicity upon duplex to random coil transition monitored using a Gilford Response II spectrophotometer. These measurements are performed in a buffer of 10 mM Na-phosphate, pH 7.4, 0.1 mM EDTA, and NaCl to yield an ionic strength of either 0.1 M or 1.0 M. Data can be analyzed by a graphic representation of $1/T_m$ vs ln[Ct], where [Ct] is the total oligonucleotide concentration.

The results of thermodynamic analysis of the hybridization of selected oligonucleotide analogues of the invention are shown in Table 1. In the sequence listing of this table a "*" is used to denote the positioning of a linkage of the invention within the sequence and in a like manner a "p" is used to denote the positioning of a normal phosphodiester linkage. Further in this table and in following tables various backbone linkages of the invention are cross referenced between generic chemical names and short hand structures as follows: (3'-CH=N—O—CH$_2$-5') is denoted as oxime; (3'-CH$_2$—NH—O—CH$_2$-5') is denoted as aminohydroxy; (3'-CH$_2$—N(CH$_3$)—O—CH$_2$-5') is denoted as N-methyl-aminohydroxy; (3'-CH$_2$—O—N(CH$_3$)—CH$_2$-5') is denoted as N-methyl-hydroxyamino; and (3'-CH$_2$—N(CH$_3$)—N(CH$_3$)—CH$_2$-5') is denoted as N,N'-dimethylhydrazino.

TABLE 1

DUPLEX STABILITY (DNA-RNA)

| * BACKBONE | $T_m$ ° C. | $\Delta T_m$ ° C. |
|---|---|---|
| SEQUENCE = 5'- GpCpGpTpTpTpT*TpTpTpTpTpGpCpG -3' | | |
| Natural | 50.2 | |
| N-Methyl-Hydroxyamino | 48.9 | −1.3 |
| N-Methyl-Aminohydroxy | 49.4 | −0.8 |
| N,N'-Dimethyl-Hydrazino | 48.3 | −1.9 |
| Aminohydroxy | 47.8 | −2.4 |
| SEQUENCE = 5'- GpCpGpTpTpTpT*TpT*TpTpTpGpCpG -3' | | |
| Natural | 50.2 | |
| N-Methyl-Hydroxyamino | 47.5 | −2.7 |
| N-Methyl-Aminohydroxy | 49.7 | −0.5 |
| N,N'-Dimethyl-Hydrazino | 48.6 | −1.6 |
| Aminohydroxy | 43.7 | −6.4 |
| SEQUENCE = 5'- GpCpGpTpTpT*TpT*TpT*TpTpGpCpG -3' | | |
| Natural | 50.2 | |
| N-Methyl-Hydroxyamino | 44.2 | −6.0 |
| N-Methyl-Aminohydroxy | 48.2 | −1.9 |
| N,N'-Dimethyl-Hydrazino | 49.0 | −1.2 |
| Aminohydroxy | 45.3 | −4.9 |
| SEQUENCE = 5'- GpCpGpT*TpTpT*TpTpT*TpT*TpGpCpG -3' | | |
| Natural | 50.2 | |
| N-Methyl-Aminohydroxy | 47.8 | −2.4 |

TABLE 1-continued

DUPLEX STABILITY (DNA-RNA)

| * BACKBONE | T_m ° C. | ΔT_m ° C. |
|---|---|---|
| SEQUENCE = 5'- GpCpGpTpT*TpT*TpT*TpT*TpTpGpCpG -3' | | |
| Natural | 50.2 | |
| N-Methyl-Hydroxyamino | 42.3 | −7.9 |
| Aminohydroxy | 45.5 | −4.7 |
| SEQUENCE = 5'- GpCpGpT*TpTpT*TpT*TpTpT*TpGpCpG -3' | | |
| Natural | 50.2 | |
| N-Methyl-Aminohydroxy | 47.9 | −2.3 |
| N,N'-Dimethyl-Hydrazino | 47.3 | −2.8 |
| Aminohydroxy | 43.9 | −6.3 |
| SEQUENCE = 5'- GpCpGpT*TpT*TpT*TpT*TpT*TpGpCpG -3' | | |
| Natural | 50.2 | |
| N-Methyl-Hydroxyamino | 40.0 | −10.2 |
| N-Methyl-Aminohydroxy | 50.8 | +0.64 |
| N,N'-Dimethyl-Hydrazino | 51.3 | +1.1 |
| Aminohydroxy | 44.2 | −6.0 |
| SEQUENCE = 5'- CpTpCpGpTpApCpCpT*TpTpCpCpGpGpTpCpC -3' | | |
| Natural | 63.4 | |
| Oxime | 60.2 | −3.2 |
| N-Methyl-Aminohydroxy | 64.9 | +1.5 |
| N,N'-Dimethyl-Hydrazino | 64.9 | +1.5 |
| Aminohydroxy | 62.9 | −0.5 |
| SEQUENCE = 5'- CpTpCpGpTpApCpT*TpT*TpCpCpGpTpCpC -3' | | |
| Natural | 56.7 | |
| N-Methyl-Hydroxyamino | 54.3 | −2.4 |
| N-Methyl-Aminohydroxy | 57.4 | +0.7 |
| N,N'-Dimethyl-Hydrazino | 57.0 | +0.3 |
| Aminohydroxy | 56.0 | −0.7 |
| SEQUENCE = 5'- CpGpApCpTpApTpGpCpApApTpT*TpC -3' | | |
| Natural | 44.1 | |
| Oxime | 41.6 | −2.5 |
| N-Methyl-Hydroxyamino | 43.8 | −0.3 |
| N-Methyl-Aminohydroxy | 43.6 | −0.5 |
| N,N'-Dimethyl-Hydrazino | 42.8 | −1.3 |
| Aminohydroxy | 43.4 | −0.7 |

In a further study, the base pair specificity of oligonucleotide having modified linkages of the invention was studied. The study measure binding of the 5'-T of T*T dimer in the sequence 5'-CpTpCpGpTpApCpCpT*TpTpCpCpGpGpTpCpC-3'
when matched to A in the RNA complement (a T:rA pair) as compared to mismatch with C, G or U. The average of the mismatch of all the base pairs is shown in Table 2. Table 2 demonstrates that the essential Watson-Crick base pair specificy of the backbone linkages of the invention to complementary strand is not compromised.

TABLE 2

BASE PAIR SPECIFICITY
5'- CpTpCpGpTpApCpCpT*TpTpCpCpGpGpTpCpC -3'

| * BACKBONE | ΔT_m/mismatch |
|---|---|
| Natural | −5.5 |
| Oxime | −4.95 |
| N-Methyl-Aminohydroxy | −7.32 |
| N,N'-Dimethyl-Hydrazino | −7.41 |
| Aminohydroxy | −6.89 |

B. Fidelity of Hybridization of Oligonucleotide Analogues

The ability of the antisense oligonucleotide analogues of the invention to hybridize with absolute specificity to a targeted mRNA can be shown by Northern blot analysis of purified target mRNA in the presence of total cellular RNA. Target mRNA is synthesized from a vector containing the cDNA for the target mRNA located downstream from a T7 RNA polymerase promoter. Synthesized mRNA is electrophoresed in an agarose gel and transferred to a suitable support membrane (i.e. nitrocellulose). The support membrane is blocked and probed using [$^{32}$P]-labeled oligonucleotide analogues. The stringency is determined by replicate blots and washing in either elevated temperatures or decreased ionic strength of the wash buffer. Autoradiography is performed to assess the presence of heteroduplex formation and the autoradiogram quantitated by laser densitometry (LKB Pharmacia, Inc.). The specificity of hybrid formation is determined by isolation of total cellular RNA by standard techniques and its analysis by agarose electrophoresis, membrane transfer and probing with the labelled oligonucleotide analogues. Stringency is predetermined for an unmodified antisense oligonucleotide and the conditions used such that only the specifically targeted mRNA is capable of forming a heteroduplex with the oligonucleotide analogue.

Procedure 3—Nuclease Resistance

A. Evaluation of the Resistance of Oligonucleotide Analogues to Serum and Cytoplasmic Nucleases.

Oligonucleotide analogues of the invention can be assessed for their resistance to serum nucleases by incubation of the oligonucleotide analogue in media containing various concentrations of fetal calf serum. Labeled oligonucleotide analogues are incubated for various times, treated with protease K and then analyzed by gel electrophoresis on 20% polyacrylamine-urea denaturing gels and subsequent autoradiography. Autoradiograms are quantitated by laser densitometry. Based upon the location of the modified linkage and the known length of the oligonucleotide it is possible to determine the effect on nuclease degradation by the particular modification. For the cytoplasmic nucleases, an HL 60 cell line can be used. A post-mitochondrial supernatant is prepared by differential centrifugation and the labelled oligonucleotide analogues are incubated in this supernatant for various times. Following the incubation, the oligonucleotide analogues are assessed for degradation as outlined above for serum nucleolytic degradation. Autoradiography results are quantitated for comparison of the unmodified and the oligonucleotide analogues of the invention.

Table 3 shows the nuclease resistance of certain of the linkages of the invention to 10% fetal calf serum. As is evident from Table 3, all of the linkages tested exhibit greater stability to nucleases of the fetal calf serum compare to natural nucleotides. In Table 3 the $t_{1/2}$ of both the N to N−1 transition and the N−1 to the N−2 transition are shown. In the sequence listing of this table a "*" is used to denote the place of a linkage of the invention within the sequence and in a like manner a "p" is used to denote a normal phosphodiester linkage.

TABLE 3

NUCLEASE RESISTANCE (10%) Fetal Calf Serum
SEQUENCE = 5'- CpGpApCpTpApTpGpCpApApTpT*TpC -3'

| | $t_{1/2}$ | |
|---|---|---|
| * BACKBONE | N → N-1 | → N-2 |
| Natural | 0.5 hr | 1.0 hr |
| N-Methyl-Hydroxyamino | 2.0 hr | 4.0 hr |
| N-Methyl-Aminohydroxy | 5.5 hr | 12.5 hr |

TABLE 3-continued

NUCLEASE RESISTANCE (10%) Fetal Calf Serum
SEQUENCE = 5'- CpGpApCpTpApTpGpCpApApTpT*TpC -3'

| * BACKBONE | $t_{1/2}$ N → N-1 | → N-2 |
|---|---|---|
| N,N'-Dimethyl-Hydrazino | 20.5 hr | 36.5 hr |
| Aminohydroxy | 2.5 hr | |

Procedure 4—5-Lipoxygenase Analysis, Therapeutics and Assays

A. Therapeutics

For therapeutic use, an animal suspected of having a disease characterized by excessive or abnormal supply of 5-lipoxygenase is treated by administering oligonucleotide analogues in accordance with this invention. Persons of ordinary skill can easily determine optimum dosages, dosing methodologies and repetition rates. Such treatment is generally continued until either a cure is effected or a diminution in the diseased state is achieved. Long term treatment is likely for some diseases.

B. Research Reagents

The oligonucleotide analogues of this invention will also be useful as research reagents when used to cleave or otherwise modulate 5-lipoxygenase mRNA in crude cell lysates or in partially purified or wholly purified RNA preparations. This application of the invention is accomplished, for example, by lysing cells by standard methods, optimally extracting the RNA and then treating it with a composition at concentrations ranging, for instance, from about 100 to about 500 ng per 10 Mg of total RNA in a buffer consisting, for example, of 50 mm phosphate, pH ranging from about 4–10 at a temperature from about 30 °to about 50° C. The cleaved 5-lipoxygenase RNA can be analyzed by agarose gel electrophoresis and hybridization with radiolabeled DNA probes or by other standard methods.

C. Diagnostics

The oligonucleotide analogues of this invention will also be useful in diagnostic applications, Particularly for the determination of the expression of specific mRNA species in various tissues or the expression of abnormal or mutant RNA species. In this example, the oligonucleotide analogues target a hypothetical abnormal mRNA by being designed complementary to the abnormal sequence, but would not hybridize to or cleave the normal mRNA.

Tissue samples can be homogenized, and RNA extracted by standard methods. The crude homogenate or extract can be treated for example to effect cleavage of the target RNA. The product can then be hybridized to a solid support which contains a bound oligonucleotide complementary to a region on the 5' side of the cleavage site. Both the normal and abnormal 5' region of the mRNA would bind to the solid support. The 3' region of the abnormal RNA, which is cleaved by the invention compound, would not be bound to the support and therefore would be separated from the normal mRNA.

Targeted mRNA species for modulation relates to 5-lipoxygenase; however, persons of ordinary skill in the art will appreciate that the present invention is not so limited and it is generally applicable. The inhibition or modulation of production of the enzyme 5-lipoxygenase is expected to have significant therapeutic benefits in the treatment of disease. In order to assess the effectiveness of the compositions, an assay or series of assays is required.

D. In Vitro Assays

The cellular assays for 5-lipoxygenase preferably use the human promyelocytic leukemia cell line HL-60. These cells can be induced to differentiate into either a monocyte like cell or neutrophil like cell by various known agents. Treatment of the cells with 1.3% dimethyl sulfoxide, DMSO, is known to promote differentiation of the cells into neutrophils. It has now been found that basal HL-60 cells do not synthesize detectable levels of 5-lipoxygenase protein or secrete leukotrienes (a downstream product of 5-lipoxygenase). Differentiation of the cells with DMSO causes an appearance of 5-lipoxygenase protein and leukotriene biosynthesis 48 hours after addition of DMSO. Thus induction of 5-lipoxygenase protein synthesis can be utilized as a test system for analysis of antisense oligonucleotides analogues which interfere with 5-lipoxygenase synthesis in these cells.

A second test system for antisense oligonucleotides makes use of the fact that 5-lipoxygenase is a "suicide" enzyme in that it inactivates itself upon reacting with substrate. Treatment of differentiated HL-60 or other cells expressing 5 lipoxygenase, with 10 µM A23187, a calcium ionophore, promotes translocation of 5-lipoxygenase from the cytosol to the membrane with subsequent activation of the enzyme. Following activation and several rounds of catalysis, the enzyme becomes catalytically inactive. Thus, treatment of the cells with calcium ionophore inactivates endogenous 5-lipoxygenase. It takes the cells approximately 24 hours to recover from A23187 treatment as measured by their ability to synthesize leukotriene $B_4$. Oligonucleotide analogues directed against 5-lipoxygenase can be tested for activity in two HL-60 model systems using the following quantitative assays. The assays are described from the most direct measurement of inhibition of 5-lipoxygenase protein synthesis in intact cells to more downstream events such as measurement of 5-lipoxygenase activity in intact cells.

The most direct effect which oligonucleotide analogues can exert on intact cells and which can be easily be quantitated is specific inhibition of 5-lipoxygenase protein synthesis. To perform this technique, cells can be labelled with $^{35}$S-methionine (50 µCi/mL) for 2 hours at 37° C. to label newly synthesized protein. Cells are extracted to solubilize total cellular proteins and 5-lipoxygenase is immunoprecipitated with 5-lipoxygenase antibody followed by elution from protein A Sepharose beads. The immunoprecipitated proteins are resolved by SDS-polyacrylamide gel electrophoresis and exposed for autoradiography. The amount of immunoprecipitated 5-lipoxygenase is quantitated by scanning densitometry.

A predicted result from these experiments would be as follows. The amount of 5-lipoxygenase protein immunoprecipitated from control cells would be normalized to 100%. Treatment of the cells with 1 µM, 10 µM, and 30 µM of effective oligonucleotide analogues for 48 hours would reduce immunoprecipitated 5-lipoxygenase by 5%, 25% and 75% of control, respectively.

Measurement of 5-lipoxygenase enzyme activity in cellular homogenates could also be used to quantitate the amount of enzyme present which is capable of synthesizing leukotrienes. A radiometric assay has now been developed for quantitating 5-lipoxygenase enzyme activity in cell homogenates using reverse phase HPLC. Cells are broken by sonication in a buffer containing protease inhibitors and EDTA. The cell homogenate is centrifuged at 10,000×g for 30 min and the supernatants analyzed for 5-lipoxygenase activity. Cytosolic proteins are incubated with 10 µM $^{14}$C-arachidonic acid, 2 mM ATP, 50 µM free calcium, 100 µg/ml phosphatidylcholine, and 50 mM bis-Tris buffer, pH 7.0, for 5 min at 37° C. The reactions are quenched by the addition of an equal volume of acetone and the fatty acids extracted with ethyl acetate. The substrate and reaction products are separated by reverse phase HPLC on a Novapak C18 column (Waters Inc., Millford, Mass.). Radioactive peaks are detected by a Beckman model 171 radiochromatography detector. The amount of arachidonic acid converted into di-HETE's and mono-HETE's is used as a measure of 5-lipoxygenase activity.

A predicted result for treatment of DMSO differentiated HL-60 cells for 72 hours with effective oligonucleotide analogues at 1 $\mu$M, 10 $\mu$M, and 30 $\mu$M would be as follows. Control cells oxidize 200 pmol arachidonic acid/5 min/$10^6$ cells. Cells treated with 1 $\mu$M, 10 $\mu$M, and 30 $\mu$M of an effective oligonucleotide analogues would oxidize 195 pmol, 140 pmol, and 60 pmol of arachidonic acid/5 min/$10^6$ cells respectively.

A quantitative competitive enzyme linked immunosorbant assay (ELISA) for the measurement of total 5-lipoxygenase protein in cells has been developed. Human 5-lipoxygenase expressed in E. coli and purified by extraction, Q-Sepharose, hydroxyapatite, and reverse phase HPLC is used as a standard and as the primary antigen to coat microtiter plates. 25 ng of purified 5-lipoxygenase is bound to the microtiter plates overnight at 40° C. The wells are blocked for 90 min with 5% goat serum diluted in 20 mM Tris·HCL buffer, pH 7.4, in the presence of 150 mM NaCl (TBS). Cell extracts (0.2% Triton X-100, 12,000×g for 30 min.) or purified 5-lipoxygenase were incubated with a 1:4000 dilution of 5-lipoxygenase polyclonal antibody in a total volume of 100 $\mu$L in the microtiter wells for 90 min. The antibodies are prepared by immunizing rabbits with purified human recombinant 5-lipoxygenase. The wells are washed with TBS containing 0.05% tween 20 (TBST), then incubated with 100 $\mu$L of a 1:1000 dilution of peroxidase conjugated goat anti-rabbit IgG (Cappel Laboratories, Malvern, Pa.) for 60 min at 25° C. The wells are washed with TBST and the amount of peroxidase labelled second antibody determined by development with tetramethylbenzidine.

Predicted results from such an assay using a 30 mer oligonucleotide analogue at 1 $\mu$M, 10 $\mu$M, and 30 $\mu$M would be 30 ng, 18 ng and 5 ng of 5-lipoxygenase per $10^6$ cells, respectively with untreated cells containing about 34 ng 5-lipoxygenase.

A net effect of inhibition of 5-lipoxygenase biosynthesis is a diminution in the quantities of leukotrienes released from stimulated cells. DMSO-differentiated HL-60 cells release leukotriene B4 upon stimulation with the calcium ionophore A23187. Leukotriene B4 released into the cell medium can be quantitated by radioimmunoassay using commercially available diagnostic kits (New England Nuclear, Boston, Mass.). Leukotriene B4 production can be detected in HL-60 cells 48 hours following addition of DMSO to differentiate the cells into a neutrophil-like cell. Cells (2×$10^5$ cells/mL) will be treated with increasing concentrations of oligonucleotide analogues for 48–72 hours in the presence of 1.3% DMSO. The cells are washed and re-suspended at a concentration of 2×$10^6$ cell/mL in Dulbecco's phosphate buffered saline containing 1% delipidated bovine serum albumin. Cells are stimulated with 10 $\mu$M calcium ionophore A23187 for 15 min and the quantity of LTB4 produced from 5×$10^5$ cell determined by radioimmunoassay as described by the manufacturer.

Using this assay the following results would likely be obtained with a 15-mer modified linkage bearing antisense oligonucleotide (GCAAGGTCACTGAAG) directed to the 5-LO mRNA. Cells will be treated for 72 hours with either 1 $\mu$M, 10 $\mu$M or 30 $\mu$M oligonucleotide analogue in the presence of 1.3% DMSO. The quantity of $LTB_4$ produced from 5×$10^5$ cells would be expected to be about 75 pg, 50 pg, and 35 pg. respectively with untreated differentiated cells producing 75 pg $LTB_4$.

E. In Vivo Assay

Inhibition of the production of 5-lipoxygenase in the mouse can be demonstrated in accordance with the following protocol. Topical application of arachidonic acid results in the rapid production of leukotriene $B_4$. leukotriene $C_4$ and prostaglandin $E_2$ in the skin followed by edema and cellular infiltration. Certain inhibitors of 5-lipoxygenase have been known to exhibit activity in this assay. For the assay, 2 mg of arachidonic acid is applied to a mouse ear with the contralateral ear serving as a control. The polymorphonuclear cell infiltrate is assayed by myeloperoxidase activity in homogenates taken from a biopsy 1 hour following the administration of arachidonic acid. The edematous response is quantitated by measurement of ear thickness and wet weight of a punch biopsy. Measurement of leukotriene $B_4$ produced in biopsy specimens is performed as a direct measurement of 5-lipoxygenase activity in the tissue. Oligonucleotide analogues will be applied topically to both ears 12 to 24 hours prior to administration of arachidonic acid to allow optimal activity of the compounds. Both ears are pretreated for 24 hours with either 0.1 $\mu$mol, 0.3 $\mu$mol, or 1.0 $\mu$mol of the oligonucleotide analogue prior to challenge with arachidonic acid. Values are expressed as the mean for three animals per concentration. Inhibition of polymorphonuclear cell infiltration for 0.1 $\mu$mol, 0.3 $\mu$mol, and 1 $\mu$mol is expected to be about 10%, 75% and 92% of control activity, respectively. Inhibition of edema is expected to be about 3%, 58% and 90%, respectively while inhibition of leukotriene $B_4$ production would be expected to be about 15%, 79% and 99%, respectively.

What is claimed is:

1. An oligonucleotide analogue in which at least some of the subunits of the analogue have the structure:

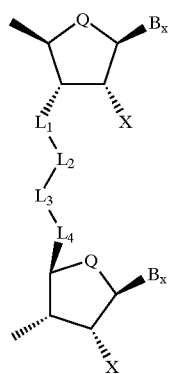

wherein $B_x$ is a variable base moiety;

Q is O, $CH_2$, CHF or $CF_2$;

X is H; OH; $C_1$ to $C_{10}$ lower alkyl, substituted lower alkyl, alkaryl or aralkyl; F; Cl; Br; CN; $CF_3$; $OCF_3$; OCN; O—, S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; or an RNA cleaving group, wherein at least one X is OH;

$L_1$ and $L_4$ are, independently, $CH_2$, C=O, C=S, C—$NH_2$, C—$NHR_3$, C—OH, C—SH, C—O—R, or C—S—$R_1$; and $L_2$ and $L_3$ are, independently, $CR_1R_2$, C=$CR_1R_2$, C=$NR_3$, P(O)$R_4$, P(S)$R_4$, C=O, C=S, O, S, SO, $SO_2$, $NR_3$ or $SiR_5R_6$; or, together, form part of an alkene, alkyne, aromatic ring, carbocycle or heterocycle, or $L_1, L_2, L_3$ and $L_4$, together, comprise a —CH=N—NH—$CH_2$— or —$CH_2$—O—N=CH— moiety;

$R_1$ and $R_2$ are, independently, H; OH; SH; $NH_2$; $C_1$ to $C_{10}$ alkyl, substituted alkyl, alkenyl, alkaryl or aralkyl;

alkoxy; thioalkoxy; alkylamino; aralkylamino; substituted alkylamino; heterocycloalkyl; heterocycloalkylamino; aminoalkylamino; polyalkylamino; halo; formyl; keto; benzoxy; carboxamido; thiocarboxamido; ester; thioester; carboxamidine; carbamyl; ureido; guanidino; or an RNA cleaving group;

$R_3$ is H, OH, $NH_2$, lower alkyl, substituted lower alkyl, alkoxy, lower alkenyl, aralkyl, alkylamino, aralkylamino, substituted alkylamino, heterocyclocalkyl, heterocycloalkylamino, aminoalkylamino, polyalkylamino, or an RNA cleaving group;

$R_4$ is OH, SH, $NH_2$, O-alkyl, S-alkyl, NH-alkyl, O-alkylheterocycle, S-alkylheterocycle, N-alkylheterocycle or a nitrogen-containing heterocycle; and $R_5$ and $R_6$ are, independently, $C_1$ to $C_6$ alkyl or alkoxy; provided that if $L_1$ is C=O or C=S then $L_2$ is not $NR_3$ or if $L_4$ is C=O or C=S then $L_3$ is not $NR_3$; and that if one of $L_2$ or $L_3$ is C=O or C=S then the other of $L_2$ or $L_3$ is not $NR_3$; and if $L_2$ is $P(O)R_4$ and $R_4$ is OH and X is OH and $B_x$ is uracil or adenine, then $L_3$ is not O; that if $L_1$, $L_2$ and $L_4$ are $CH_2$ and X is H or OH and Q is O then $L_3$ is not S, SO or $SO_2$.

2. The oligonucleotide analogue of claim 1 wherein Q is O.

3. The oligonucleotide analogue of claim 1 wherein each of $L_1$ and $L_4$ are $CR_1R_2$.

4. The oligonucleotide analogue of claim 3 wherein $R_1$ and $R_2$ are each H.

5. The oligonucleotide analogue of claim 4 wherein Q is O.

6. The oligonucleotide analogue of claim 1 wherein $L_2$ and $L_3$ are, independently, $CR_1R_2$, O, $P(O)R_4$, $P(S)R_4$ or $NR_3$.

7. The oligonucleotide analogue of claim 6 wherein one of $L_2$ and $L_3$ is $CR_1R_2$ and the other of $L_2$ and $L_3$ is $P(O)R_4$ or $P(S)R_4$.

8. The oligonucleotide analogue of claim 6 wherein $L_2$ is O and $L_3$ is $P(O)R_4$ or $P(S)R_4$.

9. The oligonucleotide analogue of claim 1 wherein each of $L_2$ and $L_3$ is $NR_3$.

10. The oligonucleotide analogue of claim 9 wherein $R_3$ is H.

11. The oligonucleotide analogue of claim 1 wherein $L_1$ and $L_4$ are each $CH_2$ and each of $L_2$ and $L_3$ are $NR_3$.

12. The oligonucleotide analogue of claim 1 wherein $L_2$ and $L_3$ taken together form a portion of a cyclopropyl, cyclobutyl, ethyleneoxy, ethyl aziridine or substituted ethyl aziridine ring.

13. The oligonucleotide analogue of claim 1 wherein $L_2$ and $L_3$ taken together form a portion of a $C_3$ to $C_6$ carbocycle or 4-, 5- or 6-membered nitrogen heterocycle.

14. The oligonucleotide analogue of claim 1 wherein X is H.

15. The oligonucleotide analogue of claim 1 wherein X is OH.

16. The oligonucleotide analogue of claim 1 wherein X is H, OH, F, O-alkyl or O-alkenyl and Q is O.

17. The oligonucleotide analogue of claim 1 wherein $B_x$ is adenine, guanine, uracil, thymine, cytosine, 2-aminoadenine or 5-methylcytosine.

18. The oligonucleotide analogue of claim 17 wherein Q is O.

19. The oligonucleotide analogue of claim 21 wherein $L_1$ and $L_4$ are each $CH_2$.

20. The oligonucleotide analogue of claim 19 wherein $L_2$ and $L_3$ are each NH.

21. The oligonucleotide analogue of claim 19 wherein one of $L_2$ and $L_3$ is O and the other of $L_2$ and $L_3$ is NH.

22. The oligonucleotide analogue of claim 19 wherein $L_2$ is NH and $L_3$ is O.

23. The oligonucleotide analogue of claim 21 wherein $L_2$ is O and $L_3$ is NH.

24. The oligonucleotide analogue of claim 1 comprising from about 5 to about 50 subunits having said structure.

25. The oligonucleotide analogue of claim 1 wherein substantially all of the subunits have said structure.

26. The oligonucleotide analogue of claim 1 wherein substantially alternating subunits have said structure.

27. The oligonucleotide analogue of claim 1 in a pharmaceutically acceptable carrier.

28. An oligonucleotide analogue in which at least some of the subunits of the analogue have the structure:

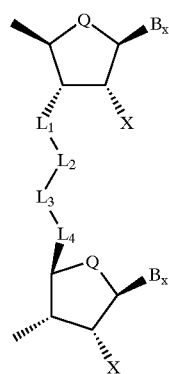

wherein $B_x$ is a variable base moiety;

Q is O, $CH_2$, CHF or $CF_2$;

X is H; OH; $C_1$ to $C_{10}$ lower alkyl, substituted lower alkyl, alkaryl or aralkyl; F; Cl; Br; CN; $CF_3$; $OCF_3$; OCN; O—, S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; or an RNA cleaving group, wherein at least one X is OH;

$L_1$ and $L_4$ are, independently, $CH_2$, C=O, C=S, C—$NH_2$, C—$NHR_3$, C—OH, C—SH, C—O—$R_1$ or C—S—$R_1$; and $L_2$ and $L_3$ are, independently, $CR_1R_2$, C=$CR_1R_2$, C=$NR_3$, $P(O)R_4$, $P(S)R_4$, C=O, C=S, O, S, SO, $SO_2$, $NR_3$ or $SiR_5R_6$; or, together, form part of an alkene, alkyne, aromatic ring, carbocycle or heterocycle, or $L_1$, $L_2$, $L_3$ and $L_4$, together, comprise a —CH=N—NH—$CH_2$— or —$CH_2$—O—N=CH— moiety;

$R_1$ and $R_2$ are, independently, H; OH; SH; $NH_2$; $C_1$ to $C_{10}$ alkyl, substituted alkyl, alkenyl, alkaryl or aralkyl; alkoxy; thioalkoxy; alkylamino; aralkylamino; substituted alkylamino; heterocycloalkyl; heterocycloalkylamino; aminoalkylamino; polyalkylamino; halo; formyl; keto; benzoxy; carboxamido; thiocarboxamido; ester; thioester; carboxamidine; carbamyl; ureido; guanidino; or an RNA cleaving group;

$R_3$ is H, OH, $NH_2$, lower alkyl, substituted lower alkyl, alkoxy, lower alkenyl, aralkyl, alkylamino, aralkylamino, substituted alkylamino, heterocyclocalkyl, heterocycloalkylamino, aminoalkylamino, polyalkylamino, or an RNA cleaving group;

$R_4$ is OH, SH, $NH_2$, O-alkyl, S-alkyl, NH-alkyl, O-alkylheterocycle, S-alkylheterocycle, N-alkylheterocycle or a nitrogen-containing heterocycle; and $R_5$ and $R_6$ are, independently, $C_1$ to $C_6$ alkyl or alkoxy;

provided if $L_1$ is C=O or C=S then $L_2$ is not $NR_3$ or if $L_4$ is C=O or C=S then $L_3$ is not $NR_3$; and that if one of $L_2$ or $L_3$ is C=O or C=S then the other of $L_2$ or $L_3$ is not $NR_3$; and if $L_2$ is $P(O)R_4$ and $R_4$ is OH and X is OH and $B_x$ is uracil or adenine, then $L_3$ is not O; and that if $L_1$, $L_2$ and $L_4$ are $CH_2$ and X is H or OH and Q is O then $L_3$ is not S, SO or $SO_2$;

wherein said oligonucleotide analogue exhibits improved nuclease resistance as compared to corresponding natural oligonucleotides.

* * * * *

UNITED STATES PATENT AND TRADEMARK OFFICE
CERTIFICATE OF CORRECTION

PATENT NO. : 6,900,301 B2
DATED : May 31, 2005
INVENTOR(S) : Phillip Dan Cook et al.

It is certified that error appears in the above-identified patent and that said Letters Patent is hereby corrected as shown below:

Column 54,
Line 58, delete "C-O-R," and insert -- $C\text{-}O\text{-}R_1$ --;

Column 55,
Line 64, delete "21" and insert -- 1 --.

Signed and Sealed this

Thirteenth Day of June, 2006

JON W. DUDAS
*Director of the United States Patent and Trademark Office*

SEQUENCE LISTING

<160> NUMBER OF SEQ ID NOS: 12

<210> SEQ ID NO 1
<211> LENGTH: 16
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: (1)..(8)

-continued

```
<223> OTHER INFORMATION: phosphodiester linkage
<221> NAME/KEY: misc_feature
<222> LOCATION: (9)..(16)
<223> OTHER INFORMATION: phosphodiester linkage
<221> NAME/KEY: misc_feature
<222> LOCATION: (8)..(9)
<223> OTHER INFORMATION: Phosphodiester; N-Methyl-Hydroxyamino;
      N-Methyl-Aminohydroxy; N,N'-Dimethyl-Hydrazino; Aminohydroxy
<221> NAME/KEY: misc_feature
<222> LOCATION: (8)..(9)
<223> OTHER INFORMATION: Phosphodiester; N-Methyl-Hydroxyamino;
      N-Methyl-Aminohydroxy; N,N'-Dimethyl-Hydrazino; Aminohydroxy

<400> SEQUENCE: 1
gcgttttttt tttgcg                                                 16

<210> SEQ ID NO 2
<211> LENGTH: 16
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: (1)..(7)
<223> OTHER INFORMATION: phosphodiester linkage
<221> NAME/KEY: misc_feature
<222> LOCATION: (10)..(16)
<223> OTHER INFORMATION: phosphodiester linkage
<221> NAME/KEY: misc_feature
<222> LOCATION: (7)..(8)
<223> OTHER INFORMATION: Phosphodiester; N-Methyl-Hydroxyamino;
      N-Methyl-Aminohydroxy; N,N'-Dimethyl-Hydrazino; Aminohydroxy
<221> NAME/KEY: misc_feature
<222> LOCATION: (9)..(10)
<223> OTHER INFORMATION: Phosphodiester; N-Methyl-Hydroxyamino;
      N-Methyl-Aminohydroxy; N,N'-Dimethyl-Hydrazino; Aminohydroxy
<221> NAME/KEY: misc_feature
<222> LOCATION: (8)..(9)
<223> OTHER INFORMATION: phosphodiester linkage

<400> SEQUENCE: 2
gcgttttttt tttgcg                                                 16

<210> SEQ ID NO 3
<211> LENGTH: 16
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: (1)..(6)
<223> OTHER INFORMATION: phosphodiester linkage
<221> NAME/KEY: misc_feature
<222> LOCATION: (7)..(8)
<223> OTHER INFORMATION: phosphodiester linkage
<221> NAME/KEY: misc_feature
<222> LOCATION: (9)..(10)
<223> OTHER INFORMATION: phosphodiester linkage
<221> NAME/KEY: misc_feature
<222> LOCATION: (11)..(16)
<223> OTHER INFORMATION: phosphodiester linkage
<221> NAME/KEY: misc_feature
<222> LOCATION: (6)..(7)
<223> OTHER INFORMATION: Phosphodiester; N-Methyl-Hydroxyamino;
      N-Methyl-Aminohydroxy; N,N'-Dimethyl-Hydrazino; Aminohydroxy
<221> NAME/KEY: misc_feature
<222> LOCATION: (10)..(11)
<223> OTHER INFORMATION: Phosphodiester; N-Methyl-Hydroxyamino;
      N-Methyl-Aminohydroxy; N,N'-Dimethyl-Hydrazino; Aminohydroxy
<221> NAME/KEY: misc_feature
<222> LOCATION: (8)..(9)
<223> OTHER INFORMATION: Phosphodiester; N-Methyl-Hydroxyamino;
      N-Methyl-Aminohydroxy; N,N'-Dimethyl-Hydrazino; Aminohydroxy

<400> SEQUENCE: 3
``` gcgtttttttt tttgcg         16

```
<210> SEQ ID NO 4
<211> LENGTH: 16
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: (1)..(4)
<223> OTHER INFORMATION: phosphodiester linkage
<221> NAME/KEY: misc_feature
<222> LOCATION: (13)..(16)
<223> OTHER INFORMATION: phosphodiester linkage
<221> NAME/KEY: misc_feature
<222> LOCATION: (5)..(8)
<223> OTHER INFORMATION: phosphodiester linkage
<221> NAME/KEY: misc_feature
<222> LOCATION: (9)..(12)
<223> OTHER INFORMATION: phosphodiester linkage
<221> NAME/KEY: misc_feature
<222> LOCATION: (4)..(5)
<223> OTHER INFORMATION: Phosphodiester; N-Methyl-Aminohydroxy
<221> NAME/KEY: misc_feature
<222> LOCATION: (12)..(13)
<223> OTHER INFORMATION: Phosphodiester; N-Methyl-Aminohydroxy
<221> NAME/KEY: misc_feature
<222> LOCATION: (8)..(9)
<223> OTHER INFORMATION: Phosphodiester; N-Methyl-Aminohydroxy

<400> SEQUENCE: 4
``` gcgtttttttt tttgcg         16

```
<210> SEQ ID NO 5
<211> LENGTH: 16
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: (1)..(5)
<223> OTHER INFORMATION: phosphodiester linkage
<221> NAME/KEY: misc_feature
<222> LOCATION: (6)..(7)
<223> OTHER INFORMATION: phosphodiester linkage
<221> NAME/KEY: misc_feature
<222> LOCATION: (8)..(9)
<223> OTHER INFORMATION: phosphodiester linkage
<221> NAME/KEY: misc_feature
<222> LOCATION: (12)..(16)
<223> OTHER INFORMATION: phosphodiester linkage
<221> NAME/KEY: misc_feature
<222> LOCATION: (10)..(11)
<223> OTHER INFORMATION: phosphodiester linkage
<221> NAME/KEY: misc_feature
<222> LOCATION: (5)..(6)
<223> OTHER INFORMATION: Phosphodiester; N-Methyl-Hydroxyamino;
      aminohydroxy
<221> NAME/KEY: misc_feature
<222> LOCATION: (11)..(12)
<223> OTHER INFORMATION: Phosphodiester; N-Methyl-Hydroxyamino;
      aminohydroxy
<221> NAME/KEY: misc_feature
<222> LOCATION: (9)..(10)
<223> OTHER INFORMATION: Phosphodiester; N-Methyl-Hydroxyamino;
      aminohydroxy
<221> NAME/KEY: misc_feature
<222> LOCATION: (7)..(8)
<223> OTHER INFORMATION: Phosphodiester; N-Methyl-Hydroxyamino;
      aminohydroxy

<400> SEQUENCE: 5
``` gcgtttttttt tttgcg         16

-continued

```
<210> SEQ ID NO 6
<211> LENGTH: 16
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: (1)..(4)
<223> OTHER INFORMATION: phosphodiester linkage
<221> NAME/KEY: misc_feature
<222> LOCATION: (5)..(7)
<223> OTHER INFORMATION: phosphodiester linkage
<221> NAME/KEY: misc_feature
<222> LOCATION: (8)..(9)
<223> OTHER INFORMATION: phosphodiester linkage
<221> NAME/KEY: misc_feature
<222> LOCATION: (10)..(12)
<223> OTHER INFORMATION: phosphodiester linkage
<221> NAME/KEY: misc_feature
<222> LOCATION: (13)..(16)
<223> OTHER INFORMATION: phosphodiester linkage
<221> NAME/KEY: misc_feature
<222> LOCATION: (4)..(5)
<223> OTHER INFORMATION: Phosphodiester; N-methyl-Aminohydroxy;
      N,N'-Dimethyl-Hydrazino; Aminohydroxy
<221> NAME/KEY: misc_feature
<222> LOCATION: (12)..(13)
<223> OTHER INFORMATION: Phosphodiester; N-methyl-Aminohydroxy;
      N,N'-Dimethyl-Hydrazino; Aminohydroxy
<221> NAME/KEY: misc_feature
<222> LOCATION: (9)..(10)
<223> OTHER INFORMATION: Phosphodiester; N-methyl-Aminohydroxy;
      N,N'-Dimethyl-Hydrazino; Aminohydroxy
<221> NAME/KEY: misc_feature
<222> LOCATION: (7)..(8)
<223> OTHER INFORMATION: Phosphodiester; N-methyl-Aminohydroxy;
      N,N'-Dimethyl-Hydrazino; Aminohydroxy

<400> SEQUENCE: 6 gcgtttttttt tttgcg                                              16

<210> SEQ ID NO 7
<211> LENGTH: 16
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: (1)..(4)
<223> OTHER INFORMATION: phosphodiester linkage
<221> NAME/KEY: misc_feature
<222> LOCATION: (5)..(6)
<223> OTHER INFORMATION: phosphodiester linkage
<221> NAME/KEY: misc_feature
<222> LOCATION: (7)..(8)
<223> OTHER INFORMATION: phosphodiester linkage
<221> NAME/KEY: misc_feature
<222> LOCATION: (9)..(10)
<223> OTHER INFORMATION: phosphodiester linkage
<221> NAME/KEY: misc_feature
<222> LOCATION: (13)..(16)
<223> OTHER INFORMATION: phosphodiester linkage
<221> NAME/KEY: misc_feature
<222> LOCATION: (11)..(12)
<223> OTHER INFORMATION: phosphodiester linkage
<221> NAME/KEY: misc_feature
<222> LOCATION: (4)..(5)
<223> OTHER INFORMATION: Phosphodiester; N-Methyl-Hydroxyamino;
      N-Methyl-Aminohydroxy; N,N'-Dimethyl-Hydrazino; Aminohydroxy
<221> NAME/KEY: misc_feature
<222> LOCATION: (10)..(11)
<223> OTHER INFORMATION: Phosphodiester; N-Methyl-Hydroxyamino;
      N-Methyl-Aminohydroxy; N,N'-Dimethyl-Hydrazino; Aminohydroxy
<221> NAME/KEY: misc_feature
<222> LOCATION: (12)..(13)
<223> OTHER INFORMATION: Phosphodiester; N-Methyl-Hydroxyamino;
```

-continued

```
      N-Methyl-Aminohydroxy; N,N'-Dimethyl-Hydrazino; Aminohydroxy
<221> NAME/KEY: misc_feature
<222> LOCATION: (8)..(9)
<223> OTHER INFORMATION: Phosphodiester; N-Methyl-Hydroxyamino;
      N-Methyl-Aminohydroxy; N,N'-Dimethyl-Hydrazino; Aminohydroxy
<221> NAME/KEY: misc_feature
<222> LOCATION: (6)..(7)
<223> OTHER INFORMATION: Phosphodiester; N-Methyl-Hydroxyamino;
      N-Methyl-Aminohydroxy; N,N'-Dimethyl-Hydrazino; Aminohydroxy

<400> SEQUENCE: 7
gcgttttttt tttgcg                                                    16

<210> SEQ ID NO 8
<211> LENGTH: 18
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: (1)..(9)
<223> OTHER INFORMATION: phosphodiester linkage
<221> NAME/KEY: misc_feature
<222> LOCATION: (10)..(18)
<223> OTHER INFORMATION: phosphodiester linkage
<221> NAME/KEY: misc_feature
<222> LOCATION: (9)..(10)
<223> OTHER INFORMATION: Phosphodiester; Oxime; N-Methyl-Aminohydroxy;
      N,N'-Dimethyl-Hydra zino; Aminohydroxy

<400> SEQUENCE: 8
ctcgtacctt tccggtcc                                                  18

<210> SEQ ID NO 9
<211> LENGTH: 18
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: (1)..(8)
<223> OTHER INFORMATION: phosphodiester linkage
<221> NAME/KEY: misc_feature
<222> LOCATION: (11)..(18)
<223> OTHER INFORMATION: phosphodiester linkage
<221> NAME/KEY: misc_feature
<222> LOCATION: (9)..(10)
<223> OTHER INFORMATION: phosphodiester linkage
<221> NAME/KEY: misc_feature
<222> LOCATION: (8)..(9)
<223> OTHER INFORMATION: Phosphodiester; N-Methyl-Hydroxyamino;
      N-Methyl-Aminohydroxy; N,N'-Dimethyl-Hydrazino; Aminohydroxy
<221> NAME/KEY: misc_feature
<222> LOCATION: (10)..(11)
<223> OTHER INFORMATION: Phosphodiester; N-Methyl-Hydroxyamino;
      N-Methyl-Aminohydroxy; N,N'-Dimethyl-Hydrazino; Aminohydroxy

<400> SEQUENCE: 9
ctcgtacttt tccggtcc                                                  18

<210> SEQ ID NO 10
<211> LENGTH: 15
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: (1)..(13)
<223> OTHER INFORMATION: phosphodiester linkage
<221> NAME/KEY: misc_feature
<222> LOCATION: (14)..(15)
<223> OTHER INFORMATION: phosphodiester linkage
<221> NAME/KEY: misc_feature
```

```
<222> LOCATION: (13)..(14)
<223> OTHER INFORMATION: Phosphodiester; Oxime; N-Methyl-Hydroxyamino;
      N-Methyl-Aminohydroxy; N,N'-Dimethyl-Hydrazino; Aminohydroxy

<400> SEQUENCE: 10
cgactatgca atttc                                                      15

<210> SEQ ID NO 11
<211> LENGTH: 18
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: (1)..(9)
<223> OTHER INFORMATION: phosphodiester linkage
<221> NAME/KEY: misc_feature
<222> LOCATION: (10)..(18)
<223> OTHER INFORMATION: phosphodiester linkage
<221> NAME/KEY: misc_feature
<222> LOCATION: (9)..(10)
<223> OTHER INFORMATION: Phosphodiester; Oxime; N-Methyl-Aminohydroxy;
      N,N'-Dimethyl-Hydra zino; Aminohydroxy

<400> SEQUENCE: 11
ctcgtacctt tccggtcc                                                   18

<210> SEQ ID NO 12
<211> LENGTH: 15
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: (1)..(13)
<223> OTHER INFORMATION: phosphodiester linkage
<221> NAME/KEY: misc_feature
<222> LOCATION: (14)..(15)
<223> OTHER INFORMATION: phosphodiester linkage
<221> NAME/KEY: misc_feature
<222> LOCATION: (13)..(14)
<223> OTHER INFORMATION: Phosphodiester; N-Methyl-Hydroxyamino;
      N-Methyl-Aminohydroxy; N,N'-Dimethyl-Hydrazino; Aminohydroxy

<400> SEQUENCE: 12
cgactatgca atttc                                                      15
```